(12) United States Patent
Acker et al.

(10) Patent No.: US 11,833,299 B2
(45) Date of Patent: *Dec. 5, 2023

(54) CLINICAL DECISION SUPPORT SYSTEM AND METHODS

(71) Applicant: Mallinckrodt Pharmaceuticals Ireland Limited, Dublin (IE)

(72) Inventors: Jaron Acker, New York, NY (US); Craig R. Tolmie, Stoughton, WI (US)

(73) Assignee: Mallinckrodt Pharmaceuticals Ireland Limited, Dublin (IE)

( * ) Notice: Subject to any disclaimer, the term of this patent is extended or adjusted under 35 U.S.C. 154(b) by 967 days.

This patent is subject to a terminal disclaimer.

(21) Appl. No.: 16/677,435

(22) Filed: Nov. 7, 2019

(65) Prior Publication Data

US 2020/0139061 A1 May 7, 2020

Related U.S. Application Data

(62) Division of application No. 14/026,807, filed on Sep. 13, 2013, now Pat. No. 10,512,741.

(51) Int. Cl.
*A61M 16/00* (2006.01)
*A61M 16/12* (2006.01)
(Continued)

(52) U.S. Cl.
CPC ...... *A61M 16/0051* (2013.01); *A61M 16/024* (2017.08); *A61M 16/104* (2013.01);
(Continued)

(58) Field of Classification Search
CPC ............ A61M 16/0051; A61M 16/024; A61M 16/104; A61M 16/12; A61M 16/0672;
(Continued)

(56) References Cited

U.S. PATENT DOCUMENTS 5,558,083 A 9/1996 Bathe et al.
5,713,349 A * 2/1998 Keaney ............... A61M 16/022
128/204.23

(Continued)

FOREIGN PATENT DOCUMENTS

WO WO-03020211 A2 * 3/2003 ............. A61K 33/00
WO 2007008825 A2 1/2007

OTHER PUBLICATIONS

NOmax DS (Delivery System): Operation Manual (800 ppm INOMAX (nitric oxide) for Inhalation), Ikaria, Inc. 2010, 112 Pages.
(Continued)

*Primary Examiner* — Victoria Murphy

(57) ABSTRACT

The present invention provides clinical decision support that can be used with non-portable and portable systems when delivering and/or monitoring delivery of a therapeutic gas comprising nitric oxide to a patient. Further, clinical decision support can be used with non-portable and portable systems during delivery and/or monitoring of delivery of therapeutic gas when nebulized drugs may and/or may not be being delivered to a patient (e.g., when nebulizers are delivered upstream in the inspiratory limb of the breathing circuit, into a breathing gas delivery system, etc.).

18 Claims, 48 Drawing Sheets

(51) Int. Cl.
*A61M 16/10* (2006.01)
*G16H 50/20* (2018.01)
*G16H 20/10* (2018.01)
*A61M 16/06* (2006.01)

(52) U.S. Cl.
CPC ............ *A61M 16/12* (2013.01); *G16H 20/10* (2018.01); *G16H 50/20* (2018.01); *A61M 16/0672* (2014.02); *A61M 2016/0039* (2013.01); *A61M 2202/0275* (2013.01); *A61M 2205/505* (2013.01); *A61M 2205/581* (2013.01); *A61M 2205/583* (2013.01)

(58) Field of Classification Search
CPC .. A61M 2016/0039; A61M 2202/0275; A61M 2205/505; A61M 2205/581; A61M 2205/583; G16H 20/10; G16H 50/20
See application file for complete search history.

(56) References Cited

U.S. PATENT DOCUMENTS

| | | | |
|---|---|---|---|
| 5,732,693 A | 3/1998 | Bathe et al. | |
| 5,732,694 A | 3/1998 | Bathe et al. | |
| 5,752,504 A | 5/1998 | Bathe | |
| 6,125,846 A | 10/2000 | Bathe et al. | |
| 7,201,166 B2 | 4/2007 | Blaise et al. | |
| 7,523,752 B2 | 4/2009 | Montgomery et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,431,163 B2 | 4/2013 | Baldassarre et al. | |
| 8,573,209 B2 | 11/2013 | Bathe et al. | |
| 8,573,210 B2 | 11/2013 | Bathe et al. | |
| 8,776,794 B2 | 7/2014 | Bathe et al. | |
| 8,776,795 B2 | 7/2014 | Bathe et al. | |
| 8,795,741 B2 | 8/2014 | Baldassarre | |
| 8,846,112 B2 | 9/2014 | Baldassarre | |
| 2003/0140921 A1* | 7/2003 | Smith | A61M 15/0031 128/200.14 |
| 2004/0040560 A1* | 3/2004 | Euliano | A61B 5/082 128/204.23 |
| 2004/0099263 A1* | 5/2004 | Melker | A61M 16/0488 128/207.14 |
| 2006/0229531 A1 | 10/2006 | Goldberger et al. | |
| 2007/0181126 A1* | 8/2007 | Tolmie | A61M 16/12 128/204.21 |
| 2008/0078385 A1 | 4/2008 | Xiao et al. | |
| 2008/0078390 A1 | 4/2008 | Milne et al. | |
| 2012/0240927 A1* | 9/2012 | Bathe | A61M 16/085 128/203.12 |
| 2013/0118486 A1 | 5/2013 | Schnitman et al. | |
| 2013/0192595 A1 | 8/2013 | Tolmie et al. | |
| 2013/0218040 A1* | 8/2013 | Haveri | A61M 16/085 600/532 |

OTHER PUBLICATIONS

NOmax DSIR (Delivery System): Operation Manual (800 ppm INOMAX (nitric oxide) for Inhalation), Ikaria, Inc. 2012, 136 Pages.
NOmax Label, Nitric Oxide Gas, INO Therapeutics 2013, 2 Pages.
NOvent Delivery System: Operation and Maintenance Manual (CGA Variant), Datex-Ohmeda, Inc. 2000, 180 Pages.
Using the INOpulse DS Subject Guide, Ikaria, Inc. 2012, 50 Pages.

* cited by examiner

1. Maximum deliverable NO concentration (ppm)
2. Constant inspiratory flowrate (L/min)

CLINICAL DECISION SUPPORT SYSTEM AND METHODS

CLAIM OF PRIORITY

This application is a divisional application of U.S. patent application Ser. No. 14/026,807, filed on Sep. 13, 2013, the entire contents of which are hereby incorporated by reference.

FIELD

The present invention generally relates to clinical decision support used and/or provided with systems and methods during delivery and/or monitoring of delivery of a therapeutic gas when nebulized drugs may and/or may not be being delivered to the patient.

BACKGROUND

Clinical decision support systems can be interactive decision support system computer software designed to assist clinicians and other health professionals with decision making tasks (e.g., such as determining diagnosis of patient data). Such systems can provide substantial benefit assisting clinicians and other health professionals by providing information and/or options such that errors made in decisions can be reduced. Further, clinical decision support can be particularly beneficial when medicine and/or systems used may be complex and/or may have specific requirements (e.g., delivery requirements, dosing requirements, etc.). Also, clinical decision support software can be designed to control elements of systems that may be complex and/or are affiliated with medicine that may require specific delivery requirements.

One example of a medicine and/or system used that may be complex, have specific requirements, and/or benefit from using clinical decision support is the delivery and/or monitoring of delivery of Nitric Oxide (NO) gas for therapeutic purposes. Nitric oxide (NO) gas, when inhaled, acts to dilate blood vessels in the lungs, improving oxygenation of the blood and reducing pulmonary hypertension. Because of this, nitric oxide can be provided in inspiratory breathing gases for patients with pulmonary hypertension.

Further, when delivering NO gas for therapeutic purpose clinicians may deliver drugs through nebulizers. These nebulized drugs may interfere and/or react with elements in the system that is delivering and/or monitoring delivery of NO gas to the patient. To minimize this, generally speaking, certain elements of the system that may be effected by the nebulized drug are located upstream of nebulizers located in the inspiratory limb of the breathing circuit. However, some studies have demonstrated greater drug efficacy of drugs delivered through nebulizers when the nebulizers are placed further upstream in the inspiratory limb of the breathing circuit. This can cause elements of the system that may be affected by the nebulized drug to be located in substantial proximity and/or downstream from the nebulizers.

Following the above example, if the clinician and other health professional was provided with additional information and/or options they may be able to use the system delivering NO and the nebulizers without substantial risk of damaging elements of the system and/or providing incorrect dosing to a patient. For example, clinical decision support could be used to provide relevant information and/or options to reduce the risk of error that may be caused by the introduction of nebulized drugs into a breathing circuit which also is in fluid communication with elements that may be affected by the nebulized drug.

The above is but one of many scenarios where clinicians and other health professionals can be presented decision making tasks that may assisted with the use of clinical decision support. Accordingly, it would be beneficial if clinical decision support could be used with systems and methods for delivery and/or monitoring of delivery of NO gas for therapeutic purposes.

SUMMARY

In exemplary embodiments, a computer implemented method of providing clinical decision support to users of a therapeutic gas delivery system can include, but is not limited to, storing (e.g., in processor readable memory accessible by processors of a therapeutic gas delivery system) logic based information for a nebulizer mode; displaying (e.g., in a graphical user interface of the therapeutic gas delivery system) an option to activate a nebulizer mode; receiving (e.g., via input in the graphical user interface) and storing (e.g., in processor readable memory) run information including start nebulizer mode information and duration run nebulizer mode information; and/or processing (e.g., using processors of the therapeutic gas delivery system) the logic based information for nebulizer mode and the run nebulizer mode information thereby starting the nebulizer mode. Further, in exemplary embodiments, when nebulizer mode starts sampling may stop for a duration of time that can be based on the received duration run nebulizer mode information. Further still, in exemplary embodiments, the method can include displaying, in a graphical user interface of the therapeutic gas delivery system, delivery information indicating delivery of therapeutic gas when sampling has stopped.

In exemplary embodiments, the delivery information can be provided in a bar graph indicating that over delivery, under delivery, or appropriate delivery.

In exemplary embodiments, the delivery information can include concentration information in parts per million (PPM).

In exemplary embodiments, the concentration information can be based on NO flow sensor and Injector Module sensor ratio-metric calculation.

BRIEF DESCRIPTION OF THE DRAWINGS

The features and advantages of the present invention will be more fully understood with reference to the following, detailed description when taken in conjunction with the accompanying figures, wherein.

DETAILED DESCRIPTION

The present invention provides clinical decision support that can be used with non-portable and portable systems when delivering and/or monitoring delivery of a therapeutic gas comprising nitric oxide to a patient. Further, clinical decision support can be used with non-portable and portable systems during delivery and/or monitoring of delivery of therapeutic gas when nebulized drugs may and/or may not be being delivered to a patient (e.g., when nebulizers may be delivered in the inspiratory limb of the breathing circuit, when nebulizers may be delivered into a breathing gas delivery system, etc.).

Figure 1A:
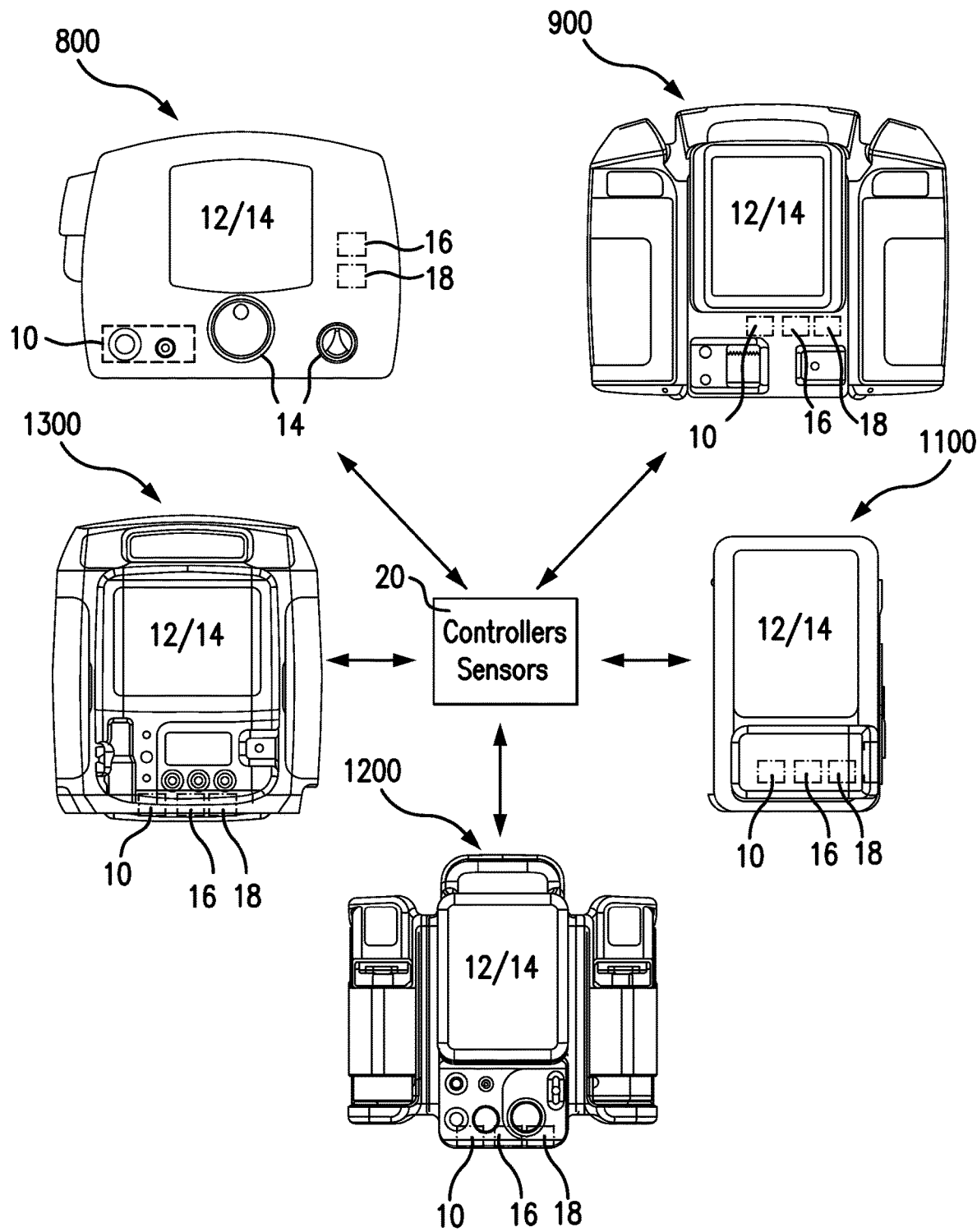
FIG. 1A depicts a block diagram of exemplary elements of certain embodiments of the present invention.

Referring to FIG. 1A, in exemplary embodiments, therapeutic gas systems and/or control modules of therapeutic gas systems (e.g., 800, 900, 1100, 1300, etc.) can include, but is not limited to, at least one of a one or more communications port 10, a one or more graphical user interface 12, at least one or more user input 14, a one or more processor readable memory 16, and a one or more processor 18, and any other reasonable components for communicating and/or analyzing information. In some instances, graphical user interface 12 and the at least one user input 14 can be substantially the same. For example, graphical user interface 12 and the at least one user input 14 can be combined as a touch screen (e.g., a display that can detect the presence and location of a touch within the display area).

In exemplary embodiments, clinical decision support can be algorithms, software, and/or logic based information affiliated with control modules of therapeutic gas systems (e.g., 800, 900, 1100, 1300, etc.). Clinical decision support can receive information from sensors, provide information and/or options to users, and/or can control (e.g., turn on, turn off, actuate, etc.) elements affiliated with therapeutic gas system used to deliver a therapeutic gas. For example, clinical decision support can include algorithms, software, and/or logic based information that can be stored in processor readable memory 16 of control modules of therapeutic gas systems (e.g., 800, 900, 1100, 1300, etc.) and/or that can be accessed by processors 18 of control modules of therapeutic gas systems (e.g., 800, 900, 1100, 1300, etc.). Clinical decision support can display information in a graphical user interface 12 of control modules of therapeutic gas systems (e.g., 800, 900, 1100, 1300, etc.) to users pertaining to, amongst other things, the delivery and/or monitoring of delivery of therapeutic gas to a patient. Further, information affiliated with elements 20 (e.g., sensors, controller, etc.) can be communicated to communications port 10 of control modules of therapeutic gas systems (e.g., 800, 900, 1100, 1300, etc. and/or user input information (e.g., input by user interaction with a display in graphical user interface 12 of control modules of therapeutic gas systems (e.g., 800, 900, 1100, 1300, etc.) can be received, accessed, utilized, and/or modified by clinical decision support.

In exemplary embodiments, clinical decision support can substantially reduce risk to elements of a system that may be affected by nebulized drugs by substantially reducing fluid communication to a breathing circuit of at least some elements of the system and/or shutting off at least some elements of the system when nebulized drugs may be being introduced into the breathing circuit. Further, when nebulized drugs may be being introduced into the breathing circuit, clinical decision support can display at least some information in a graphical user interface of a system to users pertaining to, amongst other things, the delivery and/or monitoring of delivery of therapeutic gas to a patient.

Clinical decision support can be affiliated with a therapeutic gas system that can include, but is not limited to, a therapeutic gas supply comprising nitric oxide; a breathing gas delivery system that provides breathing gas to a patient; and/or a therapeutic gas delivery system. To allow for delivering and/or monitoring of delivery of therapeutic gas to a patient when drugs may be being delivered via a nebulizer clinical decision support affiliated with the therapeutic gas delivery system can include a nebulizer mode. Nebulizer mode can include algorithms, software, and/or logic based information affiliated with clinical decision support. Nebulizer mode can actuate (e.g., shut off, turn on, etc.) elements of the therapeutic gas system and/or restrict fluid communication between elements of the therapeutic gas system and a breathing circuit where nebulized drugs may be being delivered.

Nebulizer mode and/or clinical decision support can provide numerous benefits such as, but not limited to, providing reassurance to users (e.g., clinicians) that correct amount of therapeutic gas is, for example, being supplied to the patient even when drugs are delivered to the patient through nebulizers; increase the lifetime of components that may be damaged and/or interact with nebulized drugs; provide information to users that can be substantially easy to interpret; to name a few.

Clinical decision support can be used with non-portable and portable therapeutic gas systems. Portable systems can provide numerous benefits such as, but not limited to, being able to be used at home, in an ambulatory environment, and/or in an environment more conducive to a patient. Portable systems may also be substantial easy to transport. For example, the present invention can be designed to be substantially light to ease portability and/or can use cylinders containing therapeutic gas that can be smaller than cylinders typically used as a therapeutic gas supply.

Therapeutic gas can include, but is not limited to, nitric oxide in a carrier gas such nitrogen. Suitable therapeutic gases can have varying concentrations of nitric oxide, and exemplary concentrations of nitric oxide in the therapeutic gas include, but are not limited to, 100 ppm to 10,000 ppm. In exemplary embodiments, the concentration of nitric oxide can be about 800 ppm. Of course, other concentrations are within the scope of the invention.

In exemplary embodiments, systems of the present invention can include a control circuit and a display that can measure the flow of therapeutic gas and/or breathing gas to, for example, determine and/or display a calculated dose of nitric oxide. Further, in exemplary embodiments, systems of the present invention can include a control circuit and a display that can measure the flow of therapeutic gas and/or breathing gas to, for example, determine and/or display a calculated dose of nitric oxide when drugs are delivered via a nebulizer to a patient.

In exemplary embodiments, methods of the present invention can include monitoring the delivery of therapeutic gas comprising nitric oxide to a patient. Further, in exemplary embodiments, methods of the present invention can include monitoring the delivery of therapeutic gas comprising nitric oxide to a patient when drugs are delivered via a nebulizer to a patient.

Systems and methods of the present invention can utilize and/or modify other gas delivery systems. For example, systems and methods of the present invention can utilize and/or modify gas delivery systems such that they can use clinical decision support and/or provide systems (e.g., portable systems, non-portable systems, etc.) capable of delivering and/or monitoring delivery of therapeutic gas to a patient. The present disclosure can utilize and/or modify the teachings of U.S. Pat. No. 5,558,083 filed Nov. 22, 1993, entitled "Nitric Oxide Delivery System", the content of which is incorporated herein in its entirety. Further, the present disclosure can utilize and/or modify the teachings of U.S. Pat. No. 8,291,904 filed Jun. 11, 1012, entitled "Gas Delivery Device and System" and U.S. Pat. Pub No.: 2013/0192595 filed Mar. 13, 2013, entitled "Apparatus and Method for Monitoring Nitric Oxide Delivery", the content of both of which at is incorporated herein by reference in their entireties and at least partially reproduced below.

In exemplary embodiments, clinical decision support can be affiliated with and/or utilized by various technologies and configurations of non-portable and/or portable systems for monitoring of delivery of a therapeutic gas to a patient, when nebulized drugs may and/or may not be being delivered to the patient. For example, in exemplary embodiments, monitoring of delivery of a therapeutic gas, when nebulized drugs may and/or may not be being delivered to the patient, systems of the present invention can include a first inlet for receiving a therapeutic gas supply comprising nitric oxide; a second inlet for receiving a breathing gas; a therapeutic gas injector module in fluid communication with the first inlet and the second inlet to provide a combined flow of therapeutic gas and breathing gas; an outlet in fluid communication with the therapeutic gas injector module for supplying the breathing gas and therapeutic gas to a patient; and a control circuit to determine a calculated dose of nitric oxide based on the measured flow of breathing gas and the measured flow of therapeutic gas or a known flow of therapeutic gas.

For another example, in exemplary embodiments, monitoring of delivery of a therapeutic gas, when nebulized drugs may and/or may not be being delivered to the patient, systems of the present invention can include a first inlet to be placed in fluid communication with a therapeutic gas supply comprising nitric oxide; a second inlet to be placed in fluid communication with a breathing gas delivery system that provides a breathing gas to the patient; a therapeutic gas injector module in fluid communication with the first inlet and the second inlet to provide a combined flow of therapeutic gas and breathing gas; an outlet in fluid communication with the therapeutic gas injector module and configured to supply breathing gas and therapeutic gas to a patient; a control circuit including a first flow sensor to measure the flow of breathing gas from the breathing gas delivery system and a second flow sensor to measure flow of therapeutic gas. Further, the control circuit can determine a calculated dose of nitric oxide based on the measured flow of breathing gas and the measured flow of therapeutic gas. A display in communication with the control circuit can provide a visual and/or numeric indication of the calculated dose of nitric oxide. Instead of determining a calculated dose of nitric oxide based on a measured flow of therapeutic gas, the calculated dose may be based on a known or assumed flow of therapeutic gas. This known flow of therapeutic gas may be a constant flow of therapeutic gas, such as if the nitric oxide delivery system is, for example, in a backup mode.

Figure 1B:
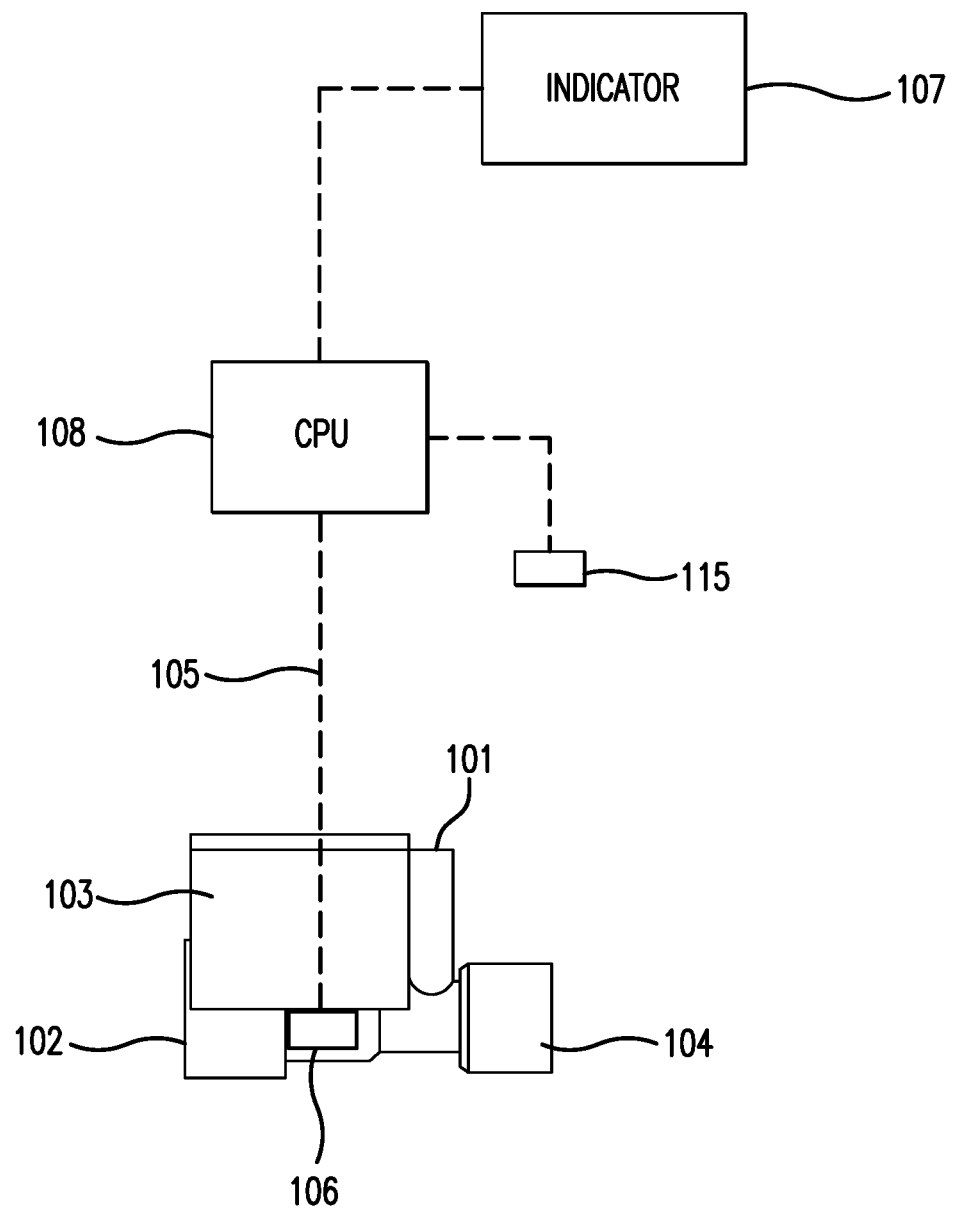
FIG. 1B depicts an exemplary system for monitoring patient inspired gas flow containing a therapeutic gas to a patient, in accordance with exemplary embodiments of the present invention.

Referring to FIG. 1, in accordance with exemplary embodiments of the present invention, an exemplary system for monitoring delivery of a therapeutic gas that may be affiliated with clinical decision support, when nebulized drugs may and/or may not be being delivered to the patient, is shown. This system can be and/or be affiliated with a non-portable system and/or portable system. The system can include, but is not limited to, a first inlet 101, second inlet 102, therapeutic injector module 103, outlet 104, control circuit 105, first flow sensor 106, indicator 107, CPU 108, second flow sensor 115, and/or any other reasonable component for the delivery and/or monitoring of delivery of a therapeutic gas.

First inlet 101 can be configured to be placed in fluid communication with a therapeutic gas comprising nitric oxide. Second inlet 102 can be configured to be placed in fluid communication with a breathing gas delivery system that provides a breathing gas to a patient. Therapeutic injector module 103 can be in fluid communication with first inlet 101 and second inlet 102, as well as outlet 104. The side view of therapeutic injector module 103 is shown. Outlet 104 can be in fluid communication with first inlet 101 and second inlet 102, and can be configured to supply breathing gas and therapeutic gas to a patient. A first flow sensor 106 can be in fluid communication and downstream of second inlet 102, and monitors the flow of breathing gas through therapeutic injector module 103. Control circuit 105 can be in communication with therapeutic injector module 103, and connects flow sensor 106 to CPU 108 and indicator 107. Control circuit 105 may also be in communication with a second flow sensor 115 that measures the flow of therapeutic gas into the therapeutic injector module 103. When the flow rate as measured by flow sensor 106 is, for example, above or below a predetermined level, central processing unit (CPU) 108 may send a signal to indicator 107. The CPU 108 may also determine a calculated dose of nitric oxide based on the measured flow rate of therapeutic gas from flow sensor 115, the measured flow rate of breathing gas from flow sensor 106, and the concentration of nitric oxide in the therapeutic gas. Alternatively, the CPU 108 may use a known flow rate of therapeutic gas to determine the calculated dose. Indicator 107 can inform a user of the system that the flow can be outside of a particular range. The indicator 107 may be part of a display, such as an icon or graphic on a display screen.

Flow sensors 106 and 115 can be any appropriate flow measuring device. This includes, but is not limited to, a pneumotach, hot wire anemometer, thermal flow sensor, variable orifice, thermal time-of-flight, rotating vane and the like. Also suitable are flow transducers that measure pressure, such as a pressure drop though an orifice, in order to determine flow. In at least one exemplary embodiment, flow sensor 106 can be part of the therapeutic injector module 103. In one such embodiment, the flow sensor 106 comprises a hot film sensor and a thermistor. The thermistor measures the temperature of the breathing gas flowing through the injector module 103. The constant temperature hot film sensor measures the flow of breathing gas in proportion to the energy required to maintain the platinum film temperature constant. In other embodiments, the flow sensor 106 can be upstream of the therapeutic injector module 103.

In exemplary embodiments, flow sensor 115 can be part of the therapeutic injector module. In exemplary embodiments, flow sensor 115 can be upstream of the therapeutic injector module 103, such as in the control module of the nitric oxide delivery device.

The term "control circuit" encompasses a variety of ways that may be utilized to carry out various signal processing functions to operate the therapeutic gas delivery system. In exemplary embodiments, the control circuit includes a CPU 108 and a flow controller. The CPU 108 can send and receive signals to the flow sensor 103 and the flow controller (not shown) such that the control circuit maintains set NO dose of therapeutic gas to the patient. In at least one exemplary embodiment, the CPU can obtain information from the flow sensor and from an input device that can allow the user to select the desired dose of nitric oxide.

In at least one exemplary embodiment of a control circuit, the flow sensor 103 can be in communication with a CPU 108 that can monitor the flow of each of the gases to patient, for example, as described herein. If a specific dose of nitric oxide is, for example, to be administered, the CPU 108 can calculate the necessary flow of therapeutic gas based on the measured flow of breathing gas and the concentration of nitric oxide in the therapeutic gas. Such a calculation can be performed using the following equation:

$$Q_{therapeutic} = [y_{set}/(y_{therapeutic} - y_{set})] * Q_{breathing}$$

wherein $Q_{breathing}$ represents the flow rate of breathing gas, $y_{set}$ represents the desired nitric oxide concentration, $y_{therapeutic}$ represents the concentration of nitric oxide in the therapeutic gas supply, and $Q_{therapeutic}$ represents the necessary flow of therapeutic gas to provide the desired concentration of nitric oxide in the gas mixture.

The central processing unit may be one of any forms of a computer processor that can be used in an industrial or medical setting for controlling various medical gas flow devices and sub-processors. The CPU can be coupled to a processor readable memory (not shown) and may be one or more of readily available processor readable memory such as random access memory (RAM), read only memory (ROM), flash memory, compact disc, floppy disk, hard disk, or any other form of local or remote digital storage. Support circuits (not shown) can be coupled to the CPU to support the CPU in a conventional manner. These circuits include cache, power supplies, clock circuits, input/output circuitry, subsystems, and the like. It will be understood that the control circuit, CPU, memory, and/or any of the above can be elements of control modules of therapeutic gas systems (e.g., 800, 900, 1100, 1300, etc.), for example, as depicted in FIG. 1A.

The control circuit may further include clinical decision support software. Such software may provide instructions for a variety of tasks, such as, but not limited to, providing alerts when the calculated dose of NO and/or the measured flow of breathing gas rises above or falls below a predetermined level. The predetermined level may be the level at which the system shuts down. Alternatively, the predetermined level may be a level that may be reached prior to system shutdown. Thus, for a system that shuts down when the delivered NO dose is, for example, below a minimum threshold, the predetermined level may be above this minimum threshold.

The predetermined level may be built into the clinical decision support software, and/or it may be provided by the user through an input device. In at least one exemplary embodiment, the clinical decision support software includes instructions to reset the upper and lower limits of maximum and minimum concentrations, dose errors or flows at which a shutdown can be triggered. In exemplary embodiments, the clinical decision software can include instructions to provide an alert when these limits are reached and/or avert the potential for shutdown of the system, which would lead to the lack of drug delivery. In exemplary embodiments, the system may comprise clinical decision software that provides instructions such that the system may automatically adjust these limits without the need for user intervention.

The clinical decision software may also include instructions to alter the time sensitivity of the system to changes in breathing gas flow and/or calculated dose. As a result, the system may change the time period necessary for a sustained low flow condition or under-delivery condition before the system shuts down. For example, the system can increase the time before shutdown from about 1 to 2 seconds to several seconds, so that a shutdown will only occur if the low flow and/or under-delivery is, for example, sustained for a longer period of time.

The system can include an indicator to inform a user when the calculated dose and/or flow of breathing gas rises above and/or falls below a predetermined level. In exemplary embodiments, the indicator provides an alert when the calculated dose and/or flow of breathing gas rises above and/or falls below the predetermined level. In exemplary embodiments, the alert includes one or more of an audible alert, a visual alert and a text alert. Such alerts can be provided at the location of the system itself, and/or may be provided at a remote location, such as directly to the medical staff or to a nursing station. When the alert is, for example, provided to a remote location, the signal may be transferred from the system to the remote location by any wired or wireless communication. Examples of alerts include, but are not limited to, text messages, sirens, sounds, alarms, flashing images, changes in display color, or any other means of attracting the attention of a user.

In exemplary embodiments, more than one alert may be provided. For example, a low priority alert may be provided when the flow of breathing gas falls below a first predetermined level, and a high priority alert may be provided when the flow of breathing gas falls below a second, lower predetermined level. Such a tiered alert system can put medical staff on notice of a relatively small deviation in flow rate, but also provide a more serious alert when a dangerous condition exists that requires immediate attention. A high priority alert can be provided when the flow rate is, for example, below the predetermined level for a certain period of time, thus indicating a sustained low flow condition.

The system can also include a display that provides a visual and/or numeric indication of the volumetric flow of breathing gas and/or the calculated dose. This visual and/or numeric indication can include any means of displaying the flow of breathing gas and/or calculated dose, including numerals, graphics, images or the like. The display can also be any sort of appropriate display device, including a dial, gauge or other analog device, or any electronic display device, including an LED, LCD, CRT, etc. Such device need not necessarily be connected to the system and may be utilized in a remote capacity. In certain embodiments, the visual and/or numeric indication of the breathing gas flow includes one or more of volumetric flow rate, tidal volume, and minute ventilation. The displayed flow rate may include one or more of the following: average flow rate, instantaneous flow rate, peak flow rate, minimum measured flow rate, or other like measurements relating to the breathing gas flow.

Figure 5A:
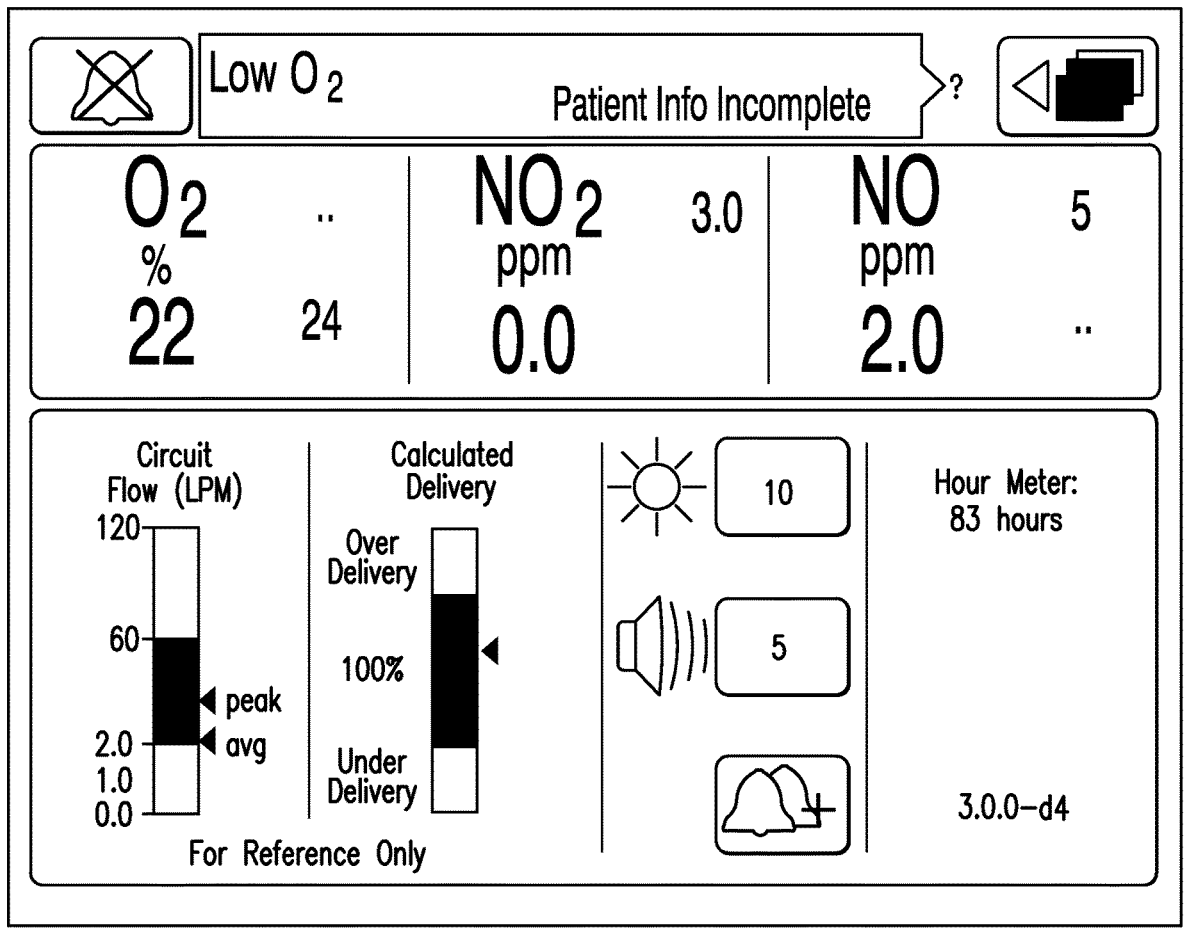
FIG. 5A depicts an exemplary screen displaying the flow of breathing and calculated NO dose delivered compared to set dose over a reporting time period of measured breathing gas flow rate gas, in accordance with exemplary embodiments of the present invention.
Figure 5B:
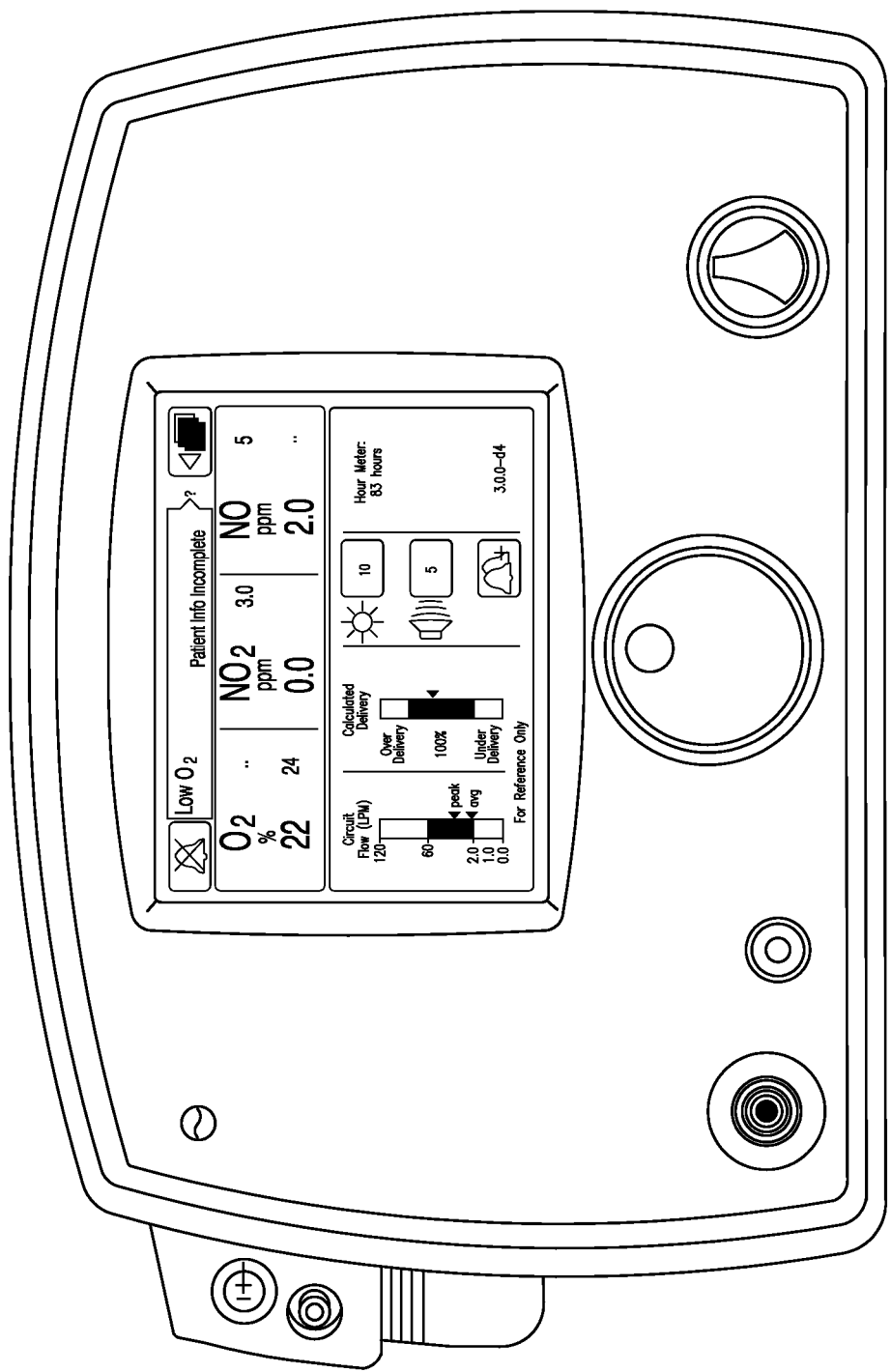
FIG. 5B depicts an exemplary screen affiliated with a non-portable device displaying the flow of breathing and calculated NO dose delivered compared to set dose over a reporting time period of measured breathing gas flow rate gas, in accordance with exemplary embodiments of the present invention.
Figure 5C:
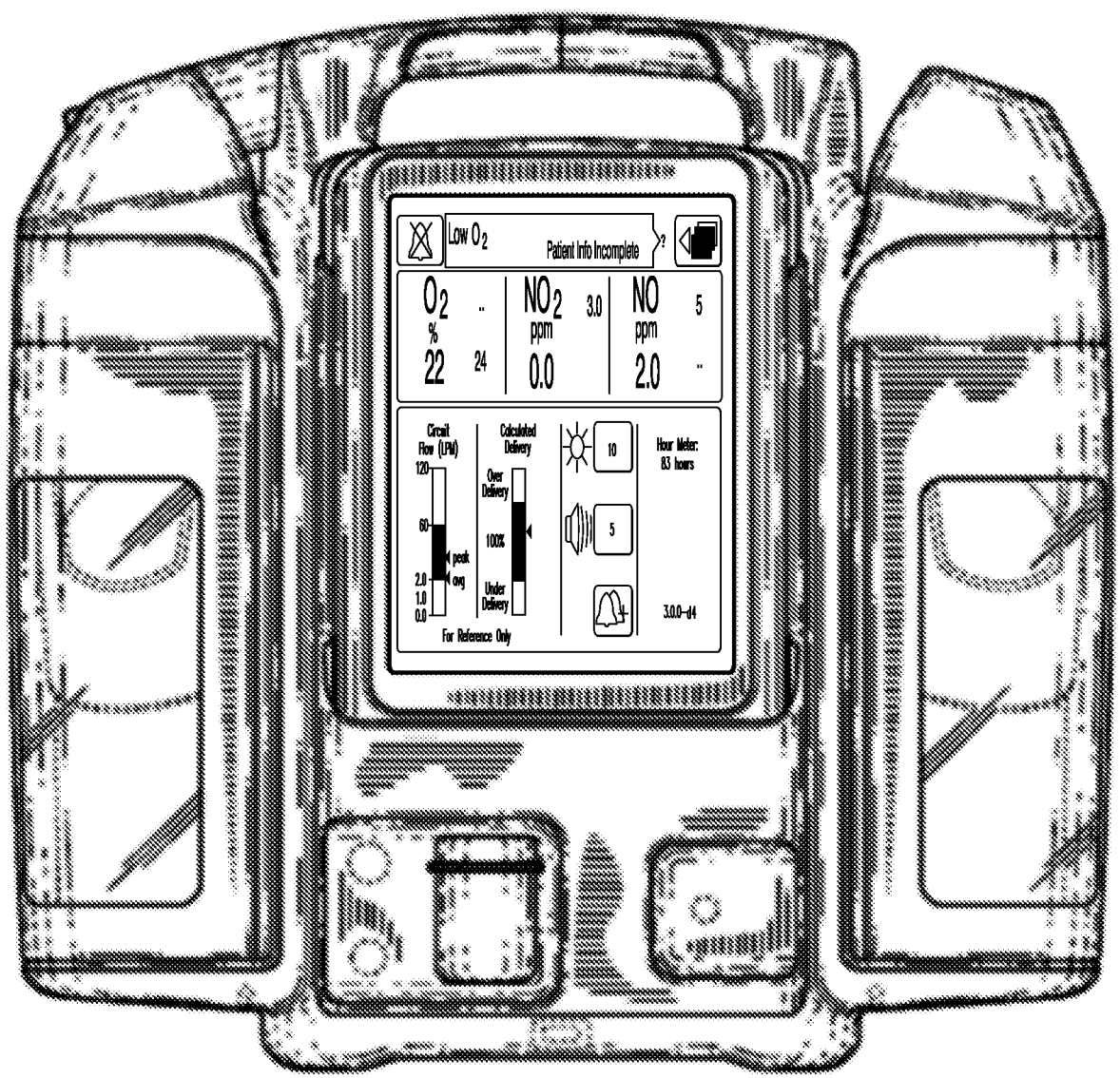
FIG. 5C depicts an exemplary screen affiliated with a portable device displaying the flow of breathing and calculated NO dose delivered compared to set dose over a reporting time period of measured breathing gas flow rate gas, in accordance with exemplary embodiments of the present invention.

Referring to FIGS. 5A-5C, an illustrative depiction shows exemplary screens displaying the flow of breathing gas. In exemplary embodiments, the screen can be display 208 discussed below with respect to FIG. 2 and/or any display affiliated a non-portable device (e.g., as illustrated in FIG. 5B) and/or any display affiliated with a portable device (e.g., as illustrated in FIG. 5C). The screen in FIGS. 5A-5C has an indicator in the bottom left corner showing the average and peak flow rates of breathing gas. In FIGS. 5A-5C, the indicator has a range of 0.0 to 120 standard liters per minute. The black region from 2.0 to 60 liters per minute can be the target range for the breathing gas, with 60 liters per minute as a high flow limit and 2.0 liters per minute as a low flow limit. The white regions above 60 liters per minute and below 2.0 liters per minute may be regions where delivery accuracy may differ from expected, when the set dose can be above 40 ppm, and/or where which an alarm may be emitted or other notification can be given to the user such that the user may be informed to make an appropriate correction to the respiratory device or the iNO delivery system. The low flow and high flow limits may be adjusted depending on the sensitivity of the flow sensor and/or injector module, or depending on the patient to be treated. As can be seen from FIGS. 5A-5C, the screen may also display other information, such as, but not limited to, the $O_2$, $NO_2$ and NO concentrations that are administered to the patient. In addition, the screen shown in FIGS. 5A-5C may also display other parameters relating to the breathing gas flow and nitric oxide delivery, such as the instantaneous breathing gas flow rate, minimum measured breathing gas flow rate, average nitric oxide dose rate, instantaneous nitric oxide dose rate, minimum and maximum nitric oxide dose rates, average nitric oxide flow rate, instantaneous nitric oxide flow rate, minimum and maximum nitric oxide flow rates, target nitric oxide delivery concentration, cylinder nitric oxide concentration, etc.

Figure 7A:
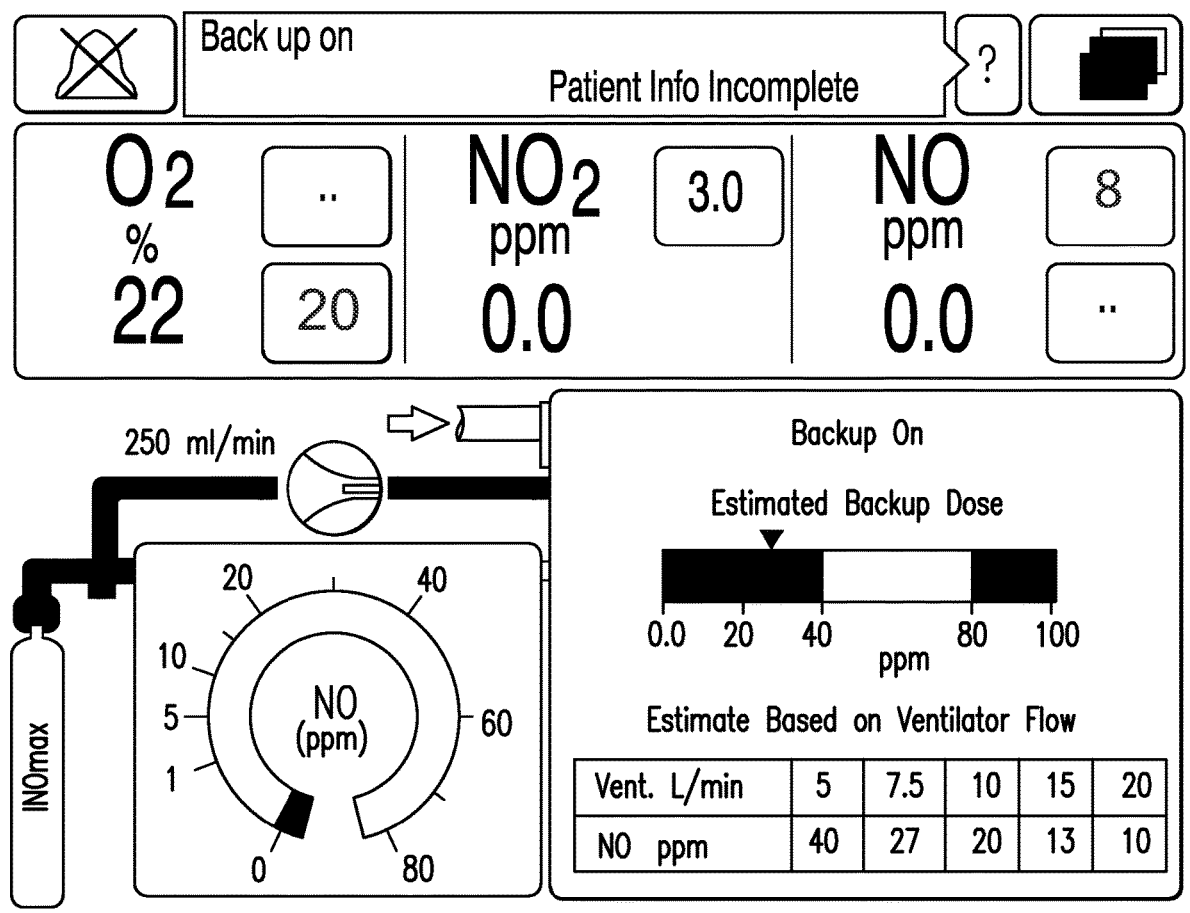
FIG. 7A depicts an exemplary screen displaying a calculated dose in ppm based on a known therapeutic gas flow rate and a measured breathing gas flow rate, in accordance with exemplary embodiments of the present invention.
Figure 7B:
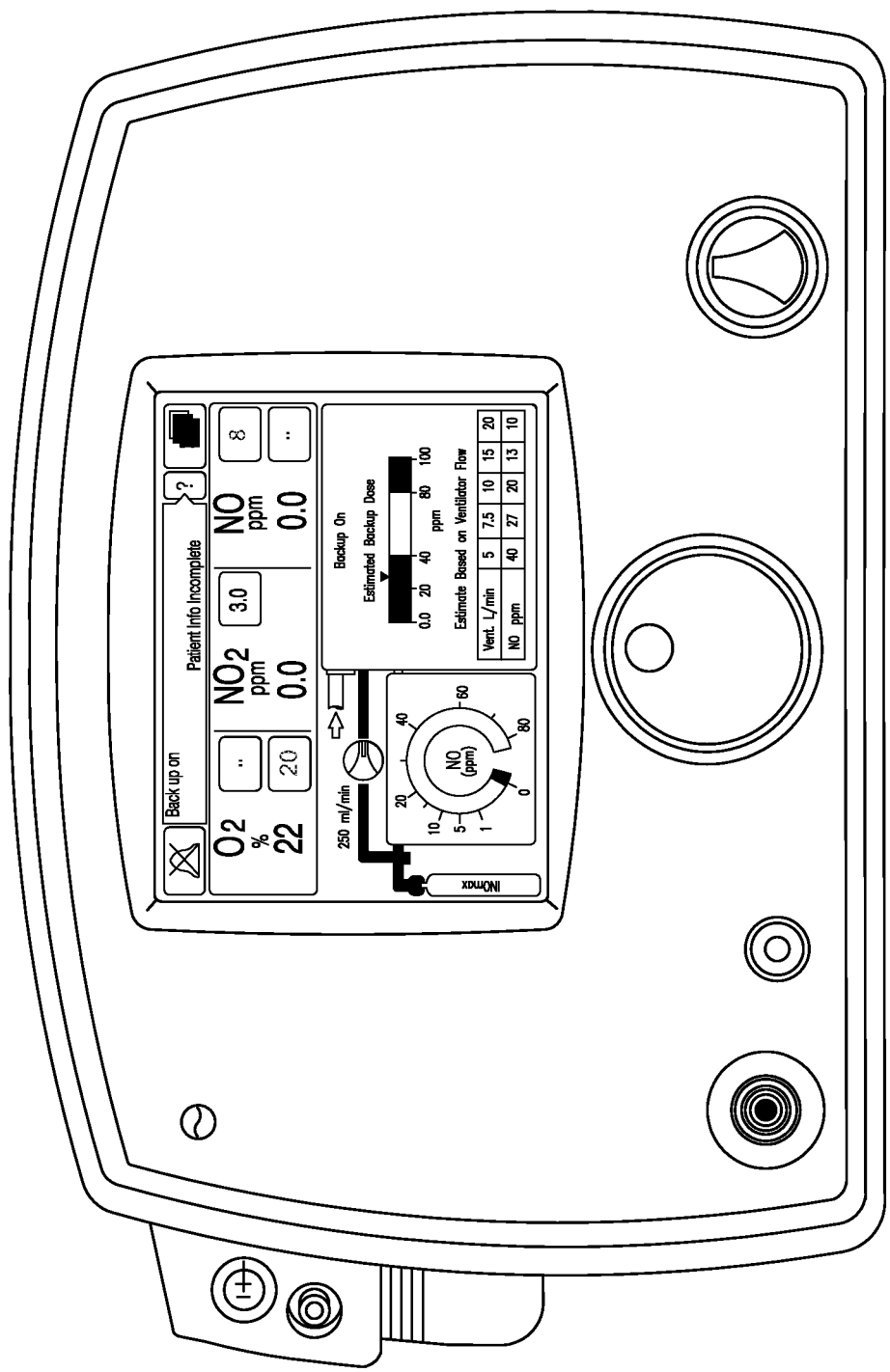
FIG. 7B depicts an exemplary screen affiliated with a non-portable device displaying a calculated dose in ppm based on a known therapeutic gas flow rate and a measured breathing gas flow rate, in accordance with exemplary embodiments of the present invention.
Figure 7C:
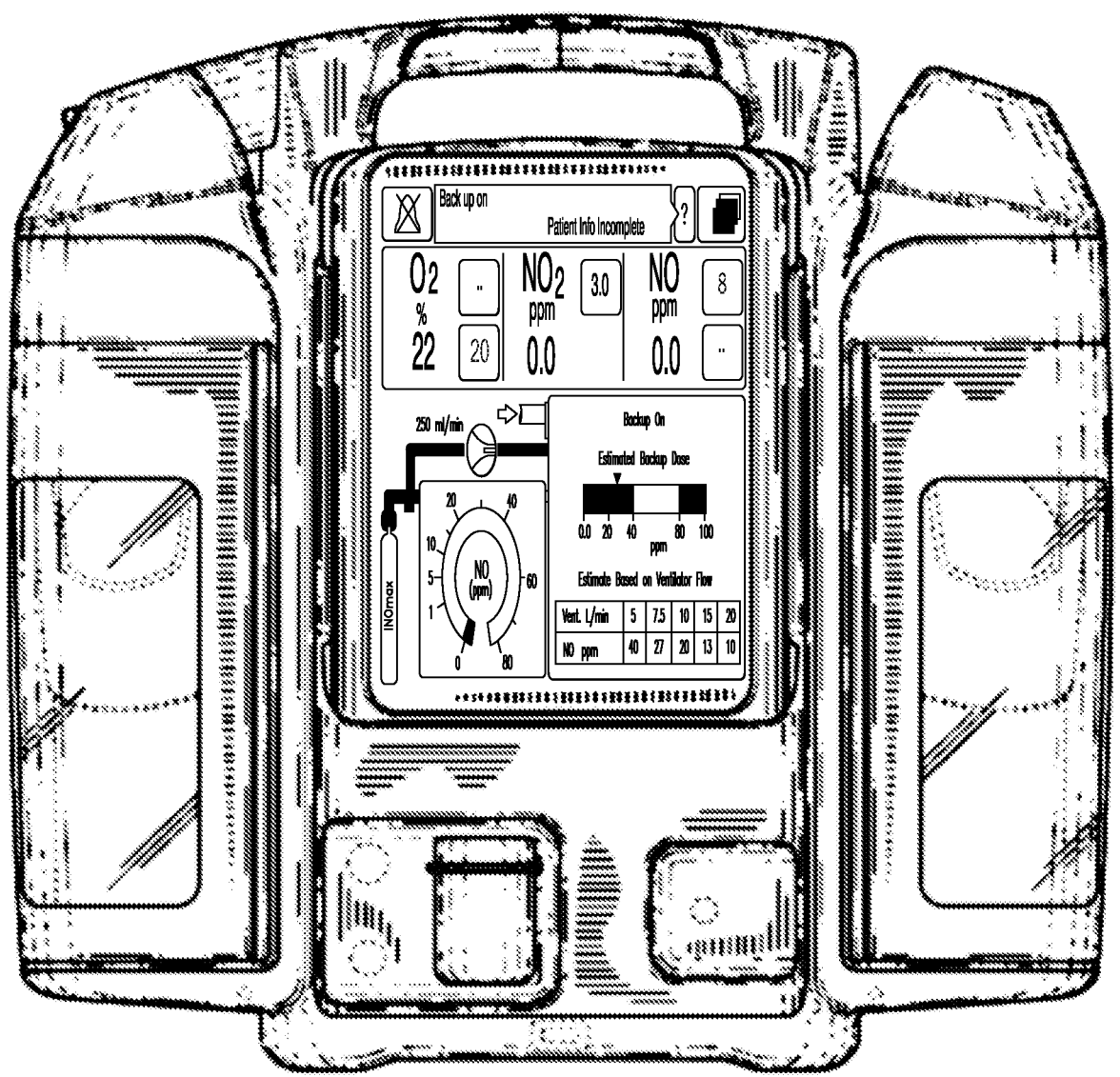
FIG. 7C depicts an exemplary screen affiliated with a portable device displaying a calculated dose in ppm based on a known therapeutic gas flow rate and a measured breathing gas flow rate, in accordance with exemplary embodiments of the present invention.
Figure 8A:
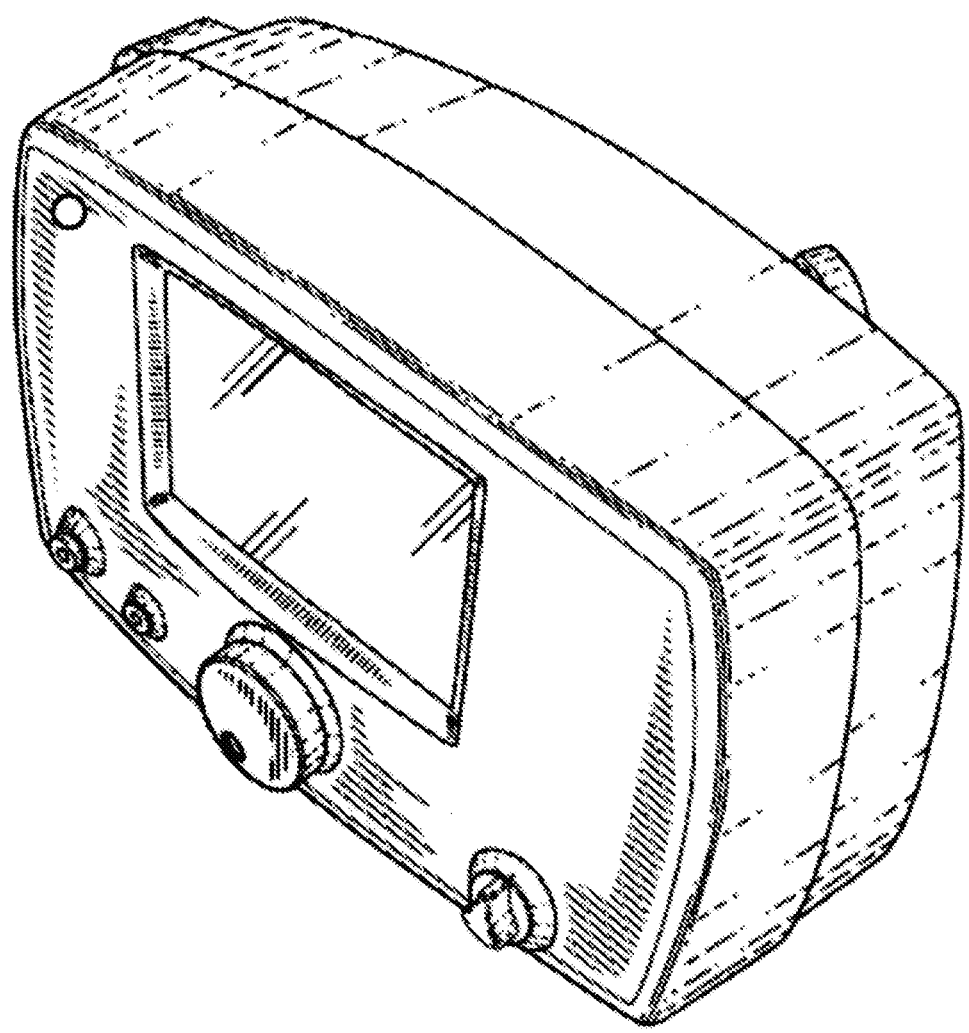
FIG. 8A is a top left front perspective view of an exemplary non-portable device, in accordance with exemplary embodiments of the present invention.
Figure 8B:
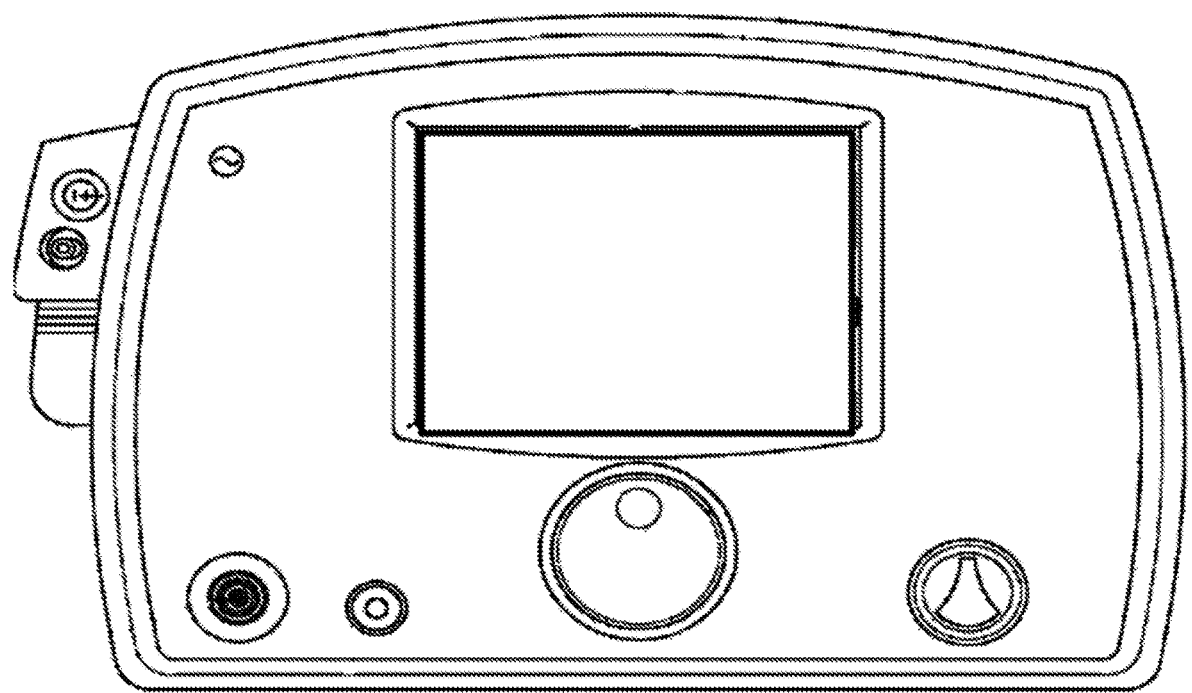
FIG. 8B is a front view of an exemplary non-portable device, in accordance with exemplary embodiments of the present invention.
Figure 8C:
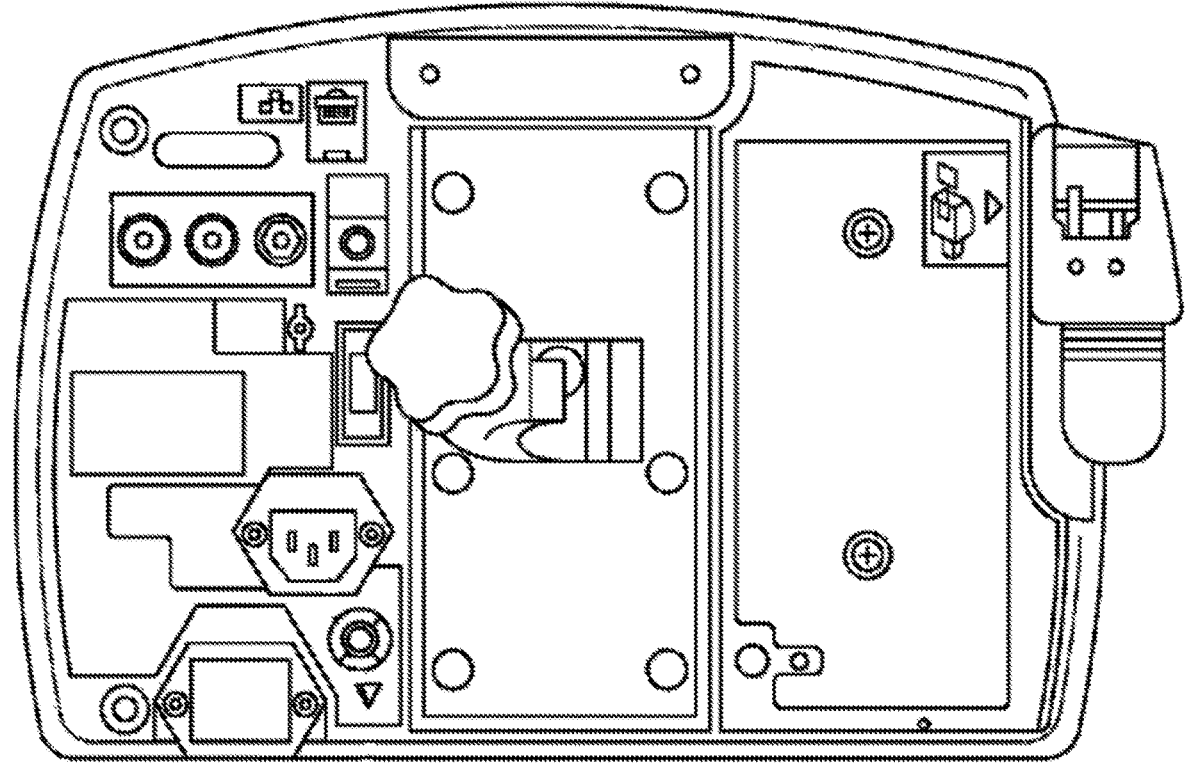
FIG. 8C is a back view of an exemplary non-portable device, in accordance with exemplary embodiments of the present invention.
Figure 8D:
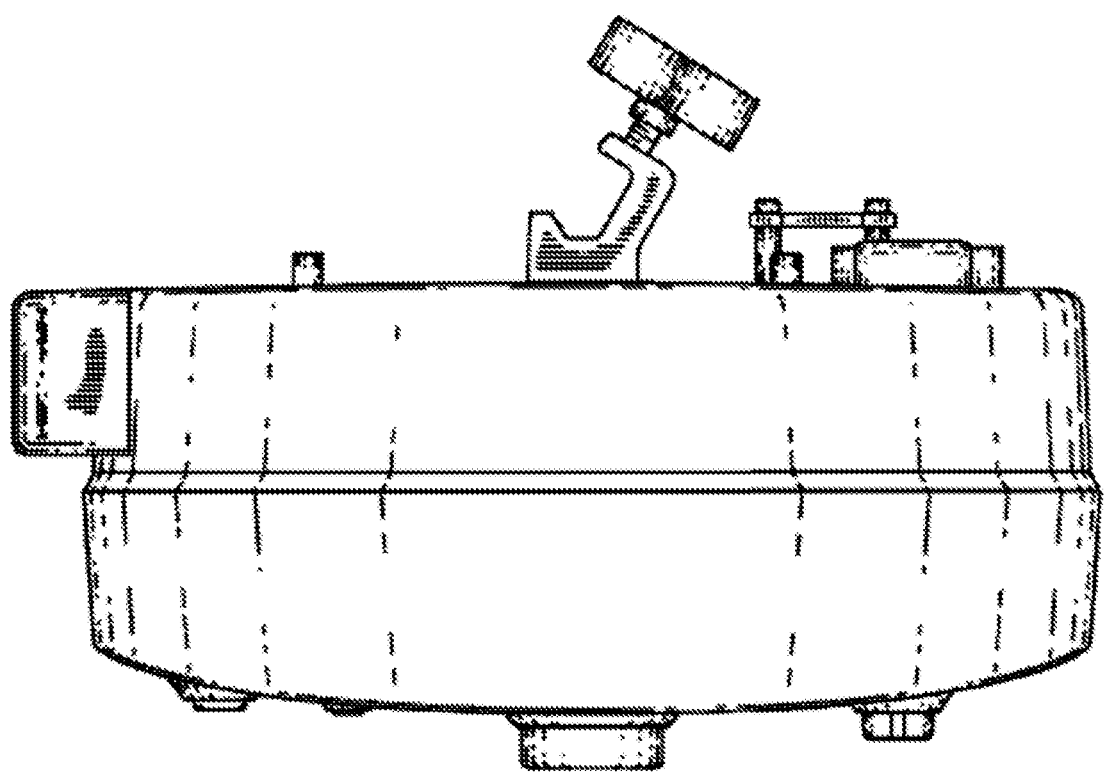
FIG. 8D is a top view of an exemplary non-portable device, in accordance with exemplary embodiments of the present invention.
Figure 8E:
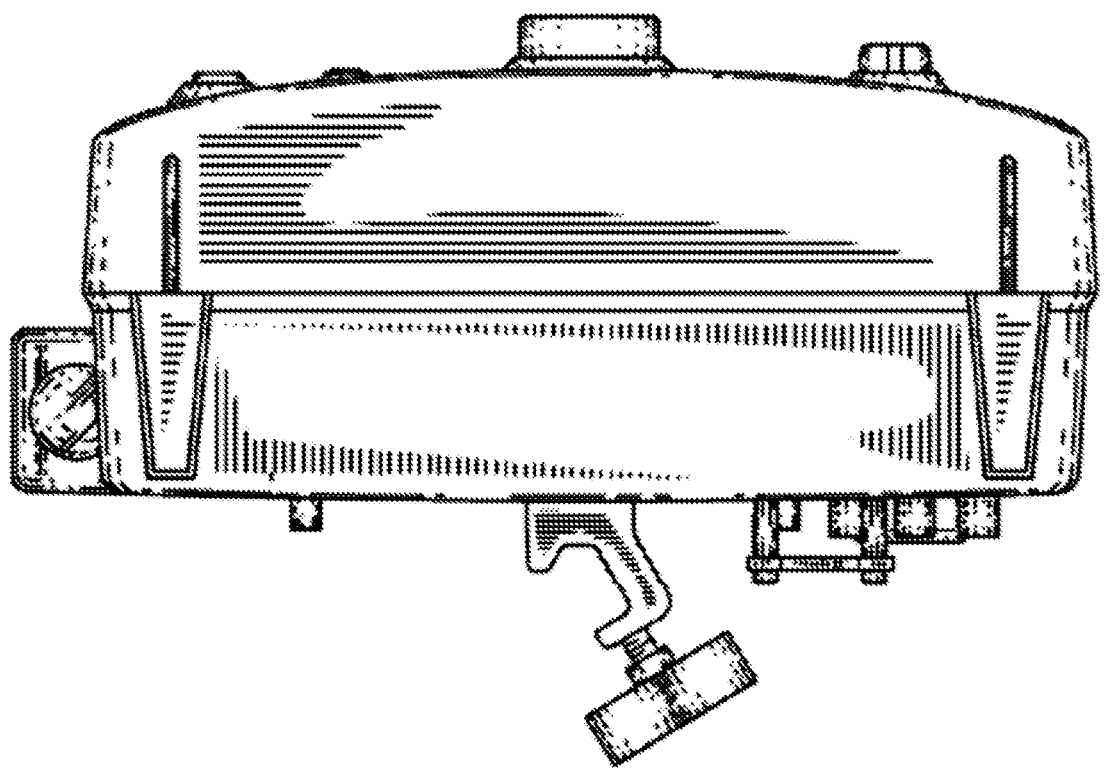
FIG. 8E is a bottom view of an exemplary non-portable device, in accordance with exemplary embodiments of the present invention.
Figure 8F:
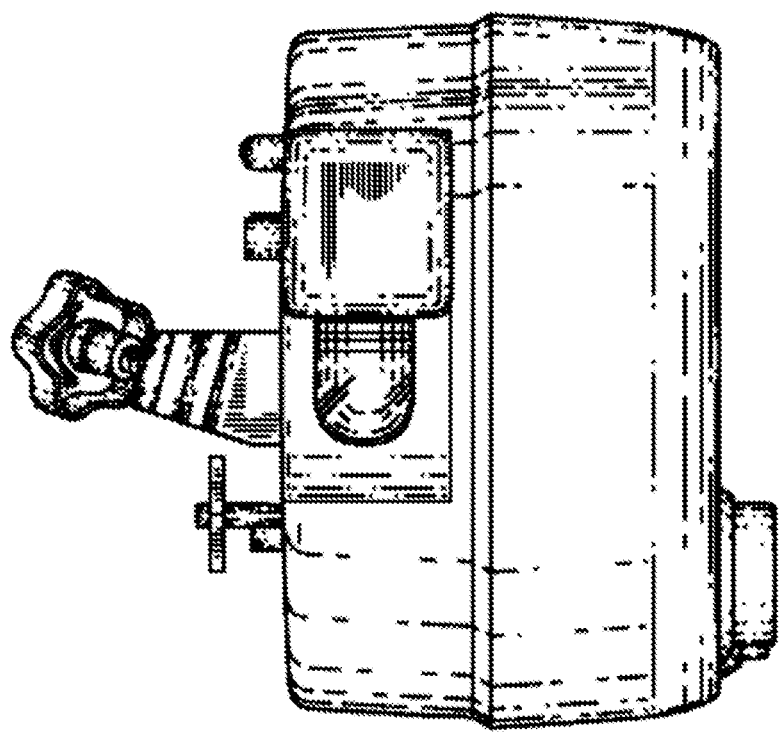
FIG. 8F is a first side view of an exemplary non-portable device, in accordance with exemplary embodiments of the present invention.
Figure 8G:
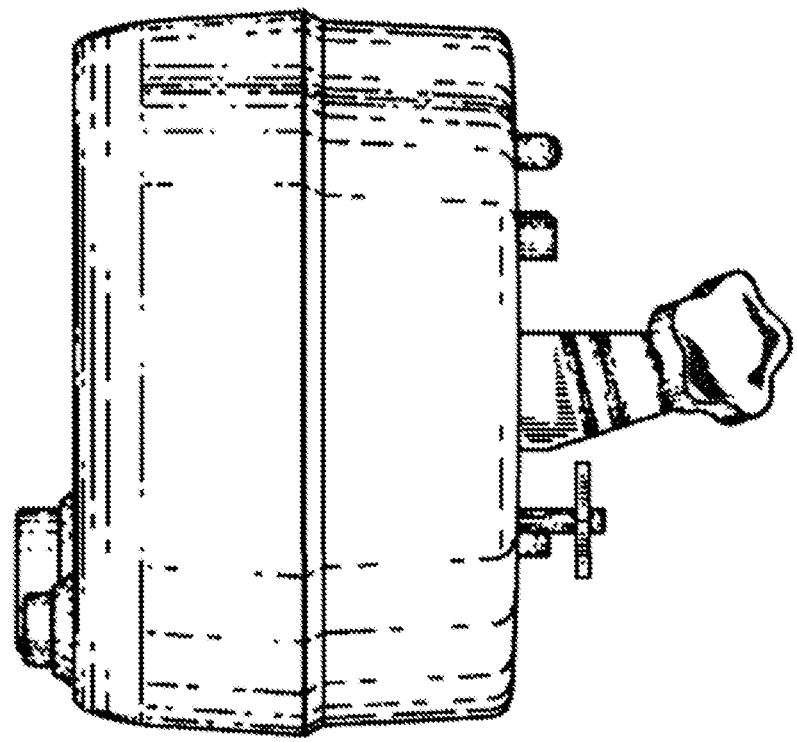
FIG. 8G is a second side view of an exemplary non-portable device, in accordance with exemplary embodiments of the present invention.
Figure 9A:
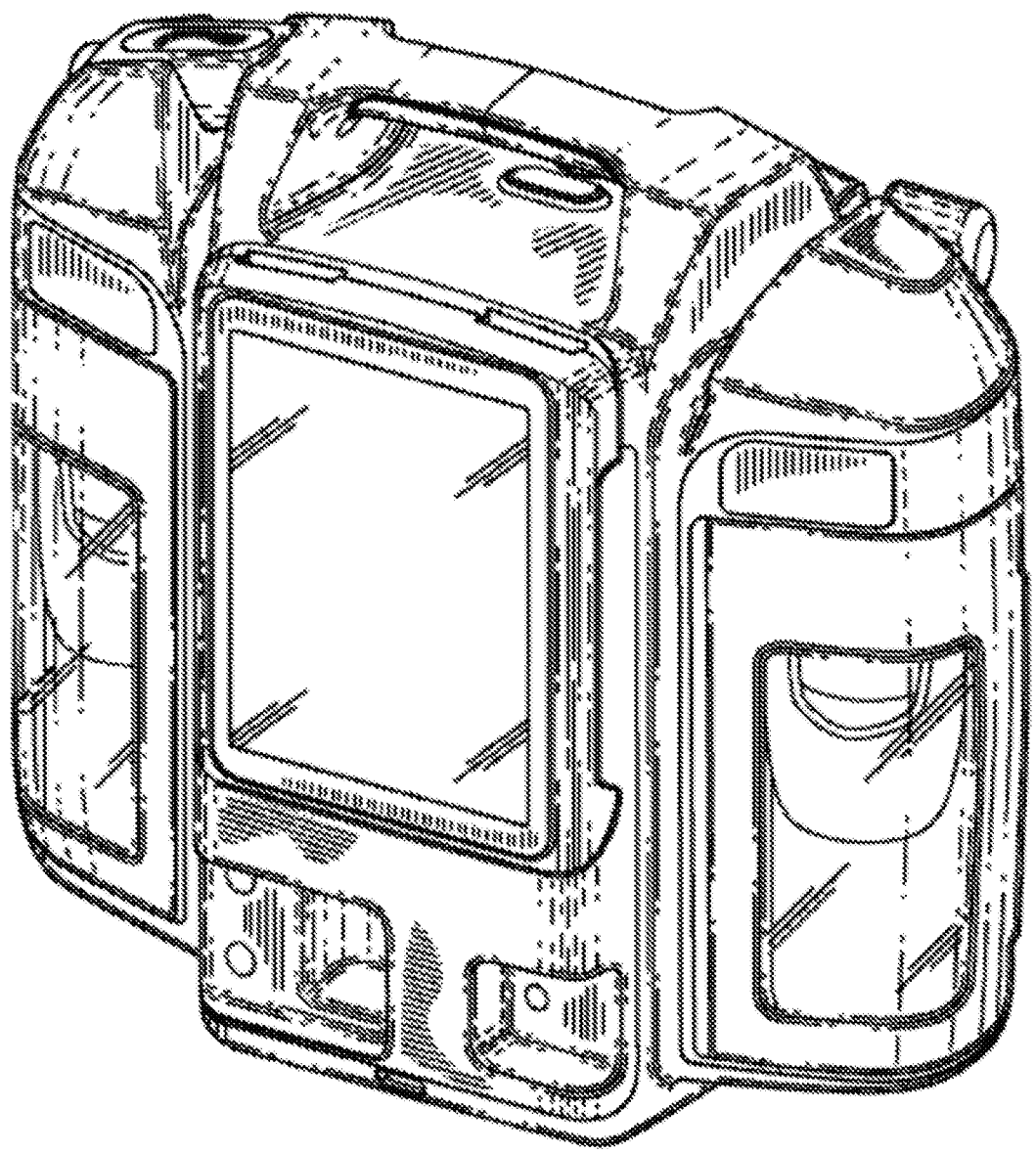
FIG. 9A is a top left front perspective view of an exemplary portable device, in accordance with exemplary embodiments of the present invention.
Figure 9B:
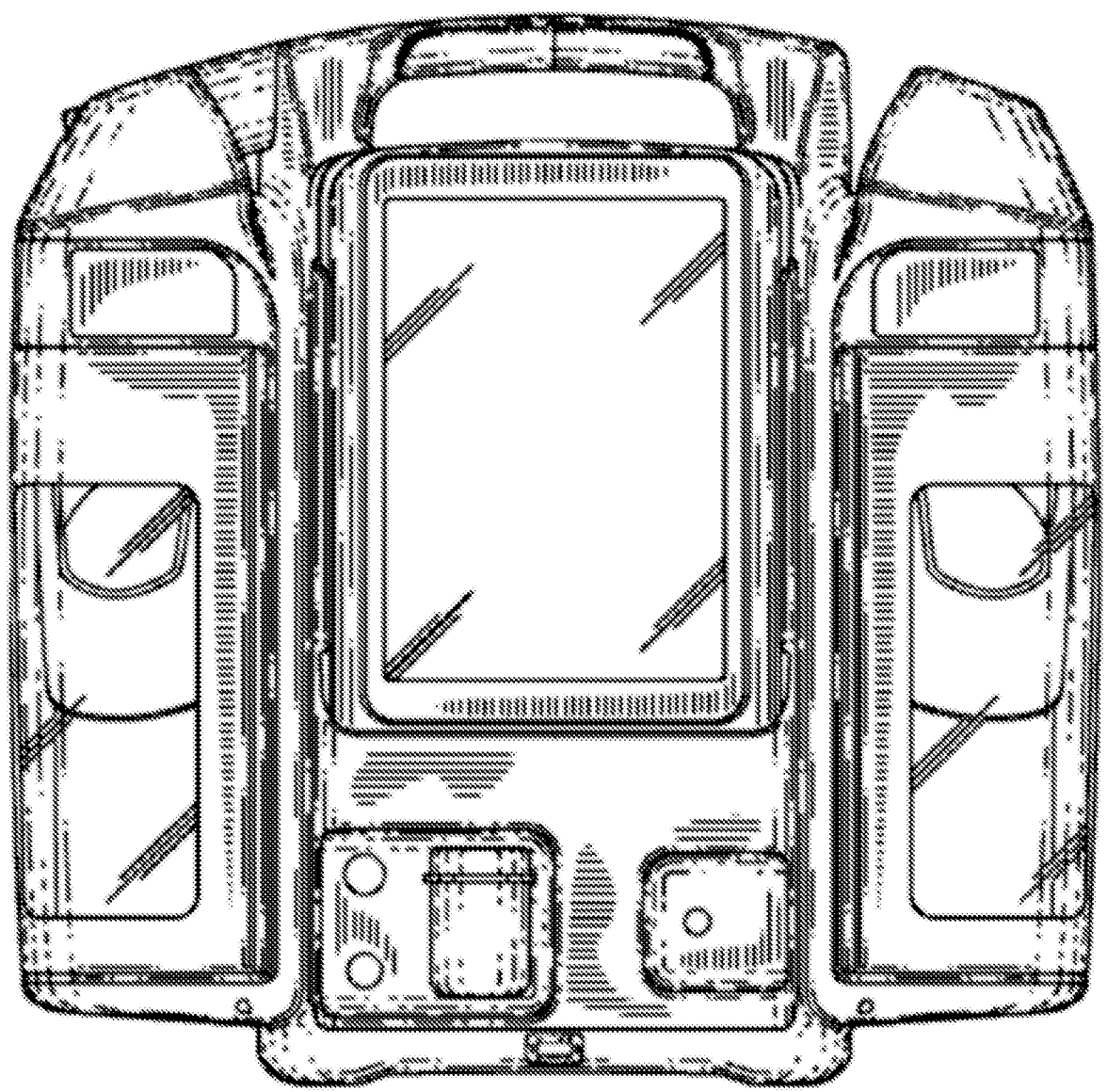
FIG. 9B is a front view of an exemplary portable device, in accordance with exemplary embodiments of the present invention.
Figure 9C:
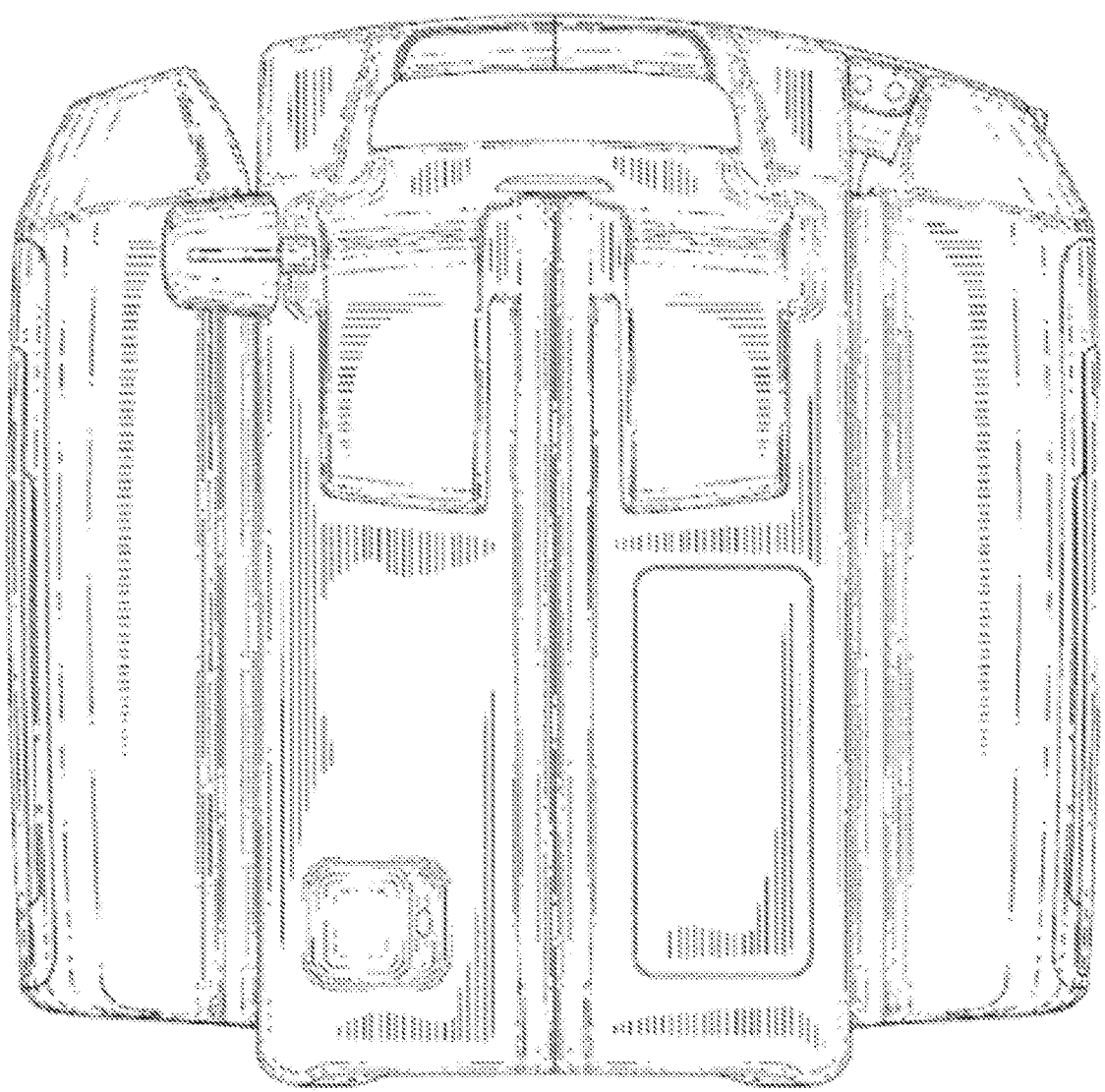
FIG. 9C is a back view of an exemplary portable device, in accordance with exemplary embodiments of the present invention.
Figure 9D:
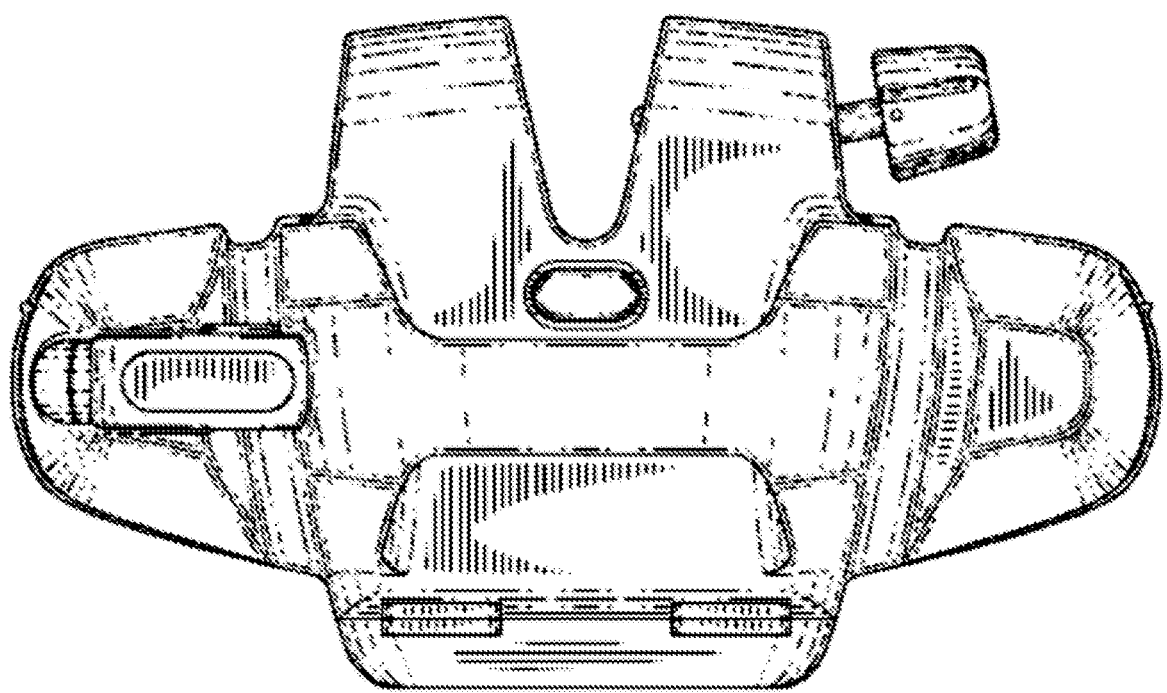
FIG. 9D is a top view of an exemplary portable device, in accordance with exemplary embodiments of the present invention.
Figure 9E:
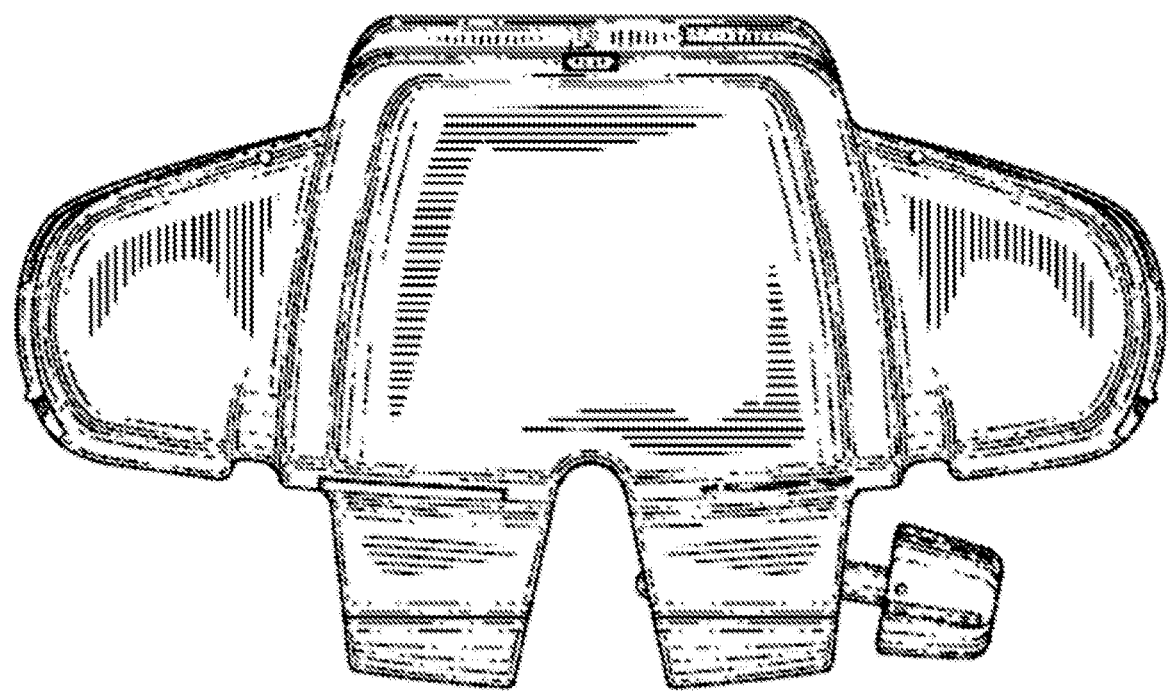
FIG. 9E is a bottom view of an exemplary portable device, in accordance with exemplary embodiments of the present invention.
Figure 9F:
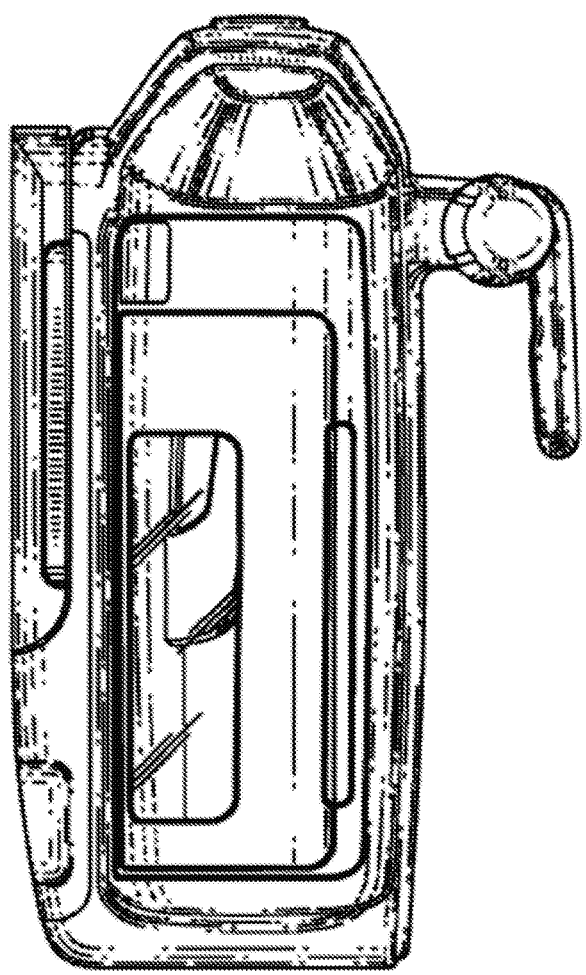
FIG. 9F is a first side view of an exemplary portable device, in accordance with exemplary embodiments of the present invention.
Figure 9G:
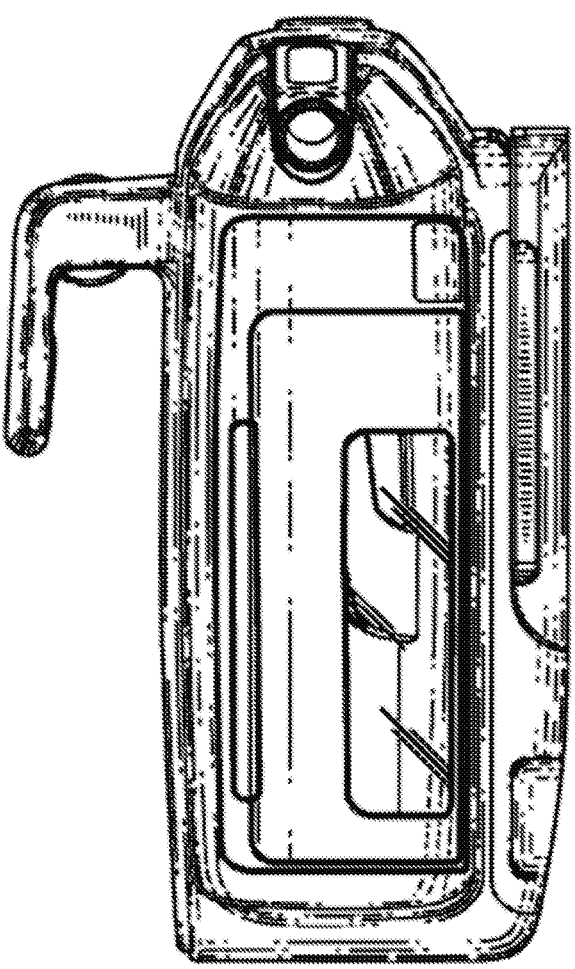
FIG. 9G is a second side view of an exemplary portable device, in accordance with exemplary embodiments of the present invention.
Figure 10A:
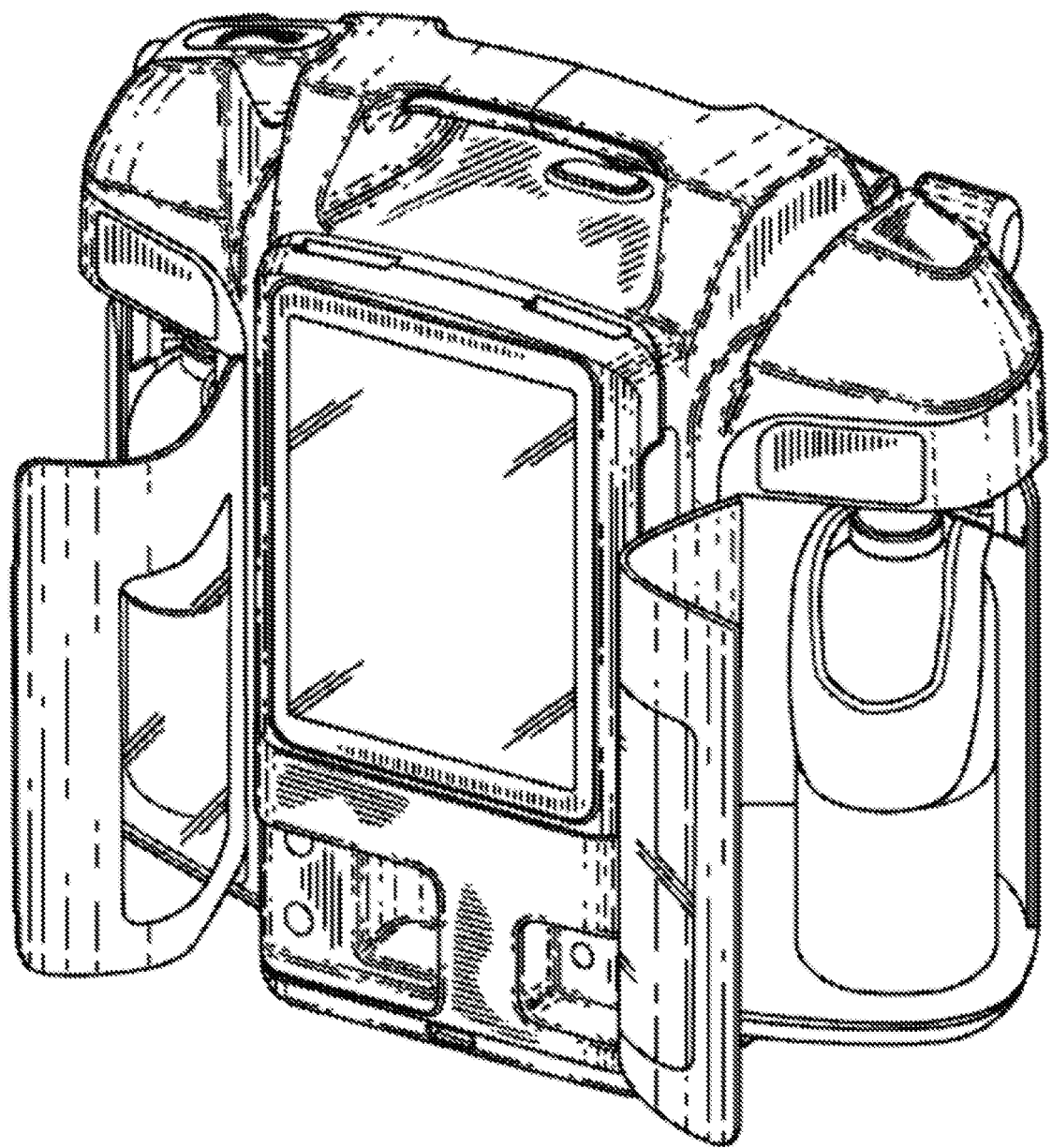
FIG. 10A is a top left front perspective view of an exemplary portable device, in accordance with exemplary embodiments of the present invention.
Figure 10B:
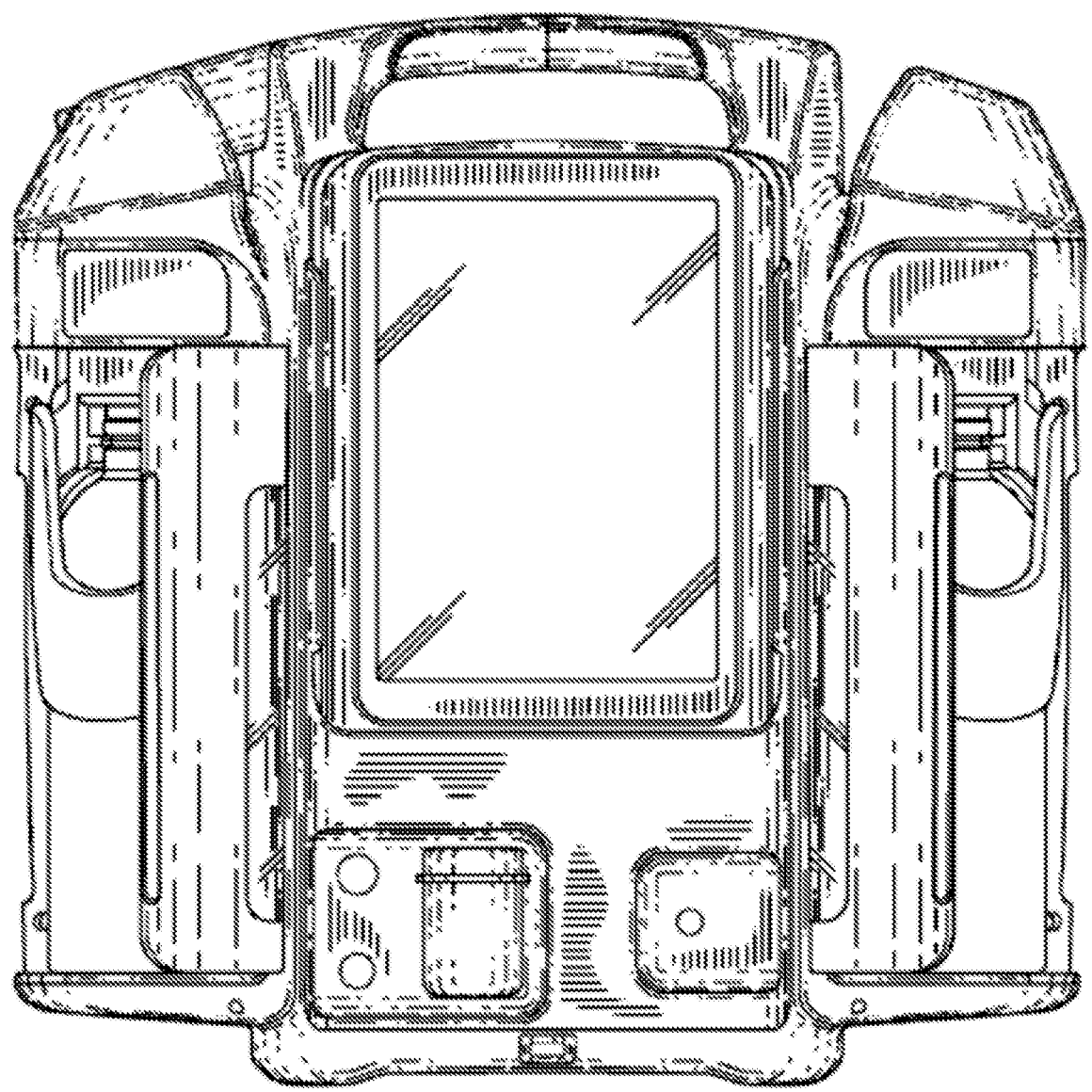
FIG. 10B is a front view of an exemplary portable device, in accordance with exemplary embodiments of the present invention.
Figure 10C:
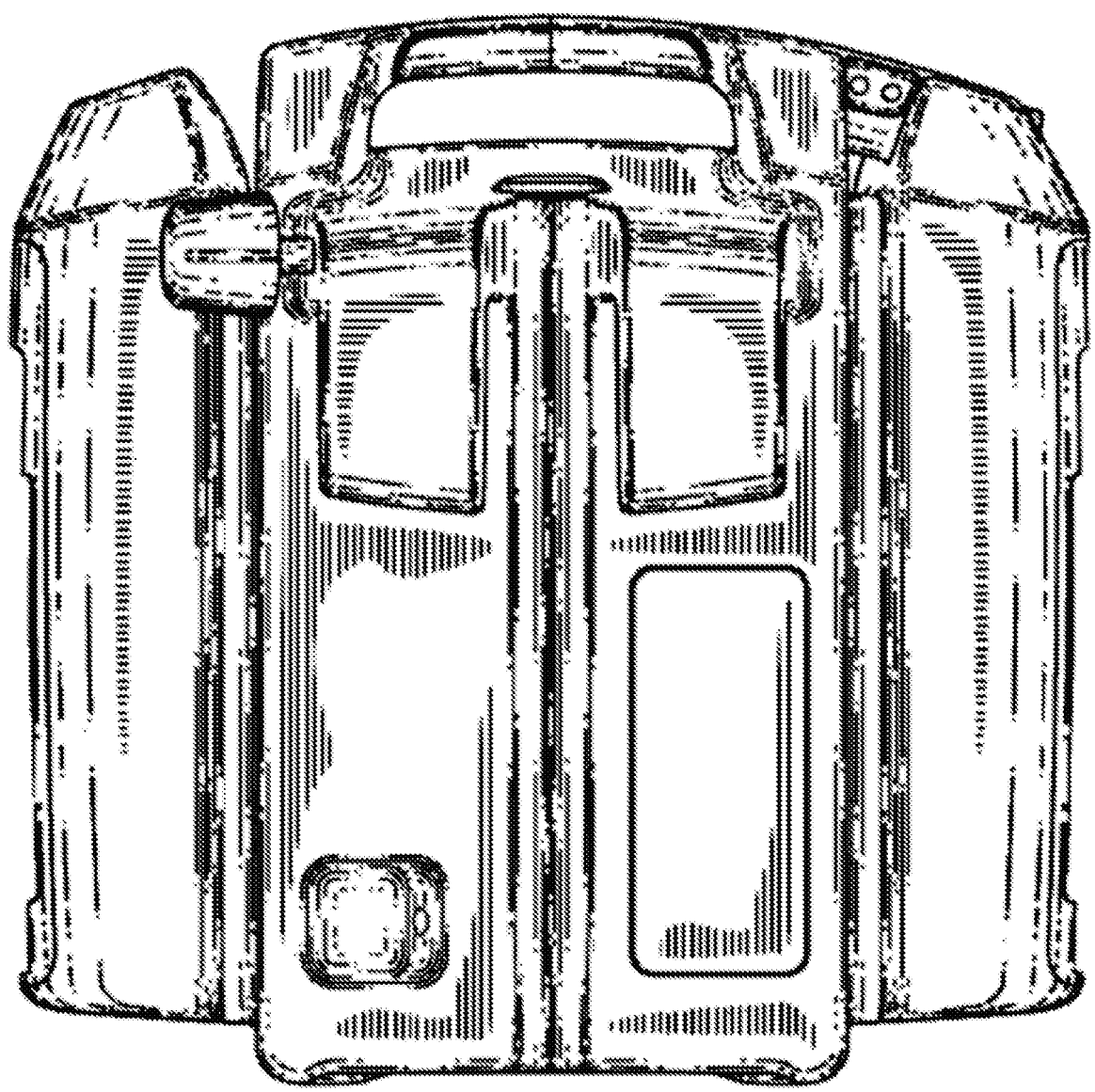
FIG. 10C is a back view of an exemplary portable device, in accordance with exemplary embodiments of the present invention.
Figure 10D:
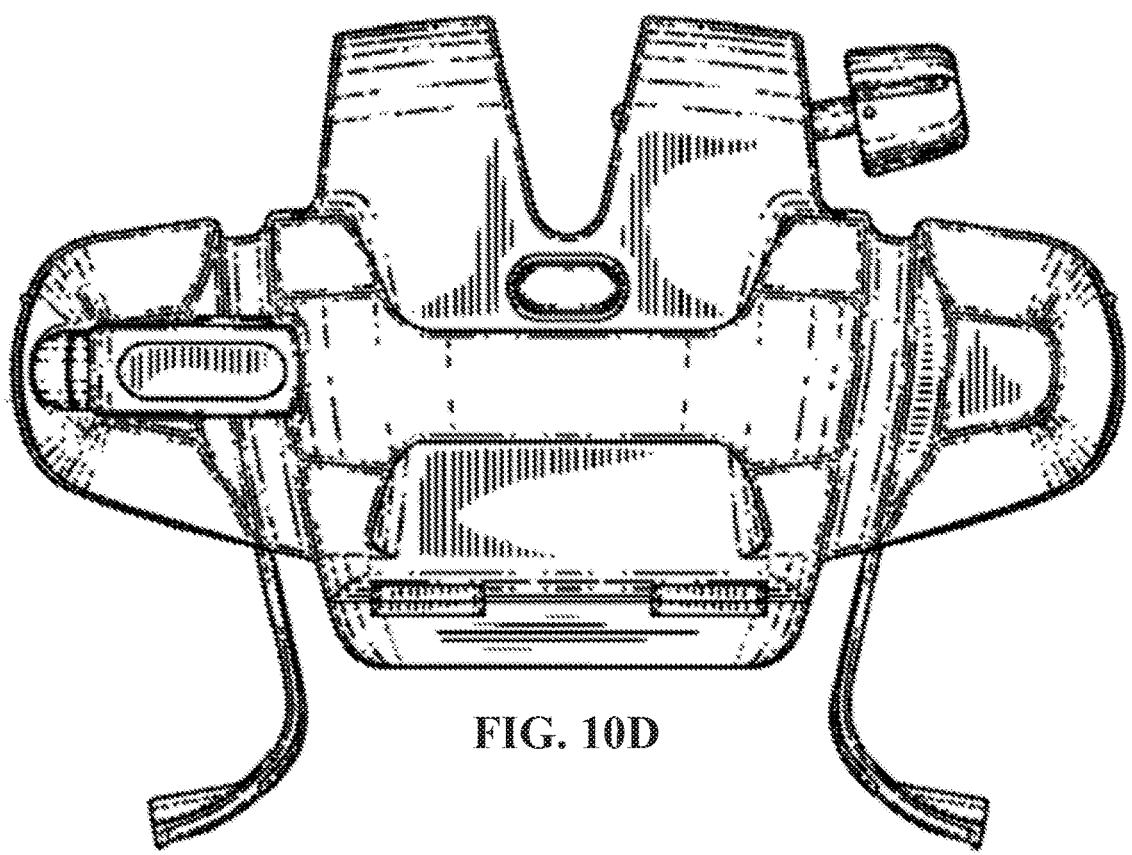
FIG. 10D is a top view of an exemplary portable device, in accordance with exemplary embodiments of the present invention.
Figure 10E:
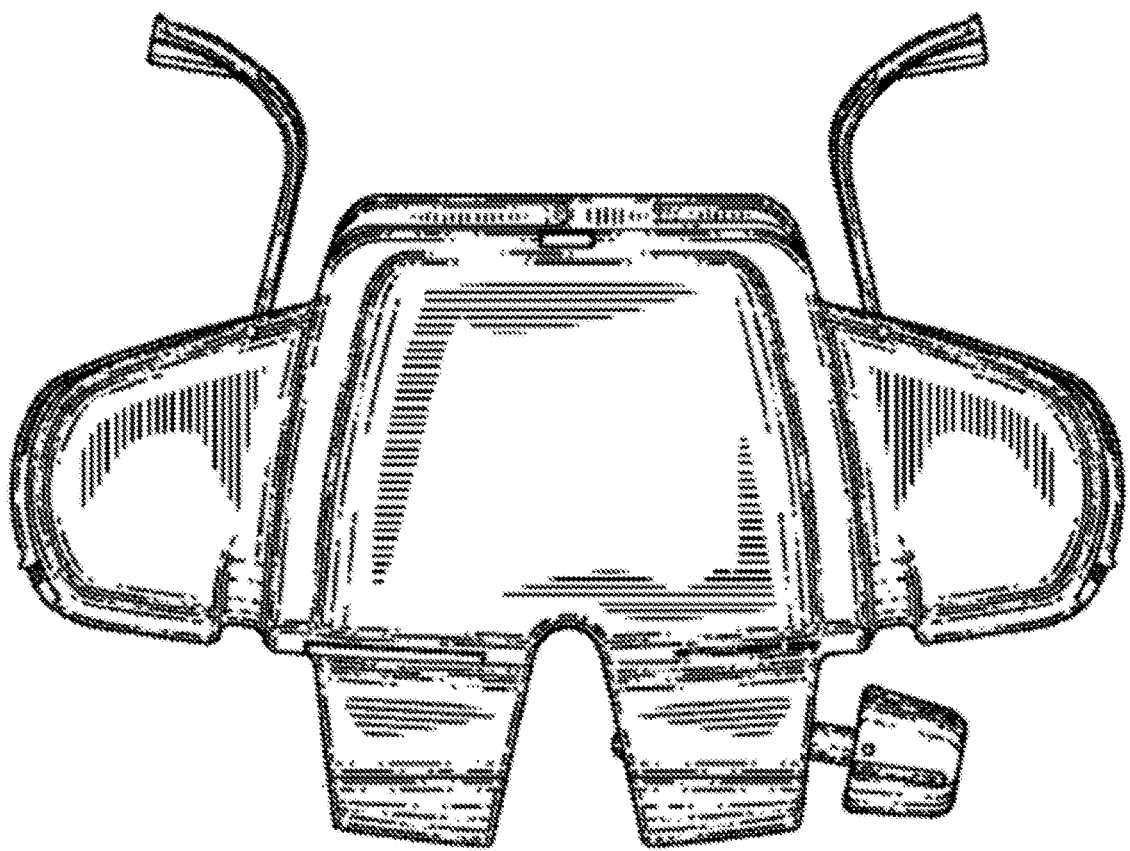
FIG. 10E is a bottom view of an exemplary portable device, in accordance with exemplary embodiments of the present invention.
Figure 10F:
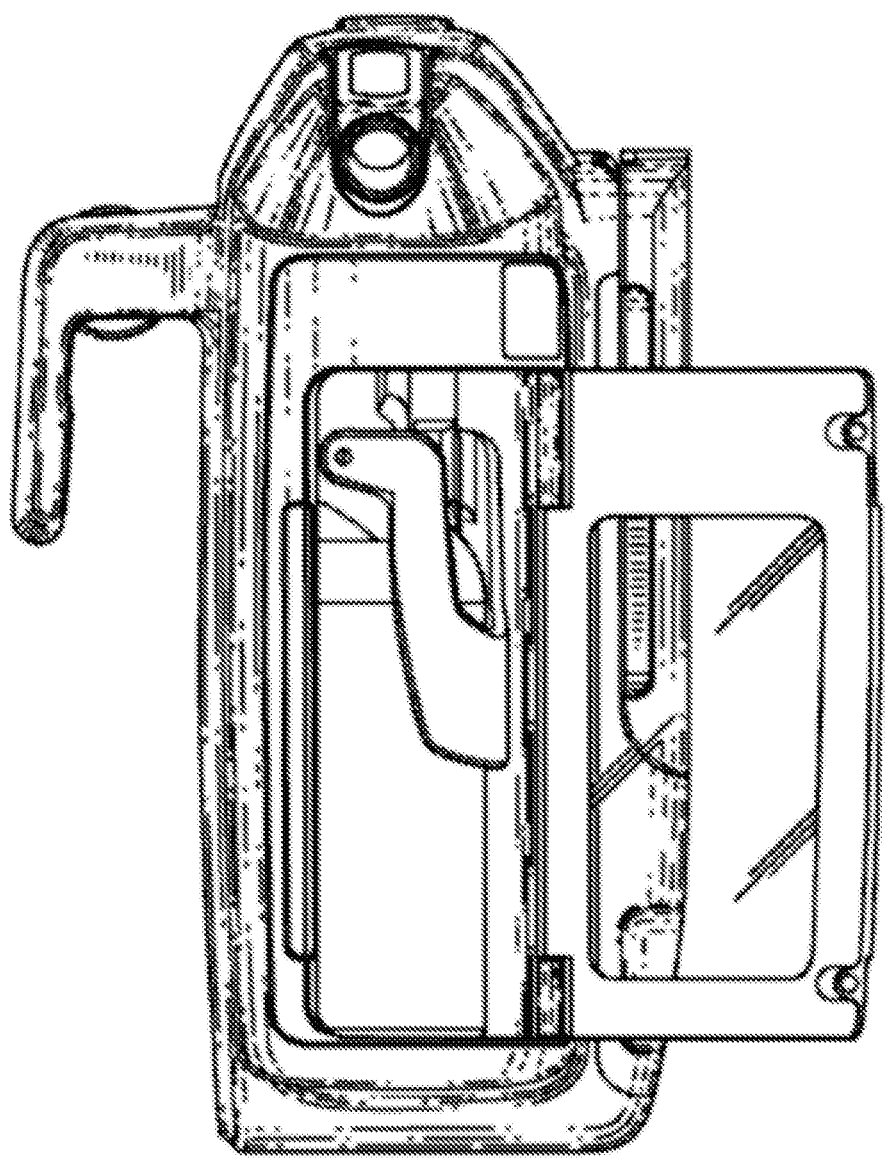
FIG. 10F is a first side view of an exemplary portable device, in accordance with exemplary embodiments of the present invention.
Figure 10G:
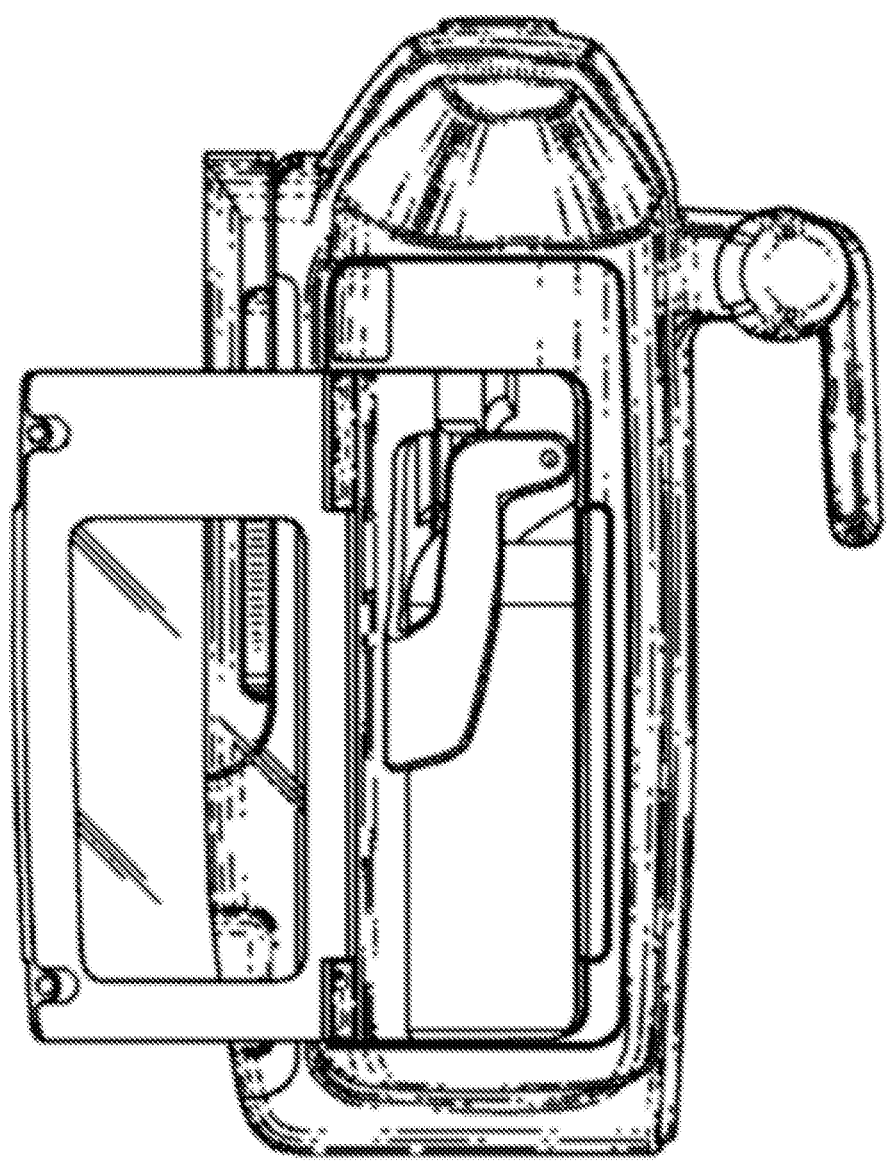
FIG. 10G is a second side view of an exemplary portable device, in accordance with exemplary embodiments of the present invention.
Figure 11A:
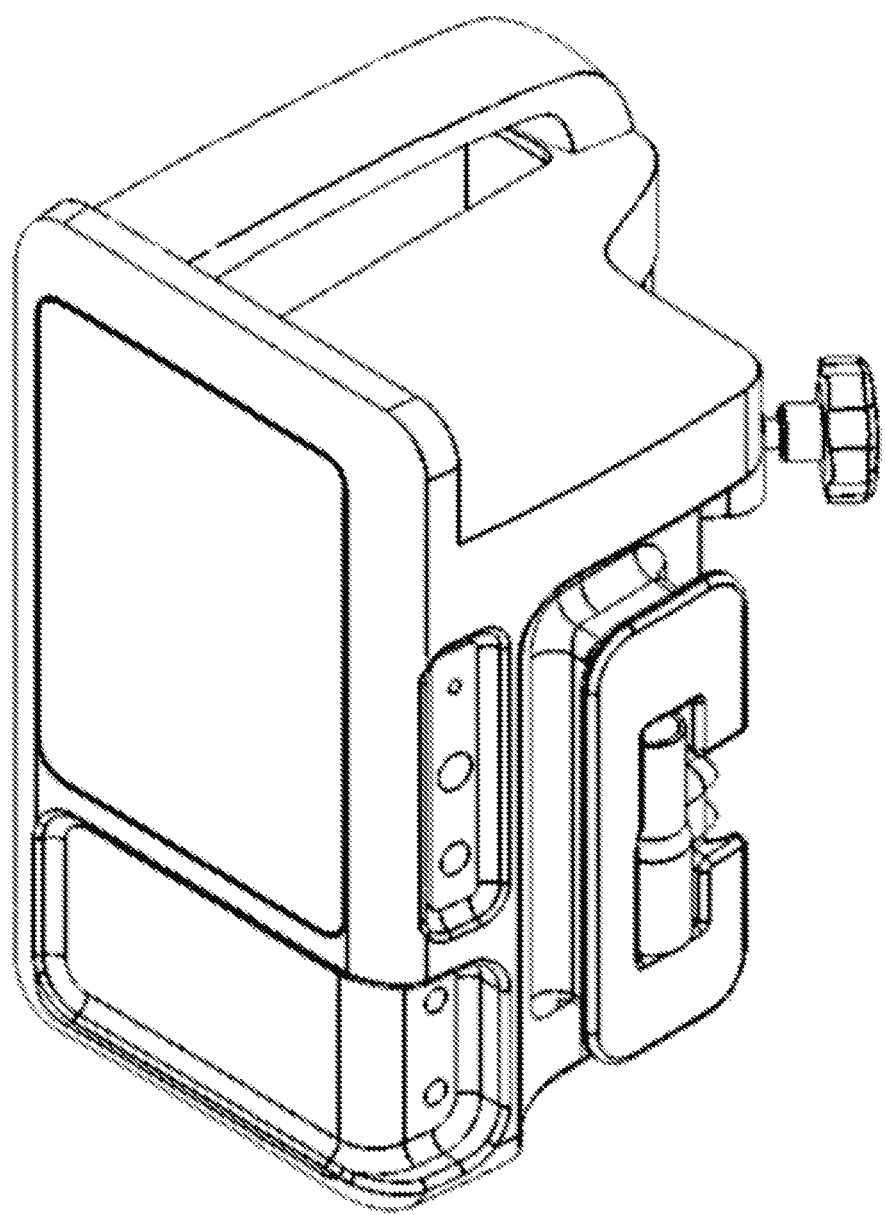
FIG. 11A is a top left front perspective view of an exemplary portable device, in accordance with exemplary embodiments of the present invention.
Figure 11B:
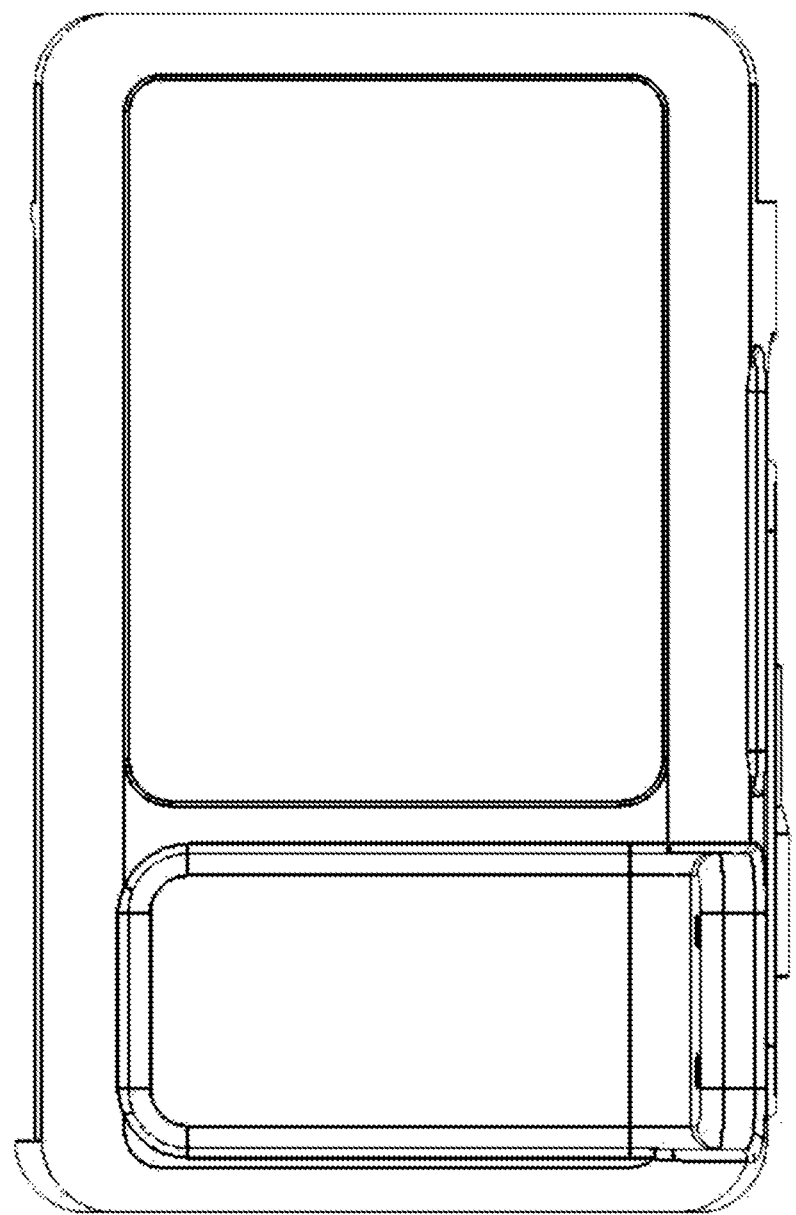
FIG. 11B is a front view of an exemplary portable device, in accordance with exemplary embodiments of the present invention.
Figure 11C:
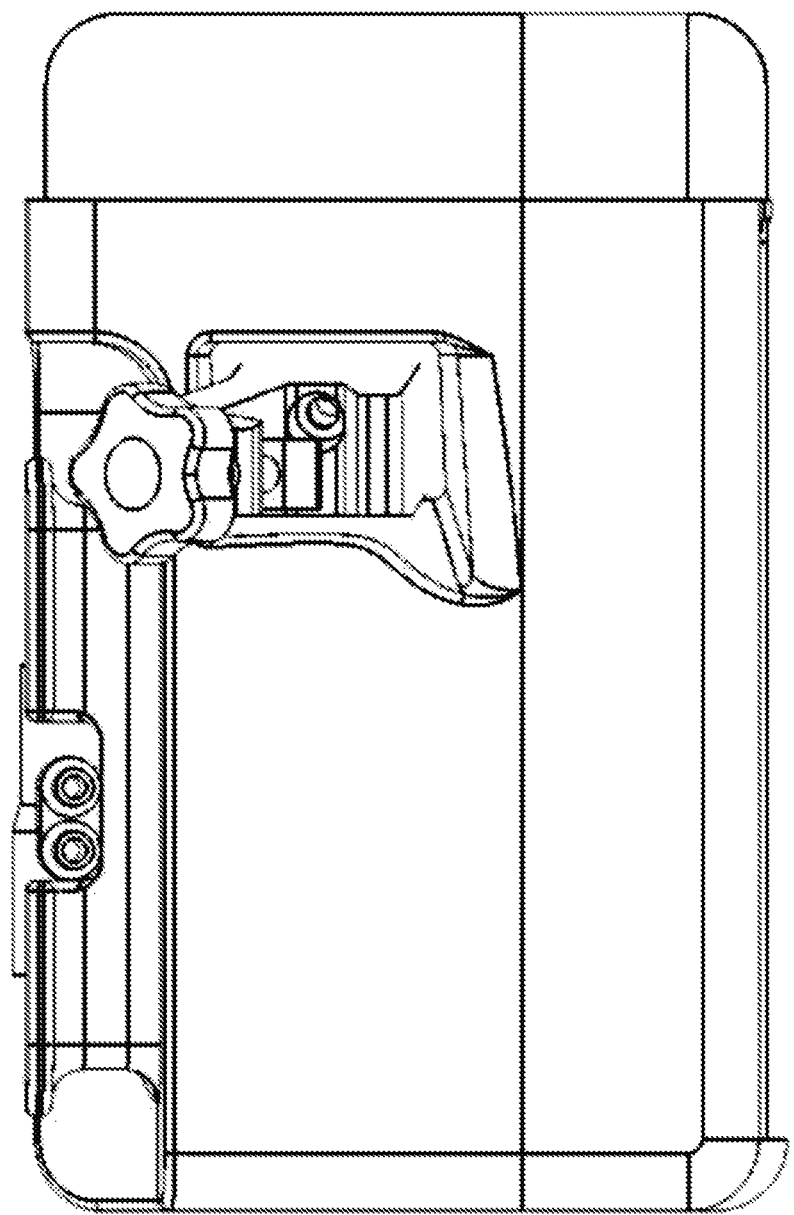
FIG. 11C is a back view of an exemplary portable device, in accordance with exemplary embodiments of the present invention.
Figure 11D:
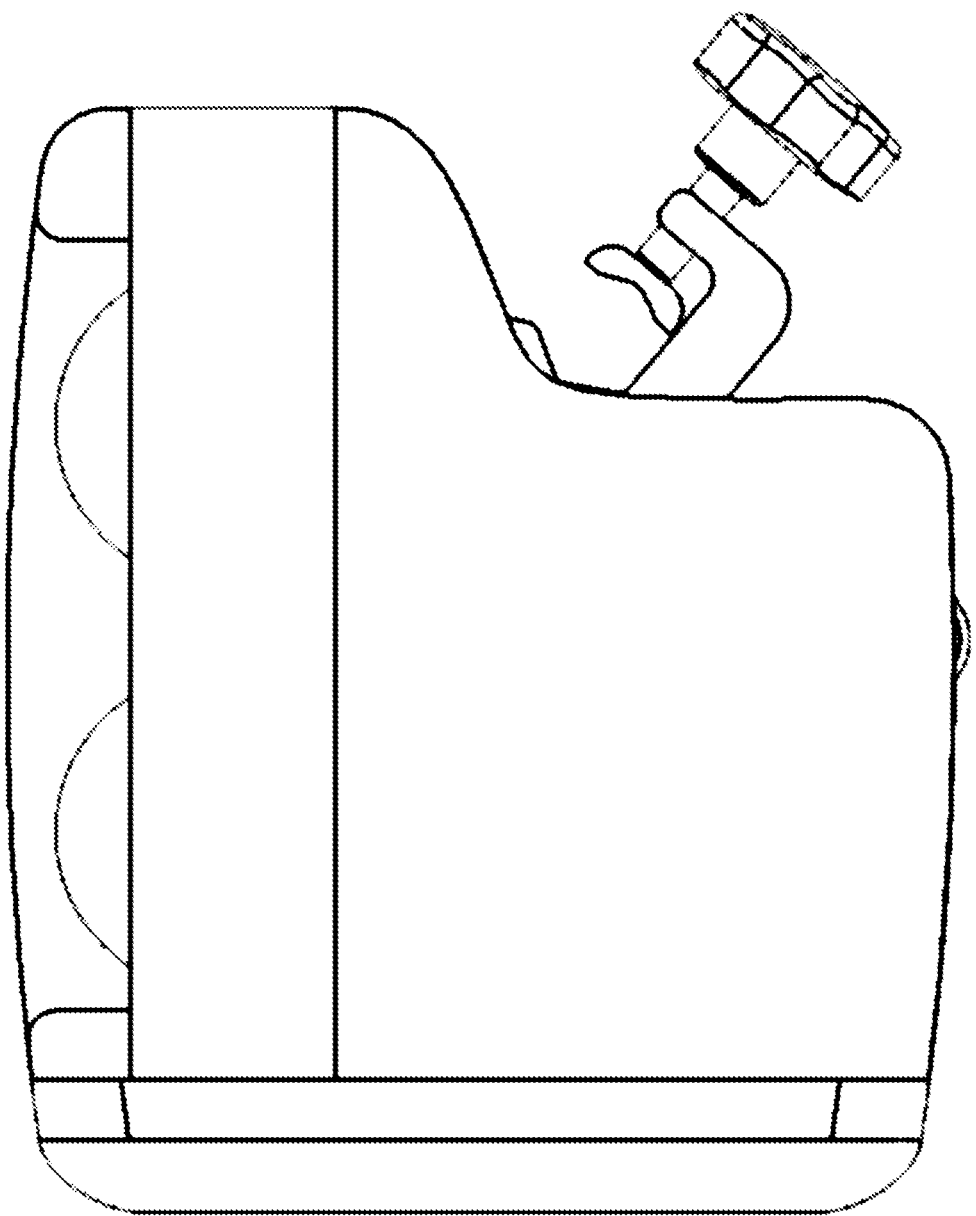
FIG. 11D is a top view of an exemplary portable device, in accordance with exemplary embodiments of the present invention.
Figure 11E:
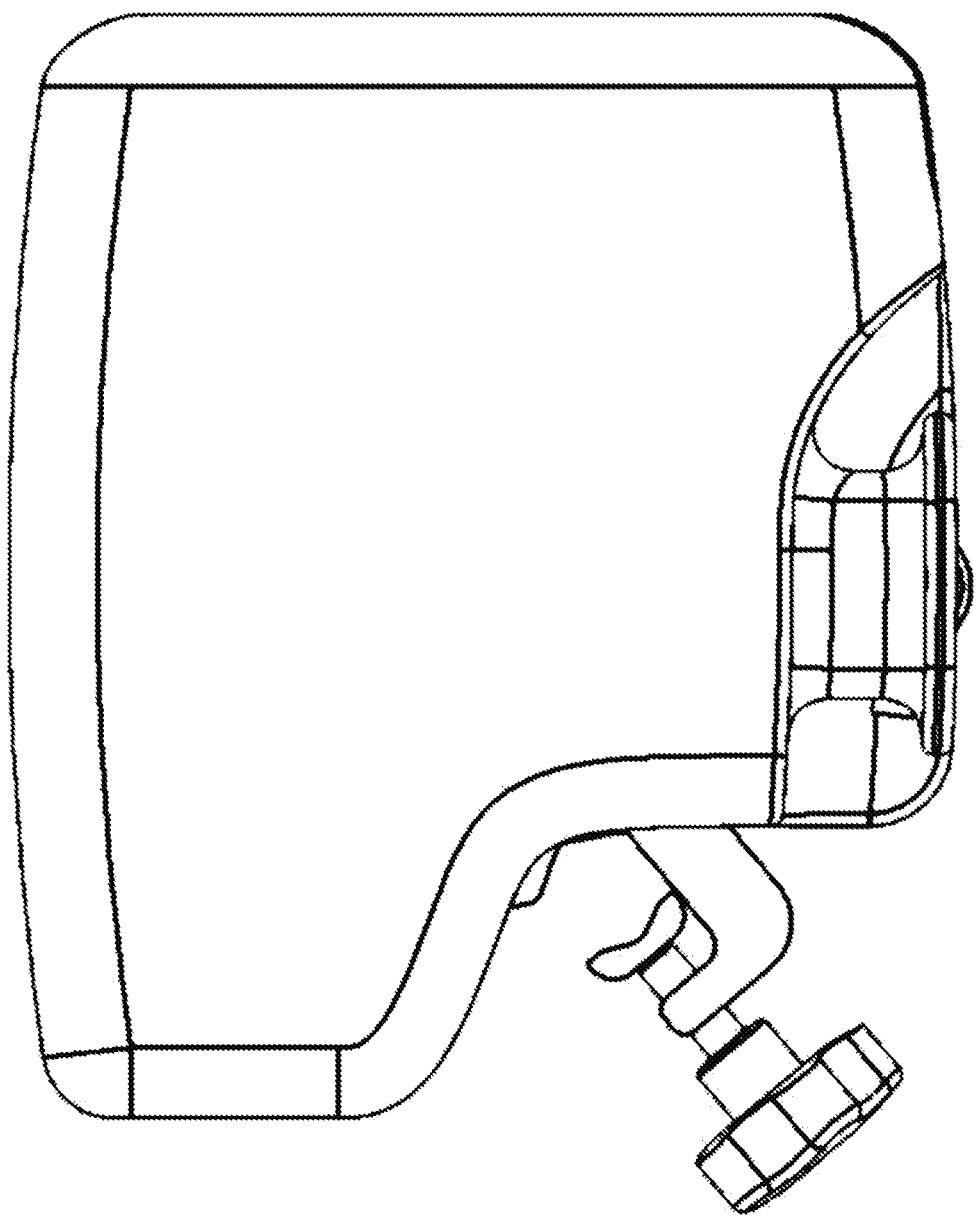
FIG. 11E is a bottom view of an exemplary portable device, in accordance with exemplary embodiments of the present invention.
Figure 11F:
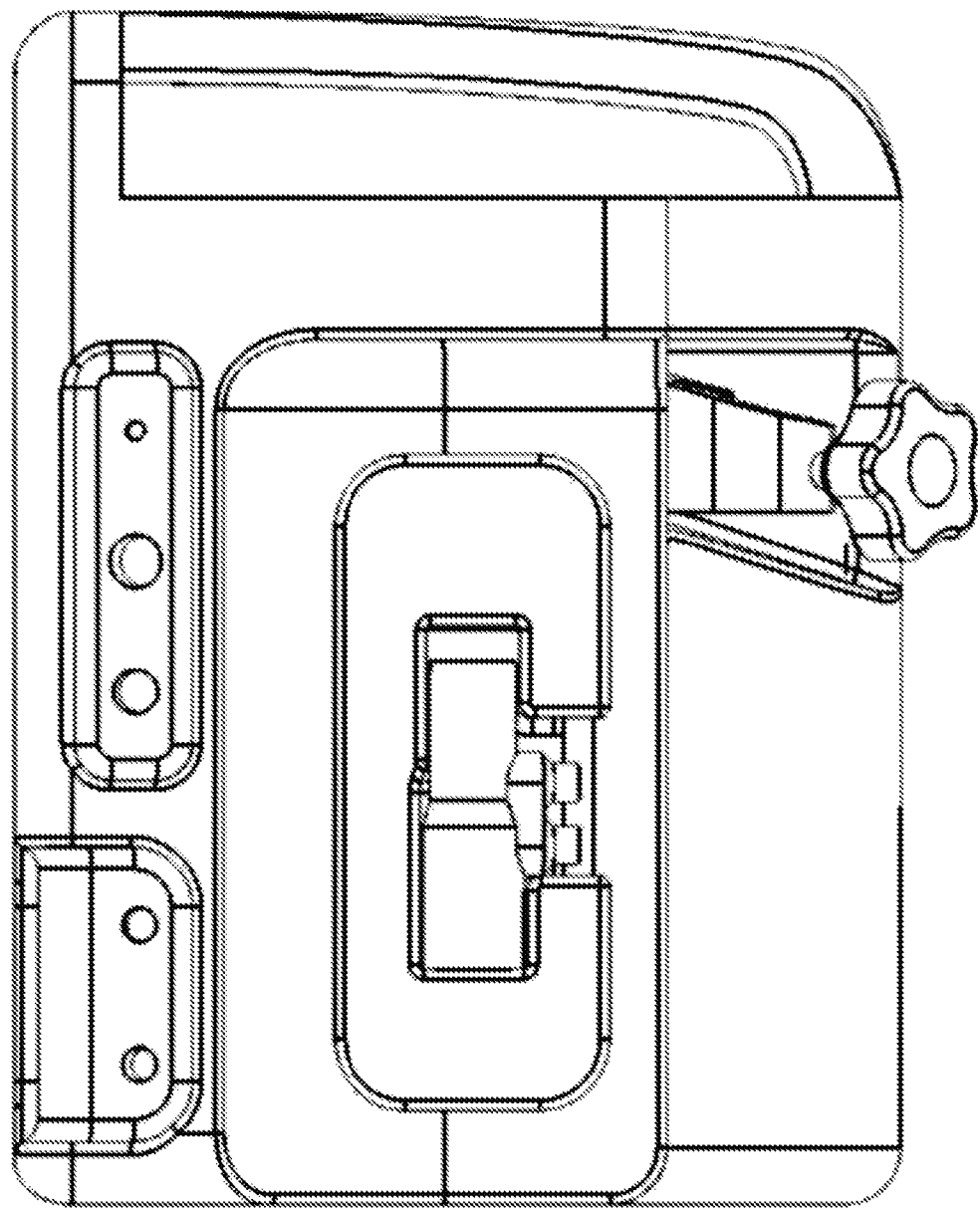
FIG. 11F is a first side view of an exemplary portable device, in accordance with exemplary embodiments of the present invention.
Figure 11G:
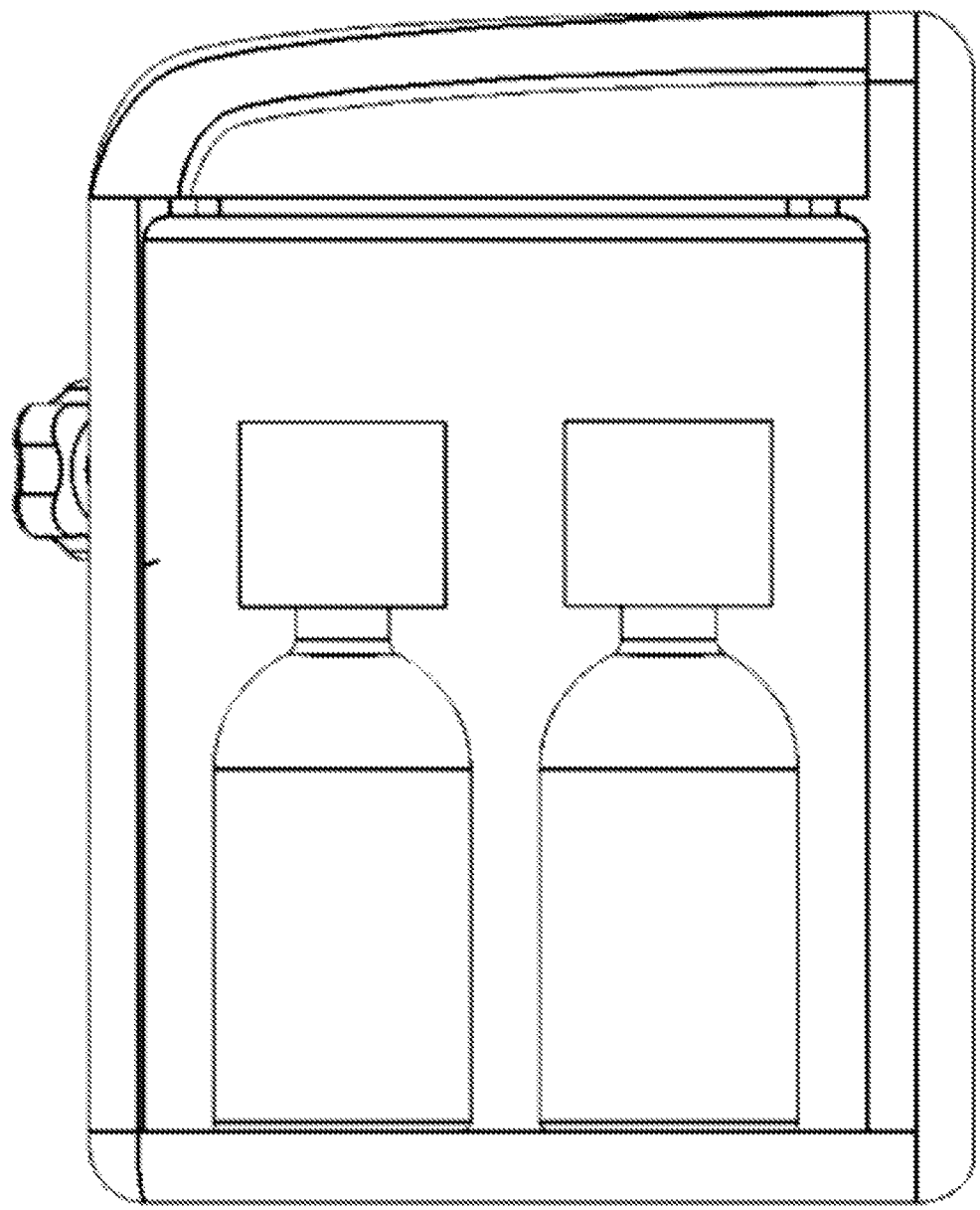
FIG. 11G is a second side view of an exemplary portable device, in accordance with exemplary embodiments of the present invention.
Figure 12A:
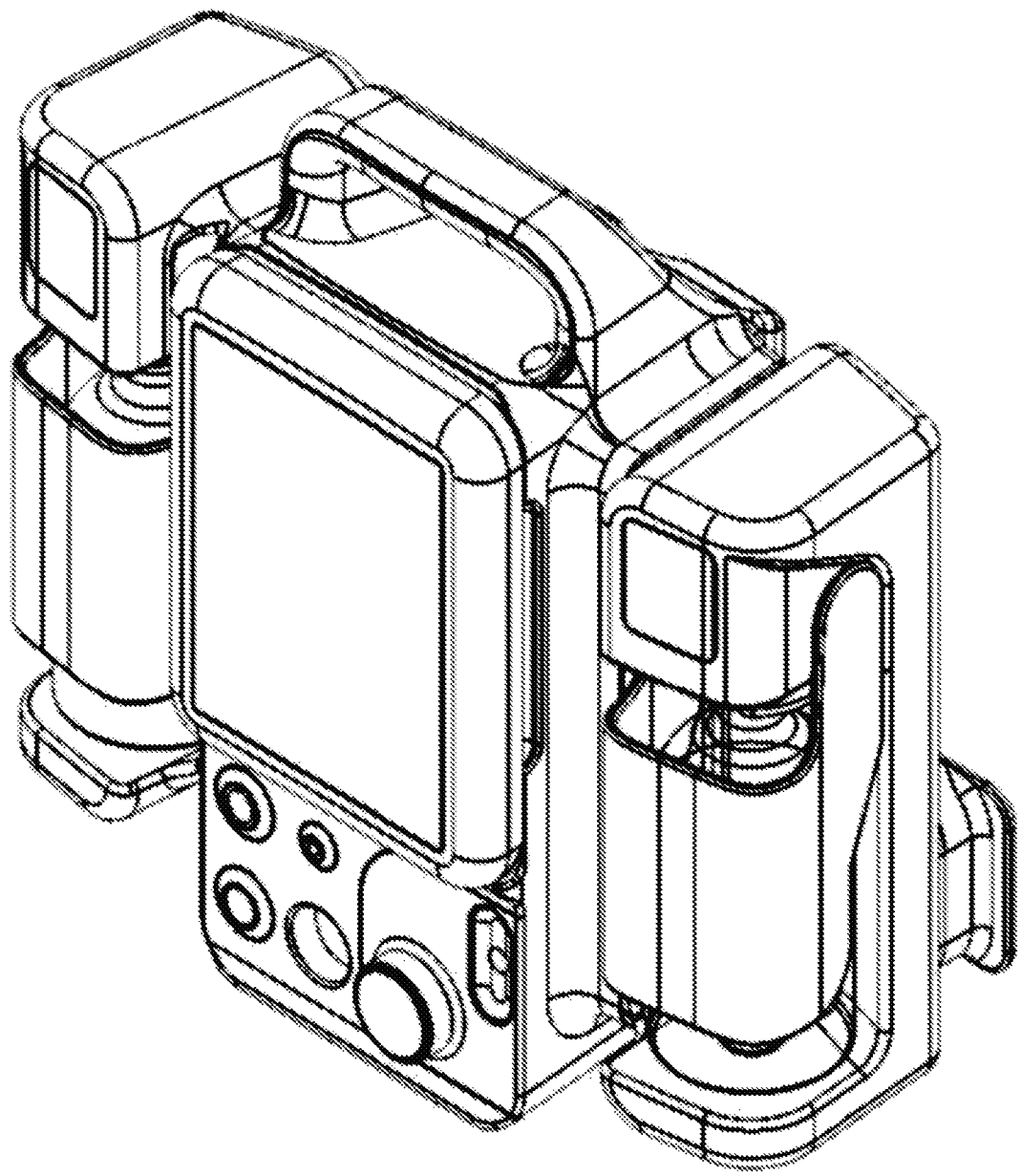
FIG. 12A is a top left front perspective view of an exemplary portable device, in accordance with exemplary embodiments of the present invention.
Figure 12B:
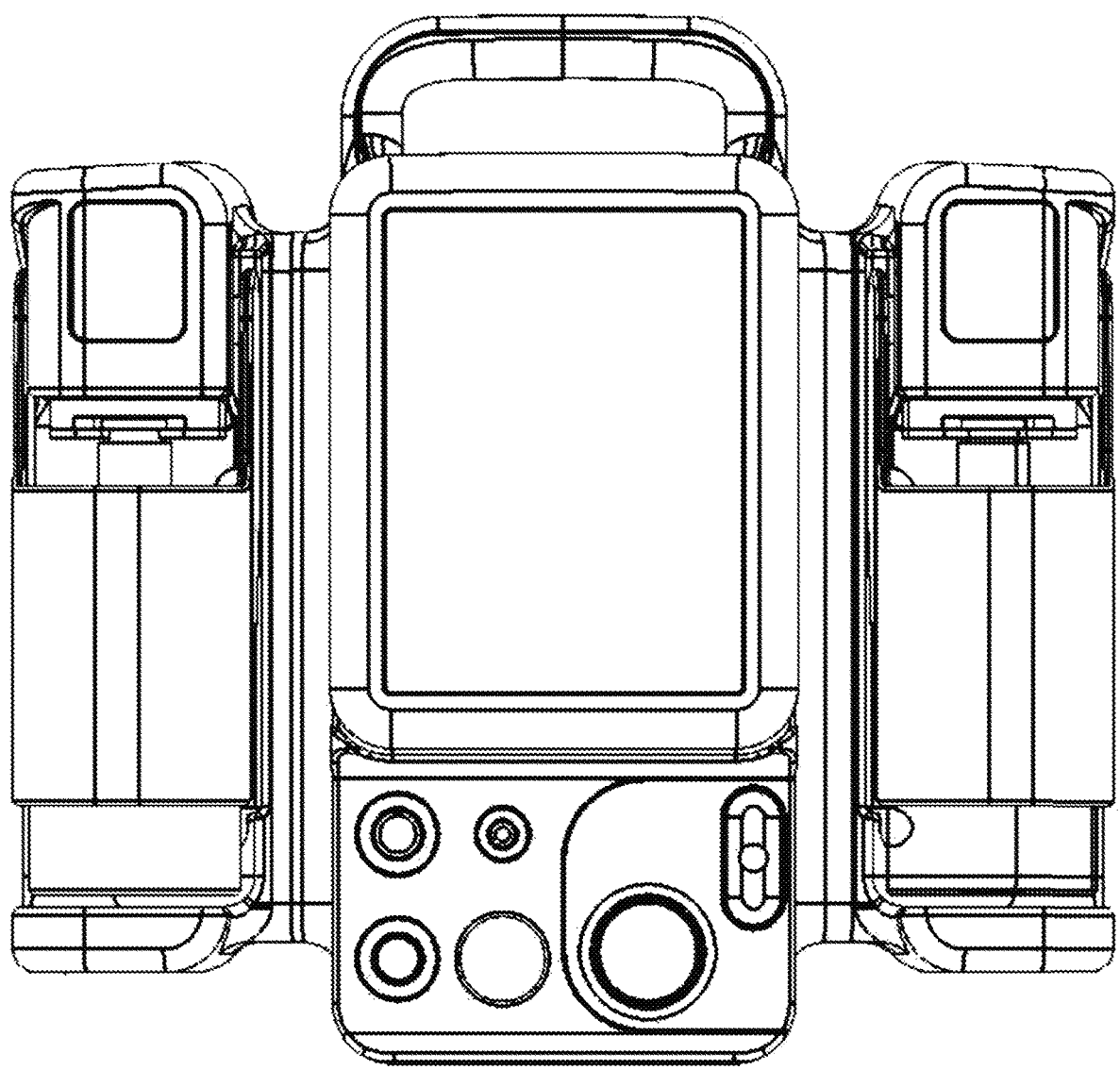
FIG. 12B is a front view of an exemplary portable device, in accordance with exemplary embodiments of the present invention.
Figure 12C:
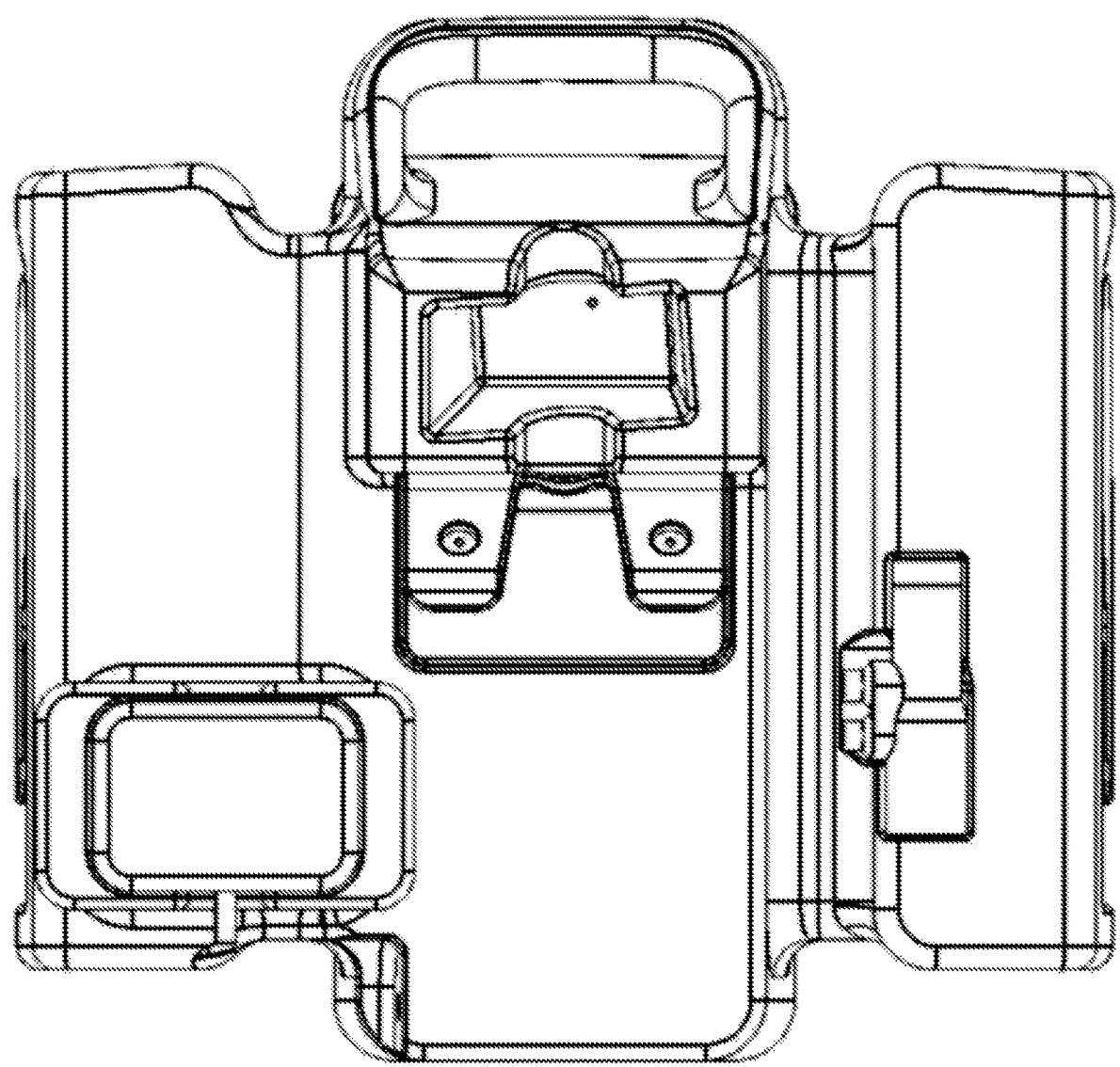
FIG. 12C is a back view of an exemplary portable device, in accordance with exemplary embodiments of the present invention.
Figure 12D:
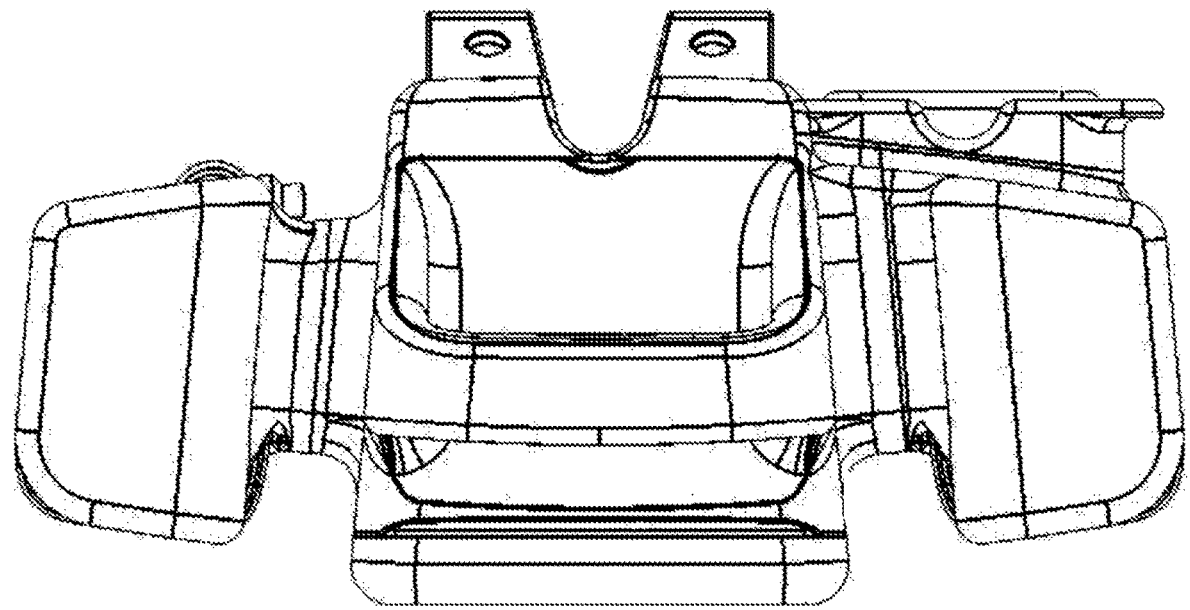
FIG. 12D is a top view of an exemplary portable device, in accordance with exemplary embodiments of the present invention.
Figure 12E:
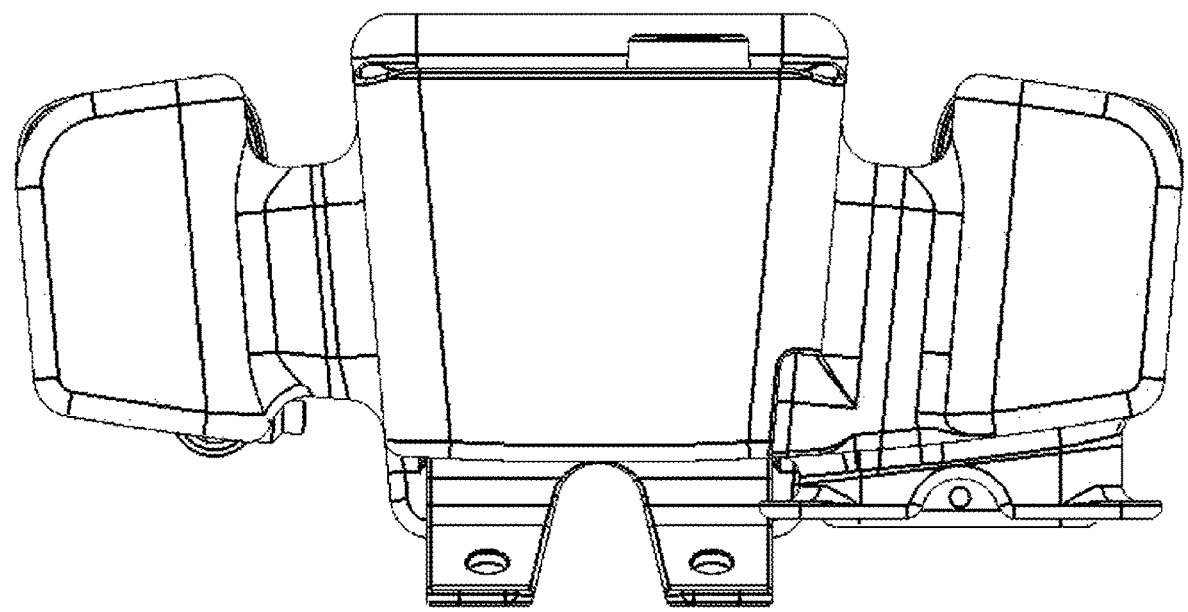
FIG. 12E is a bottom view of an exemplary portable device, in accordance with exemplary embodiments of the present invention.
Figure 12F:
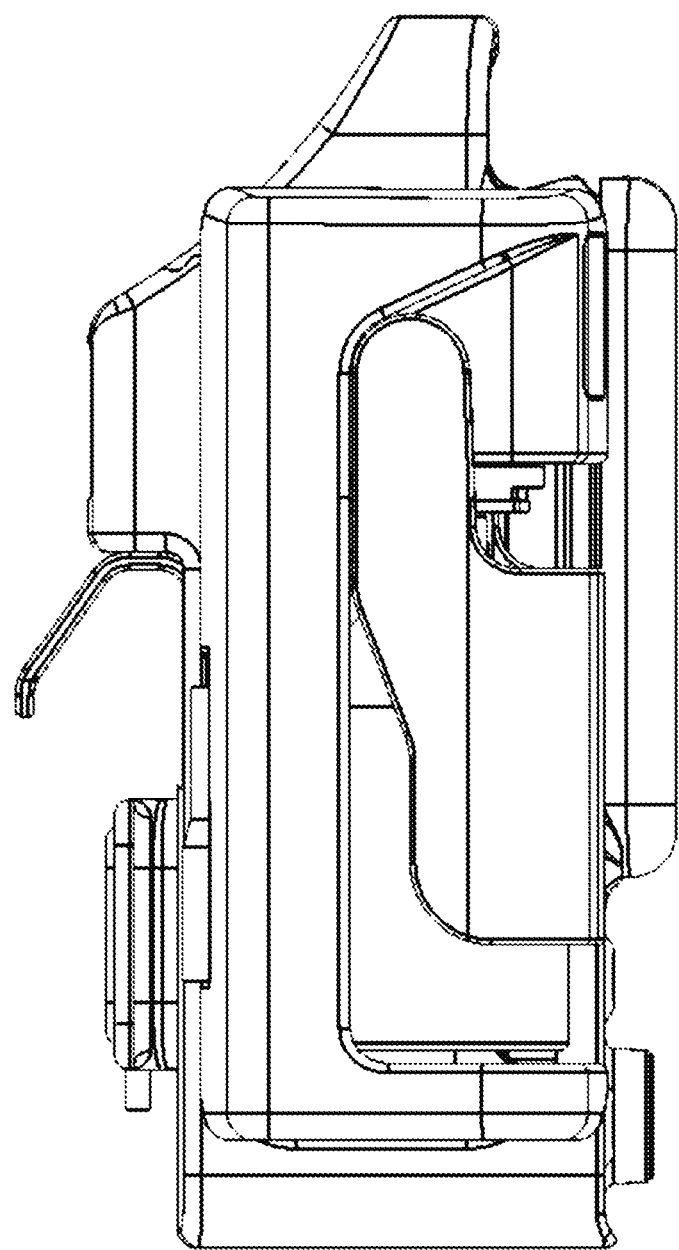
FIG. 12F is a first side view of an exemplary portable device, in accordance with exemplary embodiments of the present invention.
Figure 12G:
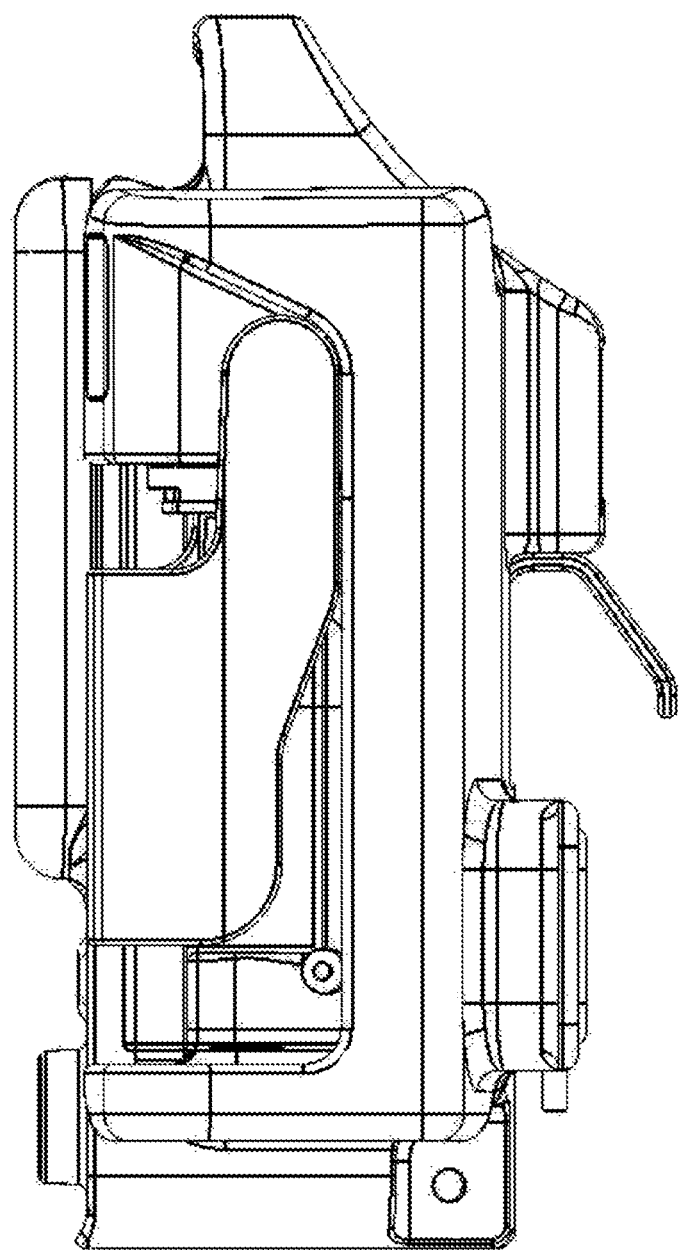
FIG. 12G is a second side view of an exemplary portable device, in accordance with exemplary embodiments of the present invention.
Figure 13A:
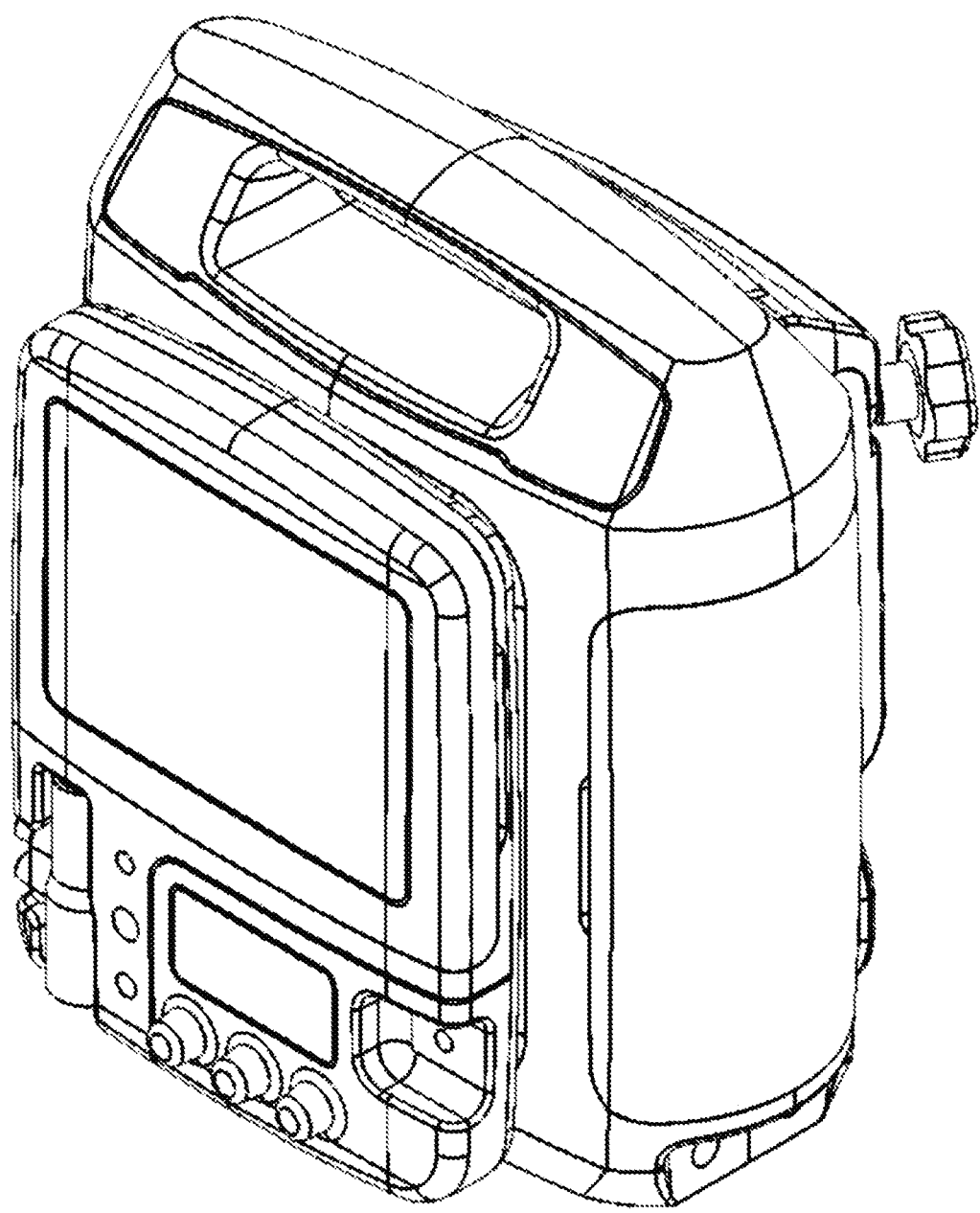
FIG. 13A is a top left front perspective view of an exemplary portable device, in accordance with exemplary embodiments of the present invention.
Figure 13B:
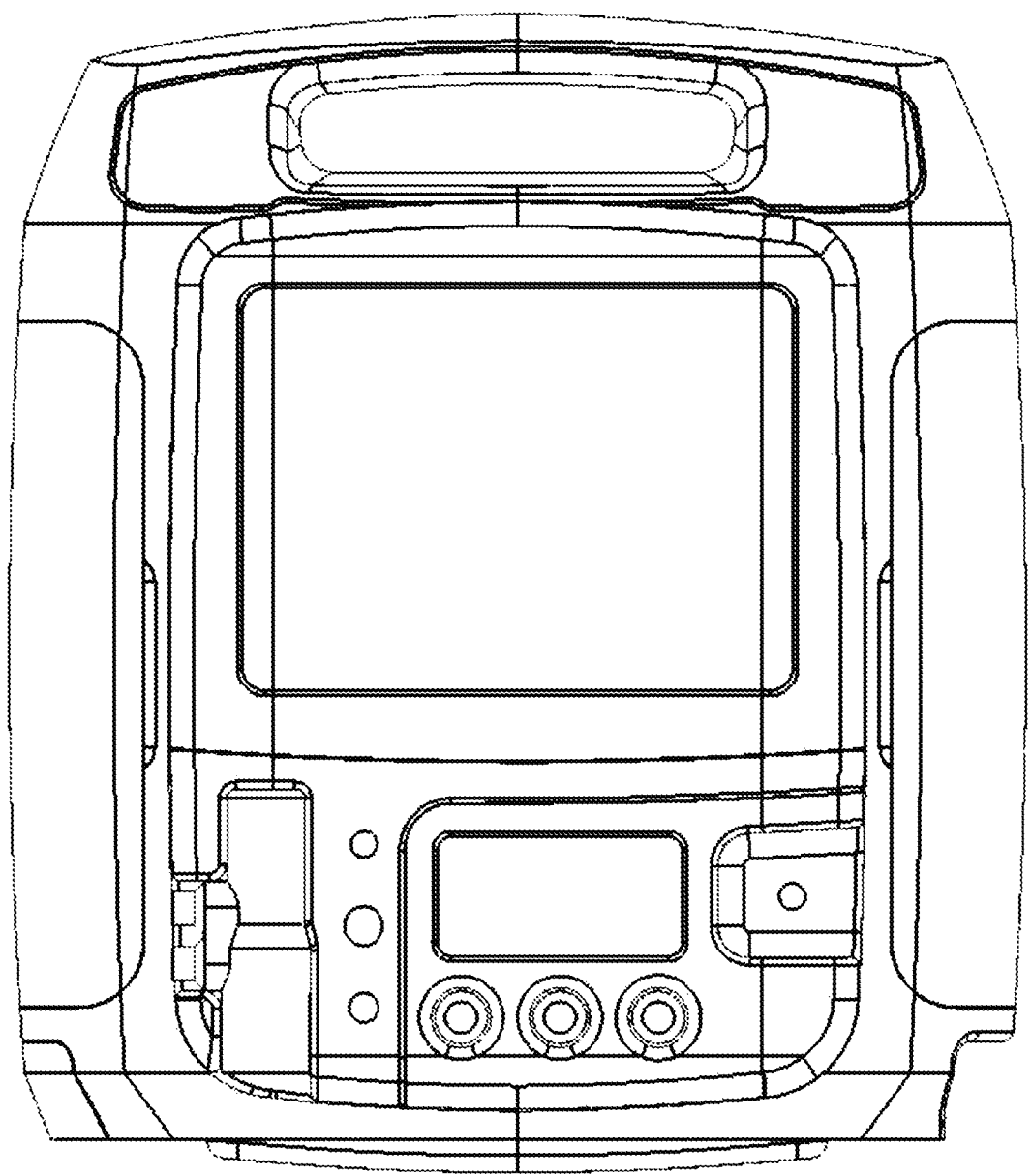
FIG. 13B is a front view of an exemplary portable device, in accordance with exemplary embodiments of the present invention.
Figure 13C:
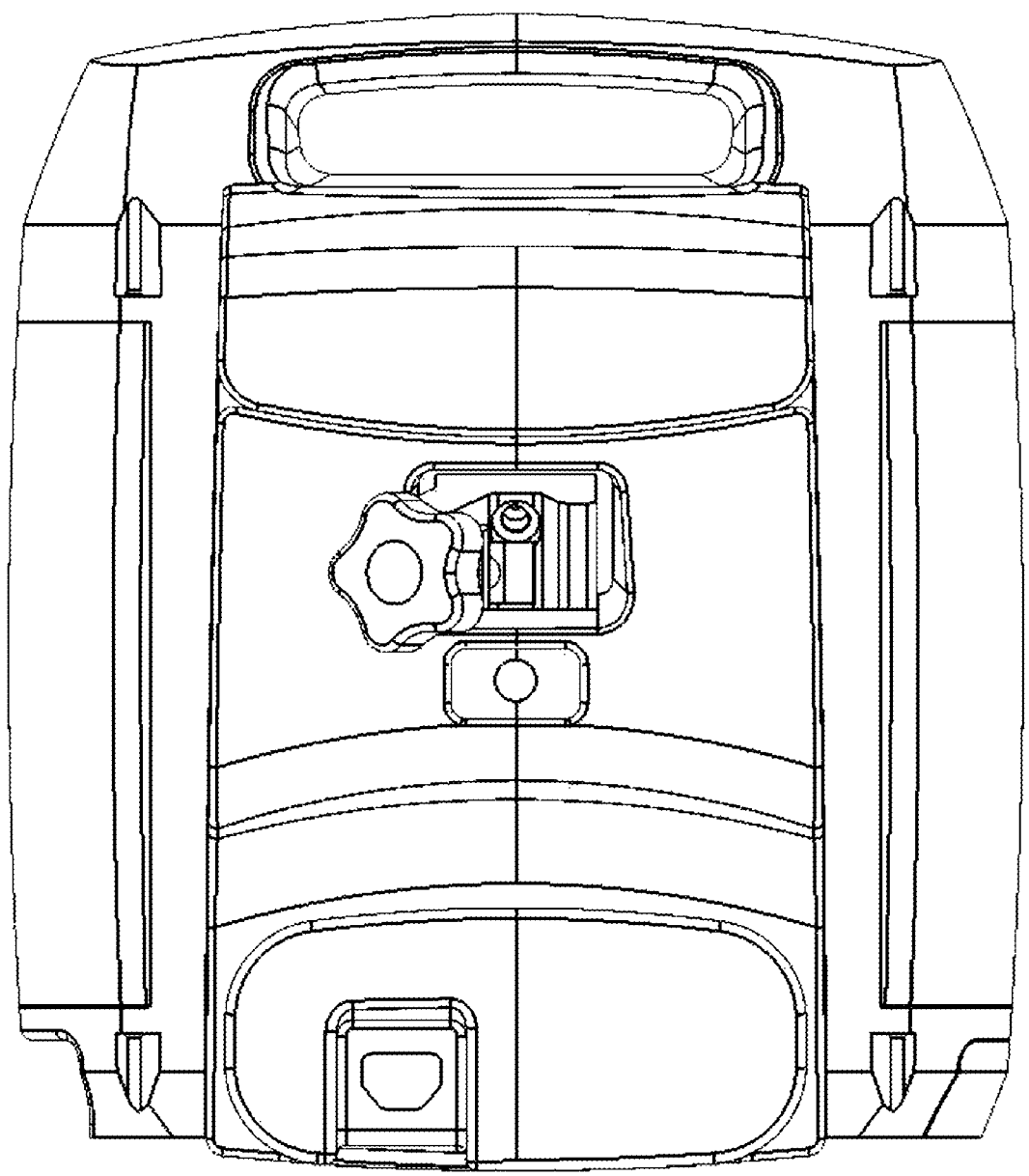
FIG. 13C is a back view of an exemplary portable device, in accordance with exemplary embodiments of the present invention.
Figure 13D:
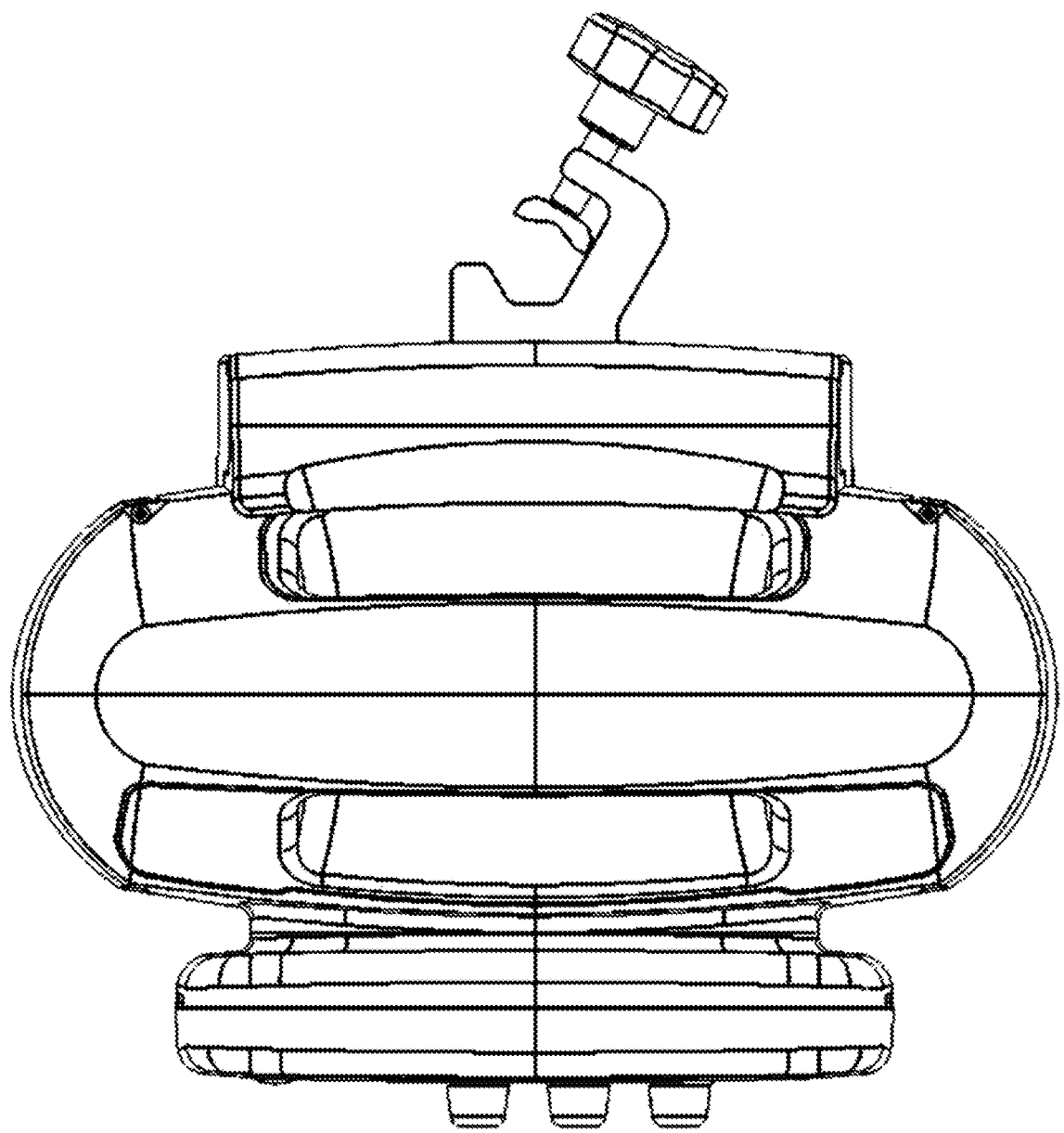
FIG. 13D is a top view of an exemplary portable device, in accordance with exemplary embodiments of the present invention.
Figure 13E:
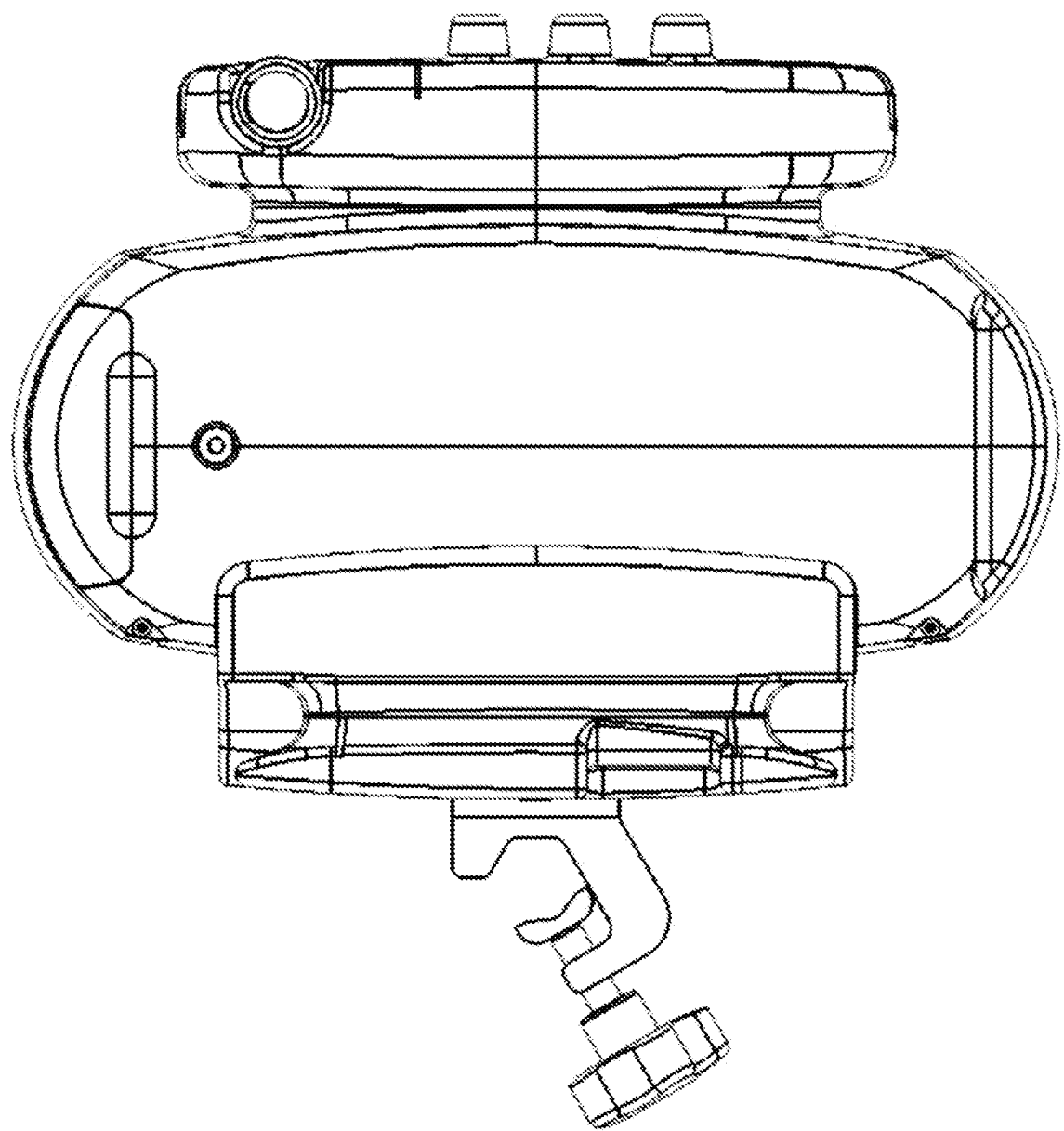
FIG. 13E is a bottom view of an exemplary portable device, in accordance with exemplary embodiments of the present invention.
Figure 13F:
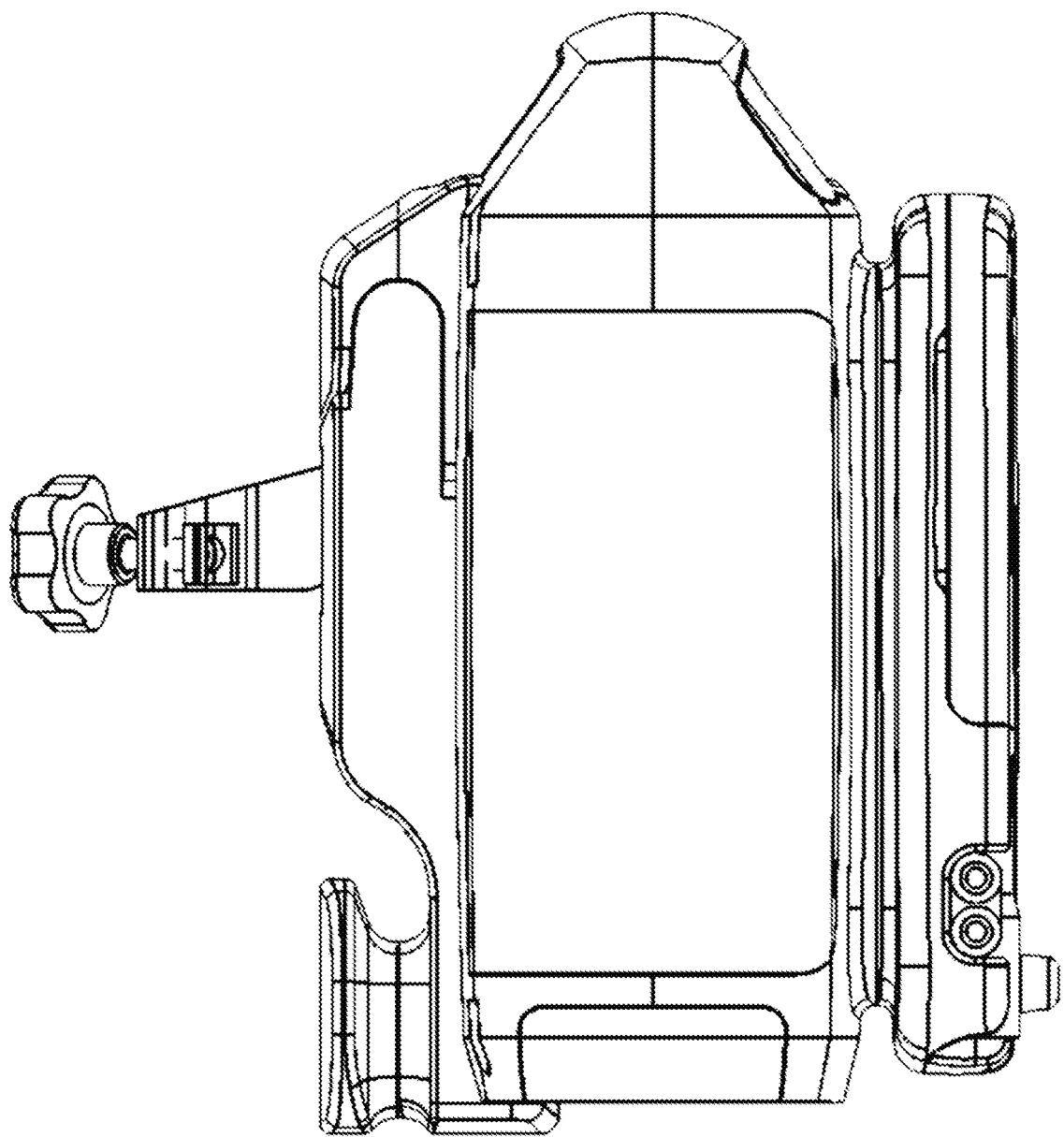
FIG. 13F is a first side view of an exemplary portable device, in accordance with exemplary embodiments of the present invention.
Figure 13G:
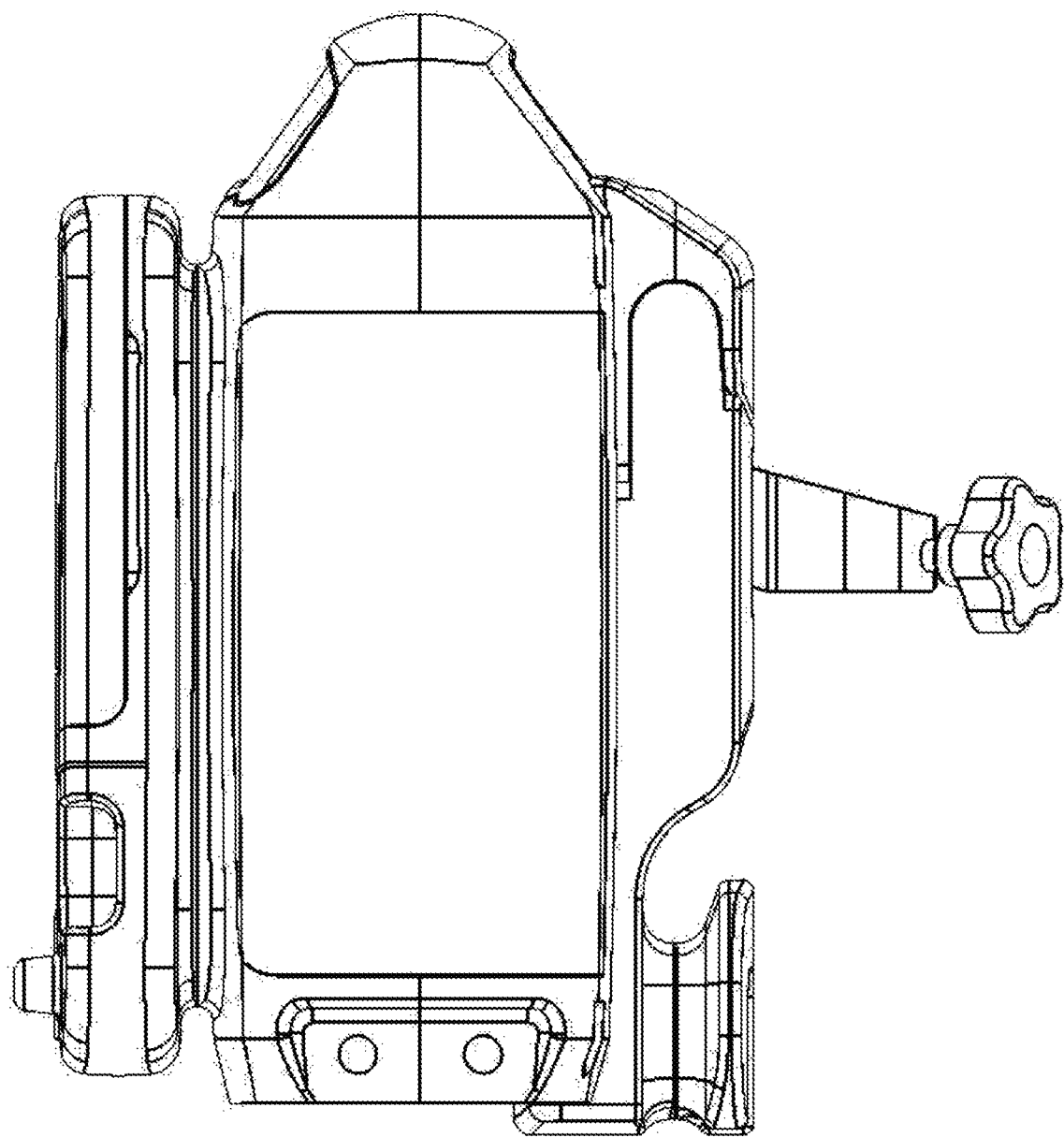
FIG. 13G is a second side view of an exemplary portable device, in accordance with exemplary embodiments of the present invention.

The CPU, for example, accessing clinical decision support stored in processor readable memory using processors, may also calculate a delivery concentration based on the measured nitric oxide flow rate and the measured flow rate through the breathing circuit. The calculated delivery concentration may be compared to the delivery concentration set by the user to provide a calculated delivery expressed as a percentage, with 100% being ideal delivery. In some embodiments, either the calculated delivery percentage and/or the calculated delivery concentration may be displayed on the screen as a calculated dose of nitric oxide. For example, the calculated delivery percentage may also be displayed on the screen as shown in FIGS. 5A-5C, or the calculated delivery may be displayed as a NO concentration in ppm as shown in FIGS. 7A-7C.

In FIGS. 5A-5C, the calculated delivery indicator has a black target delivery region, a white over delivery region and a white under delivery region. The target delivery region may be based on a certain accuracy tolerance for nitric oxide delivery, such as +/−1%, +/−2%, +/−5%, +/−10%, +/−15%, +/−20%, +/−25%, +/−30%, +/−35%, +/−40%, +/−45%, +/−50%, +/−55%, +/−60%, +/−65%, +/−70%, +/−75%, +/−80%, +/−85%, +/−90%, +/−95% or +/−100%. If the calculated delivery is, for example, in the white over delivery region or the white under delivery region, an alarm may be emitted or other notification may be provided to the user. As with the displayed flow of breathing gas, the calculated delivery may be displayed as an instantaneous value, average value, minimum value and/or maximum value.

By providing an inspired flow graphic in combination with a % delivery error graphic, a user can ascertain the device NO proportional flow control limitations. With this information, a user can adjust the breathing gas flow rate and/or the desired ppm dose to ensure that the nitric oxide delivery system may not be operating outside of its delivery range. With independent NO gas concentration monitoring one can further ascertain set verses measured deviation. Inadequate NO delivery could then be compensated by the user up or down from the desired set dose.

Figure 6:
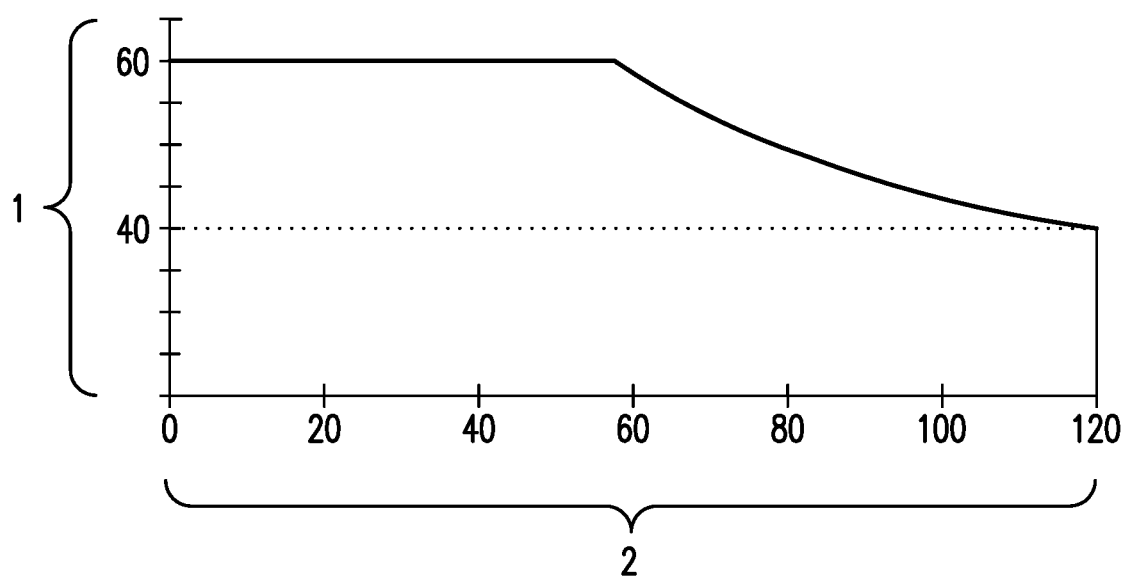
FIG. 6 depicts the maximum deliverable NO concentration as a function of the breathing gas flow rate for a nitric oxide delivery system with a maximum NO flow rate, in accordance with exemplary embodiments of the present invention.

Some current nitric oxide delivery systems have a maximum NO flow that can be delivered. For example, a nitric oxide delivery device may have a maximum NO flow of 6.35 L/min. This means the maximum deliverable NO concentration will vary based on the ventilator flow rate and the nitric oxide concentration in the therapeutic gas supply. For a cylinder having a NO concentration of 800 ppm, the maximum deliverable NO concentration will vary from approximately 80 ppm at a constant flow of 60 L/min to approximately 40 ppm at constant flow 120 L/min. FIG. 6 illustrates the NO delivery dose limitation for such a delivery system based on the expected ventilation inspired flow rates. For example, when inspired flows are sustained greater than 120 L/min with a dose set above 60 ppm, the potential exists for under-delivery shutdown conditions because the maximum NO flow rate cannot deliver the required NO to obtain the 60 ppm dose.

FIGS. 7A-7C show exemplary graphics for displaying the calculated dose of nitric oxide as a concentration in ppm. In exemplary embodiments, the graphic can be in display 208 discussed below with respect to FIG. 2 and/or any display affiliated a non-portable device (e.g., as illustrated in FIG. 7B) and/or any display affiliated with a portable device (e.g., as illustrated in FIG. 7C). As can be seen, the calculated dose in ppm can displayed as a graphic that indicates the concentration, but other ways of displaying the calculated dose can be displaying the calculated dose in ppm as an actual number, i.e. 26 ppm. Displaying the calculated dose as a concentration in ppm can be particularly useful if the nitric oxide delivery system can be in a backup mode in which the device does not provide proportional or ratio-metric delivery of nitric oxide. For example, in some situations it may be necessary to provide a constant flow of therapeutic gas that can be independent of the breathing gas flow rate, such as a flow rate of 250 mL/min of therapeutic gas. In such a backup mode, the device may calculate the dose of nitric oxide based on the constant therapeutic gas flow rate and the measured breathing gas flow rate. The device may assume the constant therapeutic gas flow rate can be a certain flow rate (i.e. 250 mL/min) or the constant therapeutic gas flow rate may actually be measured. As the flow of therapeutic gas can be constant and can be no longer dependent on the breathing gas flow rate, the concentration of nitric oxide delivered to the patient will vary depending on the breathing gas flow rate (i.e. the backup therapeutic gas delivery can be non-ratio-metric to the measured breathing gas flow rate). Accordingly, it may be beneficial to provide an estimate of the backup dose based on the known therapeutic gas flow rate (which may be an assumed flow rate) and the measured breathing gas flow rate.

In a backup mode with a constant therapeutic gas flow rate, it may be useful to display a chart or other graphic on the display to help the clinician predict what the nitric oxide concentration will be for certain breathing gas flow rates. An example of such a chart is, for example, shown in the bottom right corner of FIGS. 7A-7C. Using this information, the clinician may set the ventilator to a certain flow rate or pressure control to achieve the desired nitric oxide concentration for the backup mode delivery.

In exemplary embodiments, the flow rate of breathing gas and/or the calculated nitric oxide dose can be displayed on the main screen used during therapy. However, in at least some exemplary embodiments, the flow rate and/or calculated dose may not be directly displayed on the main screen, but the user may access a screen that displays information such as the breathing flow rate history or the instantaneous breathing gas flow rate. The breathing flow rate history may include the peak and/or average flow rates for a certain period of time, such as the past 5, 10, 15, 20, 30 or 45 seconds, the past 1, 2, 5, 10, 15, 20, 30, 45, 60 minutes, or since the start of the current therapy administration. In at least some exemplary embodiments, the breathing flow rate history can be provided for the past several seconds, such as about 10 seconds. The system may include appropriate components for calculating and storing the information regarding breathing flow rate history, such as a CPU and processor readable memory. Similarly, the calculated dose that can be displayed may be instantaneous, average, maximum and/or minimum values. A calculated dose history may include the peak and/or average flow rates for a certain period of time, such as the past 5, 10, 15, 20, 30 or 45 seconds, the past 1, 2, 5, 10, 15, 20, 30, 45, 60 minutes, or since the start of the current therapy administration. In exemplary embodiments, the calculated dose history can be provided for the past several seconds, such as about 10 seconds.

The system may comprise an input device that can receive input from a user. Such user input can include operation parameters, such as desired nitric oxide concentration and flow limits. In at least one exemplary embodiment, an input device and display device may be incorporated into one unit, such as a touchscreen device.

The breathing gas delivery system can include any system capable of providing a supply of breathing gas to the patient. The breathing gas may be supplied by ventilatory support, mechanically assisted ventilation or by spontaneous ventilation. Examples of suitable ventilation systems include, but are not limited to, conventional ventilators, jet ventilators, high frequency oscillator ventilators and continuous positive airway pressure (CPAP) systems. Non-invasive approaches can also be used to supply the breathing gas, including bubble CPAP, synchronized inspiratory positive airway pressure (SiPAP), nasal cannula and heated high flow nasal cannula.

The therapeutic injector module combines the flow of the breathing gas and the flow of the therapeutic gas. The injector module ensures the proper delivery of inhaled nitric oxide at a set dose based on changes in flow of the breathing gas via communication with the CPU.

In at least some exemplary embodiments, the nitric oxide delivery device can be suitable for use with gentle ventilation strategies. Gentle ventilation may be a ventilator strategy that limits shear stress and pressures on the alveoli, while maintaining adequate oxygenation and ventilation, to reduce lung injury and minimize long term pulmonary complications. Gentle ventilation includes, but is not limited to: (1) maintaining adequate ventilation and oxygenation of the neonate; (2) limiting peak to peak pressures during mechanical ventilation; (3) adjusting ventilator pressure(s) as needed to maintain adequate lung volume without doing harm.

In some embodiments, gentle ventilation involves reducing inspiratory pressure enough to allow for some permissive hypercapnia. Gentle ventilation may include, but is not limited to, utilization of non-invasive ventilation (NIV) methods of respiratory support to limit injury to the lung, whereby the device and equipment supplies gas flow at lower pressures, thus eliminating the breath-to-breath high PIP's (Peak Airway Pressures) which increases the frequency of lung injury through shearing forces and stretching of alveoli. Gentle ventilation may include the use of bubble CPAP, Si PAP, HHHFNC (Heated Humidified High Flow Nasal Cannula) and methods of mechanical ventilation, whereby the intubated infant receives PIP's less than or equal to 20 cm $H_2O$ and oxygen saturations are 88-92%. For those infants on HFOV or HJV, pressures are maintained to minimize lung injury. Equipment to maintain an approach to gentle ventilation includes, but is not limited to, nasal cannula, nasal prongs and adaptive masks for NIV support. Examples of suitable equipment for gentle ventilation are Neopuff® and High Flow Bubble CPAP available from Fisher & Paykel Healthcare, Inc., and products available from Vapotherm, Inc.

The present invention clinical decision support can be affiliated with and/or utilized by various technologies and configurations of non-portable and/or portable systems for delivering a therapeutic gas to a patient, when nebulized drugs may and/or may not be being delivered to the patient. For example, in exemplary embodiments, delivering therapeutic gas to a patient, systems of the present invention can include, but is not limited to, a therapeutic gas supply comprising nitric oxide; a breathing gas delivery system that provides breathing gas to a patient; and/or a therapeutic gas delivery system. The therapeutic gas delivery system can include, but is not limited to, a first inlet configured to be placed in fluid communication with the therapeutic gas supply; a second inlet configured to be placed in fluid communication with the breathing gas delivery system; a therapeutic gas injector module adapted to be placed in communication with the first inlet and the second inlet to provide a combined flow of breathing gas and therapeutic gas; an outlet in fluid communication with injector module and configured to supply breathing gas and therapeutic gas to a patient; a control circuit in communication with a first flow sensor that measures the flow of breathing gas from the breathing gas delivery system and a second flow sensor that measures the flow of therapeutic gas to determine a calculated dose of nitric oxide based on the therapeutic gas and breathing gas flow rates; and a display to provide a visual and/or numeric indication of the calculated dose of nitric oxide.

Figure 2:
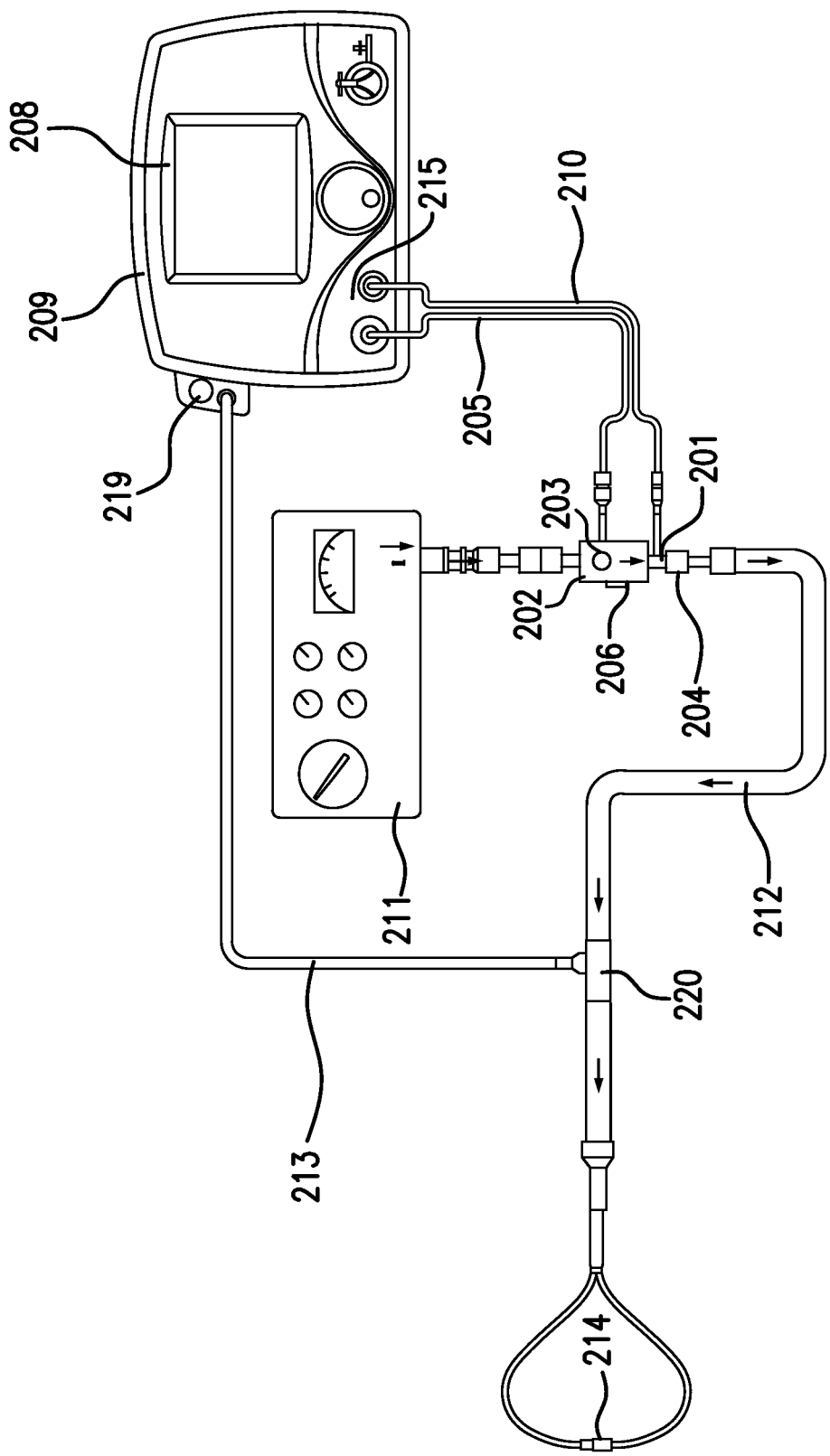
FIG. 2 depicts an exemplary system for providing a therapeutic gas to a, in accordance with exemplary embodiments of the present invention.

Referring to FIG. 2, in accordance with exemplary embodiments of the present invention, an exemplary system for delivering a therapeutic gas that may be affiliated with clinical decision support, when nebulized drugs may and/or may not be being delivered to the patient, is shown. This system for delivery of a therapeutic gas can be a non-portable system, as shown, and/or portable system. The system can include, but is not limited to, a therapeutic injector module 203 in fluid communication with a first inlet 201 and a second inlet 202. First inlet 201 can be in fluid communication with therapeutic gas injector tube 210, which can be in fluid communication with a therapeutic gas supply comprising nitric oxide. Second inlet 202 can be in fluid communication with breathing gas delivery system 211, illustrated as a ventilator. The arrows in FIG. 2 indicate the direction of flow for the breathing gas and the combined gas mixture of therapeutic gas and breathing gas. Flow sensor 206 can be in fluid communication and downstream of second inlet 202, and/or monitors the flow of breathing gas through therapeutic injector module 203. The top view of therapeutic injector module 203 is shown. The therapeutic gas and breathing gas mix in therapeutic injector module 203 to provide a gas mixture. Injector module cable 205 connects therapeutic injector module 203 with control module 209. Flow sensor 206 in the control module 209 measures the flow of therapeutic gas flowing through therapeutic gas injector tube 210 to the therapeutic injector module 203. Control module 209 also comprises display 208, which can display real-time flow of breathing gas and/or calculated dose of nitric oxide and/or provide alerts when the flow of breathing gas rises above or falls below a predetermined level. Inspiratory breathing hose 212 can be in fluid communication with outlet 204 and nasal cannula 214. The inspiratory breathing hose provides the gas mixture of breathing gas and therapeutic gas to nasal cannula 214, which delivers the gas mixture to the patient. Patient gas sample line 213 diverts some of the flow of the gas mixture from inspiratory breathing hose 212 and brings it to sample block 219.

Sample block 219, also known as a sample pump, draws some of the flow of the gas mixture through gas sample line 213. As shown in FIG. 2, the sample block 219 may be incorporated into the control module 209. The sample block analyzes the concentrations of nitric oxide, oxygen, and nitrogen dioxide in the gas mixture. Typically, a sample block will sample about 250 mL/min of the gas mixture. However, when flow rates of breathing gas are near 250 mL/min, sampling 250 mL/min of the gas mixture would leave little or no gas to deliver to the patient. Therefore, in one or more exemplary embodiments, the sample block can be modified to draw or pull a volume of combined therapeutic and breathing gas such that the gas sampled per minute can be less than or equal to 100 mL/min. In at least some exemplary embodiments, the gas sampled can be less than or equal to 50 mL/min. In at least some other exemplary embodiments, the gas sampled can be less than or equal to 20 mL/min. The sampling block may have smaller pumps and/or more sensitive sensors in order to sample lower flow rates.

The concentrations of nitric oxide, oxygen and nitrogen dioxide measured in the sample block 219 may be shown on display 208. As a result of sampling lower amounts of the gas mixture, refresh rates of monitored values may need to be faster regarding displayed values.

Generally speaking, nebulizers should be interfaced with the patient breathing circuit somewhere downstream of the sample T adapter 220 used by sample block 219 to draw some flow for analysis and/or gas monitoring. Nebulizers should be interfaced downstream of the sample T adapter 220 because the aerosolized droplets can clog the sample system, for example, if they are pulled in with the gas sample stream. However, there are times when nebulizers may be interfaced upstream of and/or substantially close to sample T adapter 220. This can damage elements of the system such as, but not limited to, sample block 219.

In exemplary embodiments, nebulizer mode affiliated with clinical decision support can be activated when the clinician may be about to start delivery of drug through a nebulizer device. Nebulizer Mode can be activated by the clinician interfacing with graphical user interface of the delivery system. In exemplary embodiments, users (e.g., clinicians) can input (e.g., via the graphical user interface, etc.) the amount of time they plan to run the nebulizer for and then start (e.g., pressing a "start" button in the graphical user interface) nebulizer mode.

In exemplary embodiments, when nebulizer mode affiliated with clinical decision support is started, the delivery system then turns off the sample pump that draws the sample stream into the monitoring system. Accordingly, in nebulizer mode, nebulized drugs and therapeutic gas can be delivered to the patient without the risk of damaging elements of the system affiliated with sampling.

In exemplary embodiments, when nebulizer mode is running, monitoring may still be provided to users (e.g., clinician, etc.) that accurate delivery of the therapeutic gas is still taking place. For example, in exemplary embodiments, in nebulizer mode the delivery bar graph illustratively depicted in FIGS. 5A-5C can be displayed on the graphical user interface of the system. For another example, in exemplary embodiments, in nebulizer mode the concentration in PPM can be displayed on the graphical user interface of the system. In exemplary embodiments, this concentration and/or display can be based on the NO flow sensor and Injector Module sensor ratio-metric calculation.

In exemplary embodiments, after the amount of time the user entered into the nebulizer mode elapses the sample pump can start back up and gas concentration measurement can resume. Further, flow sensor based ratio-metric calculation and/or representation of the therapeutic gas concentration may still displayed until the measured gas concentration approaches a constant concentration.

The therapeutic gas delivery system can incorporate any or all of the embodiments for a therapeutic gas system disclosed herein and/or incorporated by reference.

The breathing gas delivery system for delivering therapeutic gas can include any system capable of providing a supply of breathing gas to the patient. The breathing gas may be supplied by any form of ventilatory support, or mechanically assisted ventilation or by spontaneous ventilation. Examples of suitable ventilation systems include, but are not limited to, conventional ventilators, jet ventilators, high frequency oscillator ventilators and CPAP systems. Non-invasive approaches can also be used to supply the breathing gas, including bubble CPAP, SiPAP, nasal cannula and heated high flow nasal cannula.

In exemplary embodiments, a method of monitoring the delivery of therapeutic gas to a patient, for example, using clinical decision support, when nebulized drugs may and/or may not be being delivered to the patient, can include, but is not limited to, the steps of providing a flow of breathing gas; providing a flow of therapeutic gas comprising nitric oxide; measuring the flow of breathing gas; measuring the flow of therapeutic gas; delivering the breathing gas and therapeutic gas to a patient; determining a calculated dose of nitric oxide based on the measured flow of breathing gas and the measured flow of therapeutic gas or a known flow of therapeutic gas; and/or displaying the calculated dose of nitric oxide on a display module, to name a few.

Figure 3:
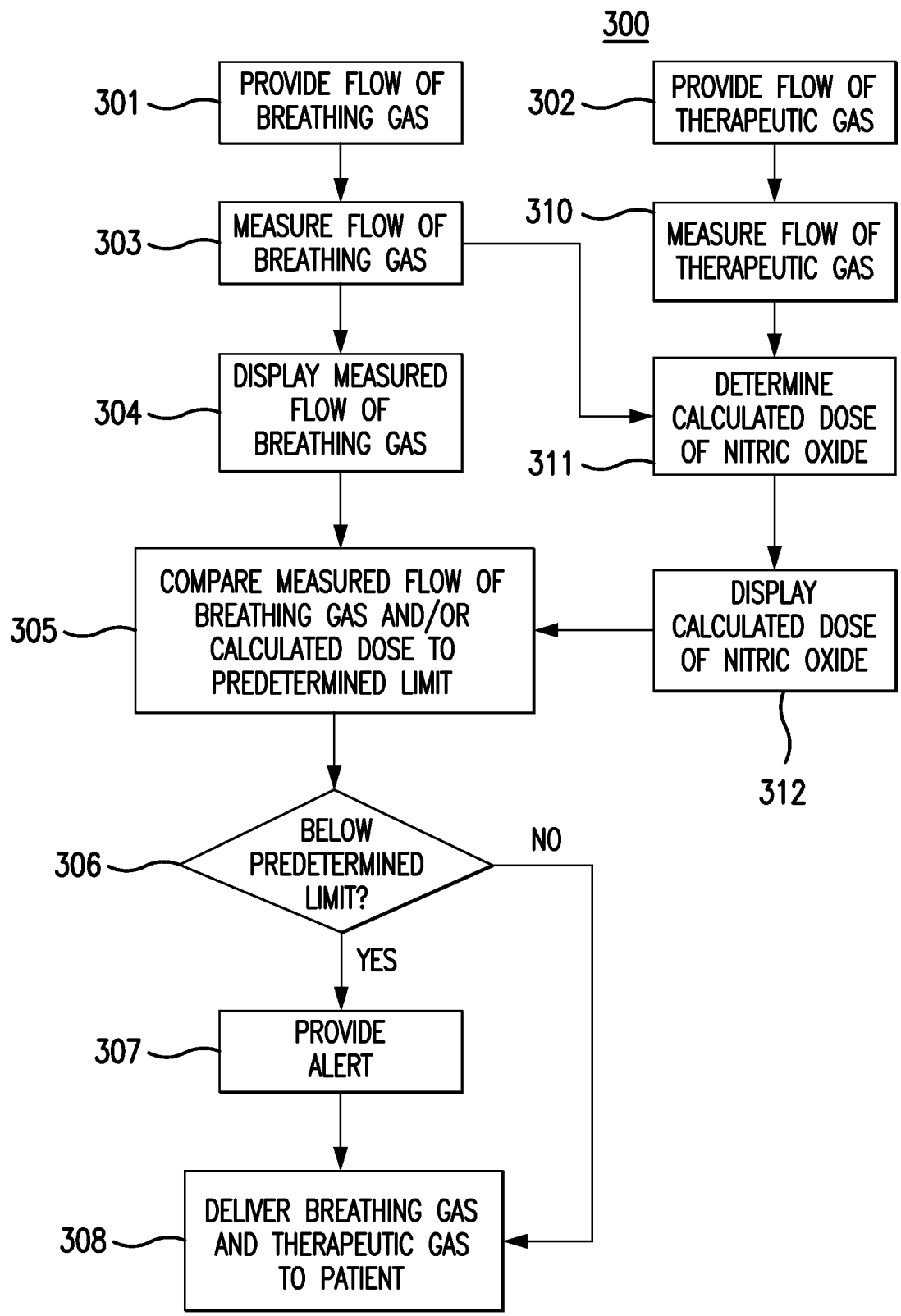
FIG. 3 depicts a flow chart for exemplary methods of monitoring the delivery of therapeutic gas to a patient, in accordance with exemplary embodiments of the present invention.

FIG. 3 depicts a flow chart for at least one exemplary embodiment of a method 300 for monitoring the delivery of therapeutic gas to a patient, when nebulized drugs may and/or may not be being delivered to the patient. Flow chart 300 can be an algorithm affiliated with clinical decision support that can be stored in processor readable memory that can be accessed by processors. A flow of breathing gas can be provided 301 to a delivery system, such as a therapeutic injector module. The flow of breathing gas may be provided from a ventilator to an injector module as described above. A flow of therapeutic gas comprising nitric oxide can also be provided 302 to the delivery system. The flow of breathing gas can be measured 303, and this measured flow of breathing gas may be displayed 304 on a display module. The flow of therapeutic gas can be also measured 310. The measured flow rates of breathing gas and therapeutic gases can then be used to determine a calculated dose of nitric oxide 311, and then the calculated dose of nitric oxide may be displayed 312. Instead of using a measured flow rate of therapeutic gas, a known flow rate of therapeutic gas may be used. The measured flow of breathing gas and/or the calculated dose of nitric oxide may be compared 305 to a predetermined limit. In FIG. 3, the predetermined limit can be a low limit. If the measured flow of breathing gas and/or calculated dose is, for example, below 306 the predetermined limit, an alert can be provided 307. The breathing gas and therapeutic gas can then be delivered 308 to a patient. For example, the injector module may combine the flow of breathing gas from the ventilator with the flow of therapeutic gas from the nitric oxide delivery device and provide this combined flow to the patient. If the measured flow of breathing gas and/or calculated dose is, for example, not be below 306 the predetermined limit, then the breathing gas and therapeutic gas can be delivered 308 to a patient without providing 307 an alert. Any of the steps provided above are optional, and the scope of any particular method is not limited by the specific combination shown in FIG. 3.

Figure 4:
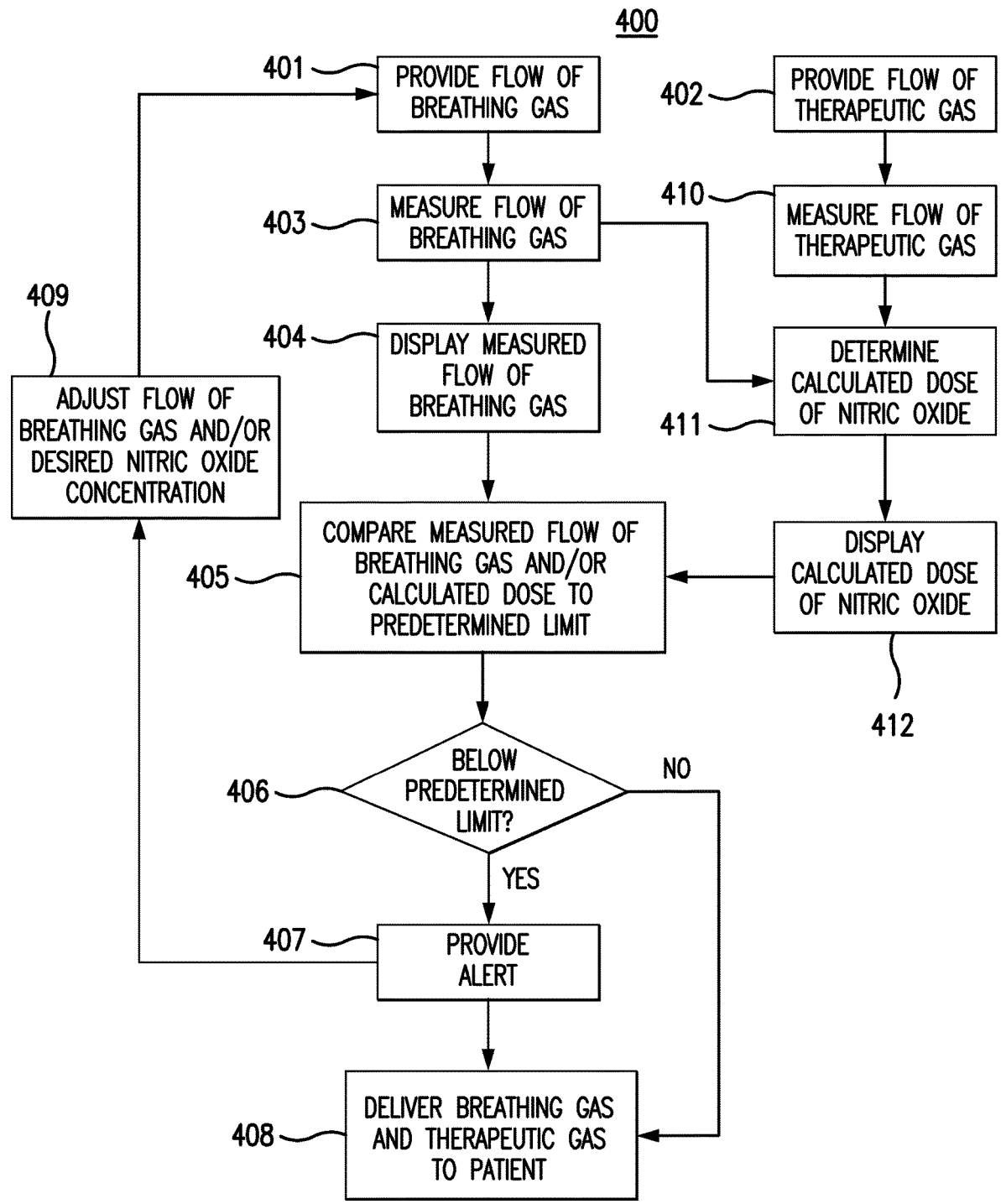
FIG. 4 depicts a flow chart for exemplary methods of monitoring the delivery of therapeutic gas with a feedback loop to drive NO dose or adjust flows to a patient, in accordance with exemplary embodiments of the present invention.

FIG. 4 depicts a flow chart for at least one exemplary embodiment of a method 400 for monitoring the delivery of therapeutic gas to a patient. Flow chart 400 can be an algorithm affiliated with clinical decision support that can be stored in processor readable memory that can be accessed by processors. A flow of breathing gas can be provided 401 to a delivery system, and/or a flow of therapeutic gas comprising nitric oxide can be also provided 402. The flow of breathing gas can be measured 403, and the measured flow of breathing gas may be displayed 404 on a display module. The flow of therapeutic gas can be also measured 410. The measured flow rates of breathing gas and therapeutic gases can then be used to determine a calculated dose of nitric oxide 411, and then the calculated dose of nitric oxide may be displayed 412. The measured flow of breathing gas and/or the calculated dose of nitric oxide may be compared 405 to a predetermined limit, which can be a low limit in FIG. 4. As with FIG. 3, if the measured flow of breathing gas and/or the calculated dose is, for example, below 406 the predetermined limit, an alert can be provided 407. In response to the alert provided 407, the flow rate of breathing gas and/or the desired nitric oxide concentration may be adjusted 409. The breathing gas and therapeutic gas comprising nitric oxide can then be delivered 408 to the patient. If the measured flow of breathing gas and/or calculated dose is, for example, not be below 406 the predetermined limit, then proceed directly to delivering 408 the breathing gas and therapeutic gas comprising nitric oxide. Again, any of the steps provided above are optional, and the scope of any particular method is not limited by the specific combination shown in FIG. 4.

Referring to FIGS. 2, 5B, 7B, & 8A-8F, in exemplary embodiments, systems of the present invention can be non-portable systems. Non-portable systems can be used for delivering and/or monitoring delivering of a therapeutic gas comprising nitric oxide to a patient. Non-portable systems can utilize and/or modify the teachings disclosed herein and/or incorporated by reference to deliver and/or monitor delivering of a therapeutic gas comprising nitric oxide to a patient. For example, delivering and/or monitoring delivery of a therapeutic gas to a patient, the non-portable system can include, but is not limited to, a therapeutic gas supply comprising nitric oxide; a breathing gas delivery system that provides breathing gas to a patient; and/or a therapeutic gas delivery system.

Referring to FIGS. 5C, 7C, & 9A-13G, in exemplary embodiments, systems of the present invention can be portable systems. Portable systems can be used for delivering and/or monitoring delivering of a therapeutic gas comprising nitric oxide to a patient. Portable systems can utilize and/or modify the teachings disclosed herein and/or incorporated by reference to deliver and/or monitor delivering of a therapeutic gas comprising nitric oxide to a patient. For example, delivering and/or monitoring delivery of a therapeutic gas to a patient, the portable system can include, but is not limited to, a therapeutic gas supply comprising nitric oxide; a breathing gas delivery system that provides breathing gas to a patient; and/or a therapeutic gas delivery system.

As illustratively depicted in at least FIGS. 9A-9B, 9F-9G, 10A-10B, 10E-10G, 11G, & 12A-12B, a small tank containing therapeutic gas supply comprising nitric oxide can be located within the system. Further, the system can include various components housed within the system and/or that can be located external to the system. Components that can be housed within the system can include, but is not limited to, a first inlet, a second inlet, a therapeutic injector module, an outlet, a control circuit, a first flow sensor, an indicator, a CPU, a second flow sensor, a sample block, and/or any other reasonable component for the delivery and/or monitoring of delivery of a therapeutic gas.

It will be understood that exemplary systems presented in drawings and/or described herein can include ornamental characteristics. These ornamental characteristics for various alternative designs may be non-functional and/or may not be dictated by function. For example, alternative designs, having various and/or alternative ornamental characteristics, may be used to perform the same functions, for example, such as those functions disclosed herein.

It is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments. The order of description of the above method should not be considered limiting, and methods may use the described operations out of order or with omissions or additions.

It is to be understood that the above description is intended to be illustrative, and not restrictive. Many other embodiments will be apparent to those of ordinary skill in the art upon reviewing the above description. The scope of the invention should, therefore, be determined with reference to the appended claims, along with the full scope of equivalents to which such claims are entitled.

It will be understood that any of the steps described can be rearranged, separated, and/or combined without deviated from the scope of the invention. For ease, steps are, at times, presented sequentially. This is merely for ease and is in no way meant to be a limitation.

Further, it will be understood that any of the elements and/or embodiments of the invention described can be rearranged, separated, and/or combined without deviated from the scope of the invention. For ease, various elements are described, at times, separately. This is merely for ease and is in no way meant to be a limitation.

Although the invention herein has been described with reference to particular embodiments, it is to be understood that these embodiments are merely illustrative of the principles and applications of the present invention. It will be apparent to those skilled in the art that various modifications and variations can be made to the method and system of the present invention without departing from the spirit and scope of the invention. Thus, it is intended that the present invention include modifications and variations that are within the scope of the appended claims and their equivalents.

What is claimed is:

1. A delivery system, comprising:
    a control module comprising one or more processors and a processor readable memory, the control module configured to control a flow of therapeutic gas comprising nitric oxide that is mixed with a flow of breathing gas to form a gas mixture into a nebulizer device for delivery of the gas mixture to a patient;
    a sample block configured to evaluate a presence and concentration of one or more of nitric oxide, oxygen and nitrogen dioxide in the gas mixture; and
    a display configured to display an option to activate a nebulizer mode and receive run information including start nebulizer mode information and duration run nebulizer mode information,
    wherein the control module is configured to:
        store logic based information for the nebulizer mode, the start nebulizer mode information, and the duration run nebulizer mode information,
        cause the sample block to cease evaluating the gas mixture in response to an input that the nebulizer device is in use for a duration of time based on the received duration run nebulizer mode information while continuing to deliver the gas mixture to the patient through the nebulizer device,
        return to evaluating the gas mixture after the duration of time, and
        cause to be presented on the display a calculated delivery dose of nitric oxide when the sample block is not evaluating the gas mixture and a measured concentration of nitric oxide when the sample block is evaluating.

2. The delivery system of claim 1 wherein the input is a user input.

3. The delivery system of claim 1 wherein the sample block receives a portion of the gas mixture via a sample line.

4. The delivery system of claim 1 wherein the control module is configured to cause to be presented on the display a calculated delivery dose when the sample block is not evaluating the gas mixture.

5. The delivery system of claim 1 wherein the duration of time is input by a user.

6. The delivery system of claim 5 wherein the sample block is integrated with the control module.

7. A therapeutic gas delivery system
    a source of a therapeutic gas comprising nitric oxide;
    a control module configured to control a flow of therapeutic gas from the therapeutic gas source to a therapeutic injector module where the therapeutic gas is combined with a breathing gas to form a gas mixture for delivery into a nebulizer device for delivery of the gas mixture to a patient; and
    a display configured to display an option to activate a nebulizer mode and receive run information including start nebulizer mode information and duration run nebulizer mode information,
    wherein the control module is configured to:
        test the gas mixture for at least one of nitric oxide concentration, oxygen concentration, and nitrogen dioxide concentration when the control module is not operating in the nebulizer mode,
        not to test the gas mixture when the control module is operating in the nebulizer mode for a duration of time based on the received duration run nebulizer mode information while continuing to deliver the gas mixture to the patient through the nebulizer device,
        return to testing the gas mixture after the duration of time, and
        cause to be presented on the display a calculated delivery dose of nitric oxide when the gas mixture is not being tested and a measured concentration of nitric oxide when the gas mixture is being tested.

8. The therapeutic gas delivery system of claim 7, wherein the control module is configured to cause to be presented on the display an indication that the control module is operating in the nebulizer mode.

9. The therapeutic gas delivery system of claim 8 wherein the control module is configured to enter the nebulizer mode in response to an input.

10. The therapeutic gas delivery system of claim 9 wherein the display is a touch screen display and the input is a user input to the touch screen display.

11. The therapeutic gas delivery system of claim 7 wherein the control module is configured to issue an alert when a calculated dosage of the therapeutic gas in the gas mixture is one of above a first threshold and below a second threshold.

12. A therapeutic gas delivery system, comprising:
    a source of a therapeutic gas comprising nitric oxide;
    a first inlet in fluid communication with the source of therapeutic gas;
    a second inlet in fluid communication with a breathing gas delivery system configured to deliver breathing gas to a patient;
    a therapeutic injector module in fluid communication with the first inlet, the second inlet, and an outlet leading to an inspiratory breathing hose;
    the therapeutic injector module having a sensor configured to measure a flow rate of the breathing gas and being configured to deliver a gas mixture of the breathing gas and the therapeutic gas to the outlet for delivery into a nebulizer device for delivery of the gas mixture to the patient;

a control module including at least one processor, at least one memory and a sample block, and that is configured to control a flow of therapeutic gas into the first inlet;

a sample line in fluid communication with the inspiratory breathing hose and the sample block;

wherein the sample block is configured to selectively divert a portion of the gas mixture through the sample line and is configured to analyze one or more of concentration of nitric oxide, concentration of oxygen and concentration of nitrogen dioxide; and wherein the control module is further configured to:
  enter a nebulizer mode in response to an input, indicating that the nebulizer device is anticipated to influence the gas mixture,
  cause the sample block to cease diverting the portion of the gas mixture while continuing to deliver the gas mixture to the patient through the nebulizer device,
  return to testing the gas mixture after a duration of time, and
  cause to be presented on the display a calculated delivery dose of nitric oxide when the gas mixture is not being tested and a measured concentration of nitric oxide when the gas mixture is being tested.

13. The therapeutic gas delivery system of claim 12, further comprising:
  a display;
  wherein the control module is configured to determine a calculated delivery concentration of nitric oxide using the flow rate of the breathing gas and a flow rate of the therapeutic gas; and
  wherein the calculated delivery concentration is presented on the display when the control module is in the nebulizer mode.

14. The therapeutic gas delivery system of claim 13 wherein when the control module is not in the nebulizer mode it is configured to cause to be presented on the display one of a concentration of nitric oxide, a concentration of oxygen and a concentration of nitrogen dioxide as determined by the sample block.

15. The therapeutic gas delivery system of claim 13 wherein the input is a user input into the control module.

16. The therapeutic gas delivery system of claim 12 wherein the control module is configured to exit the nebulizer mode after a predetermined interval.

17. The therapeutic gas delivery system of claim 16 wherein the predetermined interval is determined from user input.

18. The therapeutic gas delivery system of claim 12 wherein the control module causes the sample block to continuously analyze the gas mixture when the control module is not in the nebulizer mode.

* * * * *